United States Patent [19]

Linwood et al.

[11] Patent Number: 4,600,827
[45] Date of Patent: Jul. 15, 1986

[54] DUAL-POWERED PYROLYSIS PROBE DRIVING CIRCUIT

[75] Inventors: Gary C. Linwood, Newark, Del.; Robert Laragione, Christiana, Pa.

[73] Assignee: AE/CDS Autoclave, Inc., Oxford, Pa.

[21] Appl. No.: 655,380

[22] Filed: Sep. 28, 1984

[51] Int. Cl.⁴ .............................................. H05B 1/02
[52] U.S. Cl. .................................. 219/492; 219/201; 219/497; 219/501; 356/312
[58] Field of Search ............... 219/202, 203, 201, 492, 219/493, 494, 497, 501, 507–509; 356/312; 307/117; 123/179 H

[56] References Cited

U.S. PATENT DOCUMENTS

| | | | |
|---|---|---|---|
| 4,302,662 | 11/1981 | Kicherer et al. | 219/492 |
| 4,348,583 | 9/1982 | Bube et al. | 219/492 |
| 4,375,205 | 3/1983 | Green | 219/492 |
| 4,486,648 | 12/1984 | Grasso | 219/492 |
| 4,493,298 | 1/1985 | Kawamura | 219/497 |

FOREIGN PATENT DOCUMENTS 0839551  6/1960  United Kingdom ............... 219/492

Primary Examiner—M. H. Paschall
Attorney, Agent, or Firm—Nelson E. Kimmelman

[57] ABSTRACT

A dual power-supply system is used to produce a sharp rise-time characteristic and a high steady-state temperature in a platinum ribbon pyrolysis probe. First, a small "boost" power supply generates a very short, high power pulse that is applied to the probe. Then, at its peak, the first power supply is effectively disabled and a second power supply is brought into play to maintain the power (and the temperature) in the probe at a high steady-state value approximating the peak value of the boost pulse.

8 Claims, 7 Drawing Figures

1

DUAL-POWERED PYROLYSIS PROBE DRIVING CIRCUIT

BACKGROUND OF THE INVENTION

A. Field of the Invention

This invention relates to pyrolysis instruments (pyrolyzers) and, more particularly, to improved pyrolysis instrument systems for attaining much higher pyrolysis temperatures within a much shorter time than are achieved by conventional ones.

B. Prior Art

Previously, pyrolyzers were known such as Model 121 "Pyroprobe" manufactured by Chemical Data Systems, Inc. of Oxford, Pa. These pyrolyzers, while useful for many purposes had certain limitations. One of them was an inability to produce within a very short time a desired very high temperature. For certain research projects, such as the pyrolysis study of products of combustion released by smoldering as opposed to flame type fires, the rate of increase in the temperature to which the substance being studied is subjected may reveal what pyrolysis products are released during successive time intervals. With conventional pyrolyzers if a very sharp rise time characteristic for the temperature on the probe was achieved, there was a noticeable dip in the temperature curve of the probe just after it first achieved a maximum temperature. Investigation revealed that the lowering of the temperature in that region of the curve, especially when very high temperatures were to be attained, was due to the construction of the probe used with the pyrolysis instrument. In the case of platinum ribbon used as the heat-generating element of the probe, it was found that its welding connections acted as a heat sink and were in large part responsible. This dip prevented the making of accurate and reproducible studies under high temperature conditions which were to be subsequently analyzed by apparatus such as gas chromatographs, for example.

It is therefore among the objects of the present invention to provide pyrolysis apparatus which:

1. Can more rapidly attain a desired steady-state temperature.
2. Having attained a higher temperature, can maintain it without significant "dips" just after the probe initially attains its predetermined maximum temperature.
3. Provide more diversified programmed pyrolyses including much slower increases in temperature as well as much faster ones than are conventionally available.
4. Provide a more accurate indication of the average temperature on a pyrolysis probe.
5. Provide greater diversity and flexibility in generating and choosing operating modes of the pyrolysis probe.

SUMMARY OF THE INVENTION

A pyrolysis probe energizing system is powered initially by a high voltage pulse of very short duration from a first power supply to achieve a very steep temperature rise-time characteristic. Then the first supply is effectively disabled and a second power supply is switched in to maintain the previously generated high steady state temperature.

DETAILED DESCRIPTION OF THE INVENTION

Figure 1:
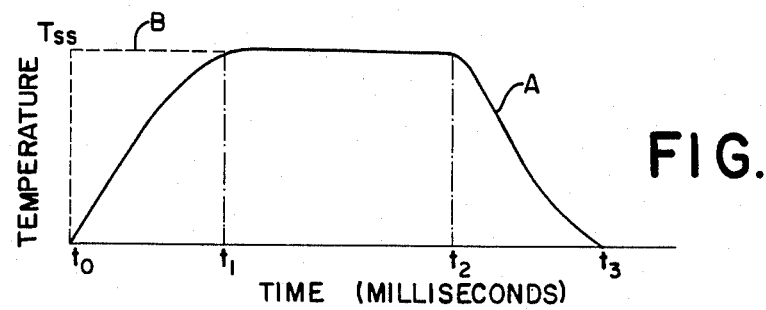
FIG. 1 is a drawing depicting the temperature-time characteristics of conventional pyrolysis apparatus and an idealized curve of a desired pryolyzer temperature-time characteristic.
Figure 2:
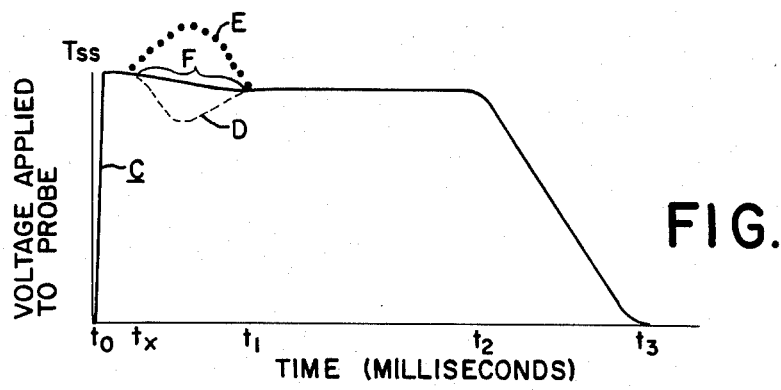
FIG. 2 shows curves illustrating the general theory and operation of one feature of the present invention.

FIGS. 1 and 2

FIG. 1 shows a generalized solid-line curve A indicating the temperature produced by a conventional pyrolysis probe using, for example, a platinum coil. It is seen that a number of milliseconds elapse from the time $t_o$ that current is first applied to the probe to the time $t_1$ at which it reaches its maximum, steady-state or "hold" temperature $T_{SS}$. As explained above, the time interval required to attain $T_{SS}$ may be considerably longer than desired. The broken-line curve B is idealized and shows a much more rapid leading edge characteristic.

In an effort to attain a very short rise time to the steady state temperature condition, much higher temperatures have been generated in the main element of the pyrolysis probe. For this purpose, some probes were used having an active heating element made of platinum ribbon. The ribbon has a very low thermal inertia as compared with a platinum coil used in conventional models which are considerably slower in attaining the desired temperature. The use of such ribbons and appropriate energizing circuits has enabled the production of much steeper leading edges of the temperature-time characteristic curve as shown at curve C in FIG. 2. However, as seen in the hyphenated portion D, just after the temperature $T_{SS}$ is first attained at time $t_x$, even though the probe continued thereafter to be energized with a constant voltage, a dip would appear in the curve C. At a time $t_1$ the amplitude of the curve C would regain its former maximum value. In accordance with the present invention, it is desirable to offset the dip by producing a corrective or compensatory signal voltage E (dotted line) in the interval $t_0-t_1$. Since the dip is caused by the characteristics of the probe itself, the corrective voltage E restores the temperature produced in the probe in the interval $t_x-t_1$ to the value as shown by the solid line section F of curve C.

The platinum ribbon is very expensive and very temperature-vulnerable. If it is heated too quickly or for too long a time, it could be destroyed. If it is subjected to a sudden initial surge of power say, 100 watts, from a power supply, it might easily be damaged. Moreover, if that amount of current were continuously applied to it after a gradual build-up, it also risks being burned up. Therefore, one way to solve the problem would be to provide means for dissipating that excessive power. This would entail a large and expensive power supply system.

In accordance with the present invention, the desired temperature characteristic of the probe from $t_0$ to $t_1$ is produced by first using a "boost" pulse type of power supply for a very short predetermined time interval derived as a function of the ultimate steady state temperature to be attained. Then, at $t_1$, the boost power supply is effectively turned off and from that point on, the energization of the probe is supplied by a second or main power supply. The latter's output is closely regulated by a special driving circuit including timers and acting in response to a central processing unit and to the sensed true average temperature signal derived from the probe itself.

Figure 3:
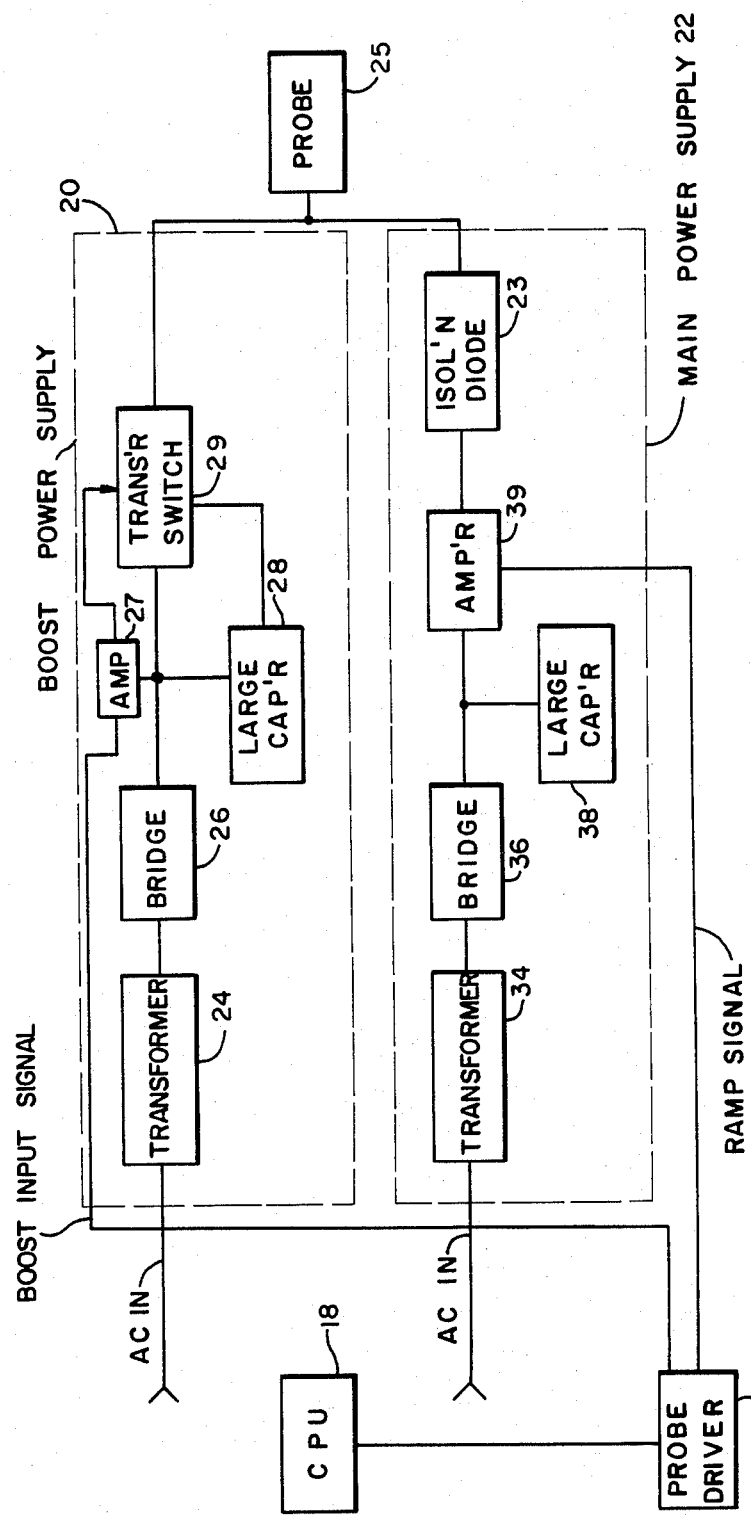
FIG. 3 is a block diagram of the dual power supply feature of the present invention.

FIG. 3—General Overview of System

Figure 5:
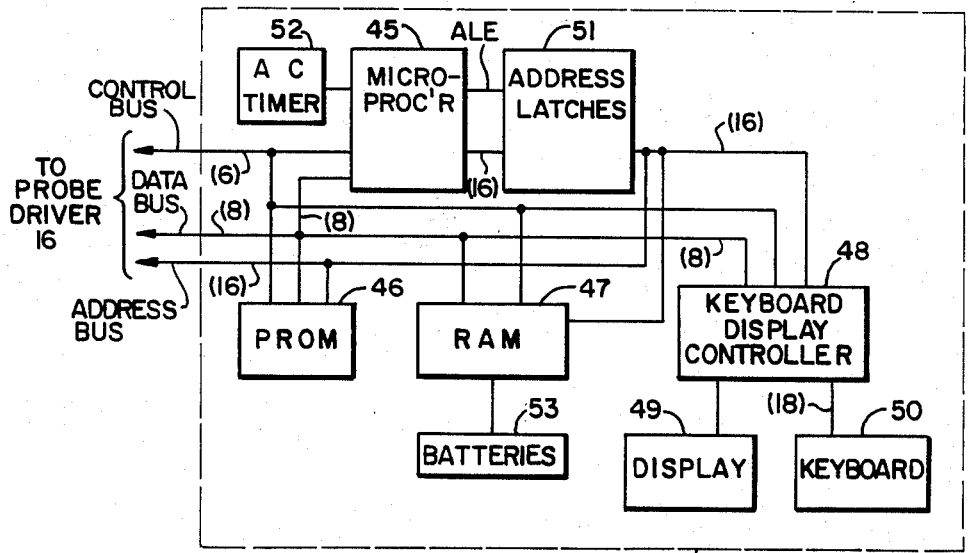
FIG. 5 is a block diagram of the main components of the CPU shown in FIG. 3.

FIG. 3 shows the overall system in a block diagram. It comprises a central processing unit 18 (FIG. 5) which includes the usual arithmetic, memory and associated circuits. The CPU is coupled to a probe driver circuit 16. AC is inductively applied in boost power supply 20 to a transformer 24 to whose output a bridge 26 is connected. A large capacitor 28 is connected to the output of the bridge which is coupled to a transistor switch 29. The switch is enabled to pass to the probe 25 the voltage built up in the capacitor 28 when the "boost trigger" signal from CPU 18 is applied to it via amplifier 27. Boost power supply 20 provides the initial high power pulse to the probe 25 during the first interval $t_x - t_1$ (FIG. 2).

The second or main power supply 22 also includes a transformer 34 to whose input AC is applied inductively. The output of the transformer is coupled to a rectifying bridge 36 and the output of the latter is coupled to a large capacitor 38 and to an amplifier 39. The latter's output is also connected to an isolation diode 23 intermediate the amplifier 39 and probe 25. The diode prevents the "boost" power pulse from boost power supply 20 from affecting the main power supply 22.

The two power supplies are so arranged that the probe will effectively produce a single solid line curve C (FIG. 2) comprised of the initial high power boost pulse during the period $t_0 - t_1$ and, then without interruption, the steady state portion of curve C beginning at $t_1$ and ending at $t_3$ (FIG. 2).

Figure 4:
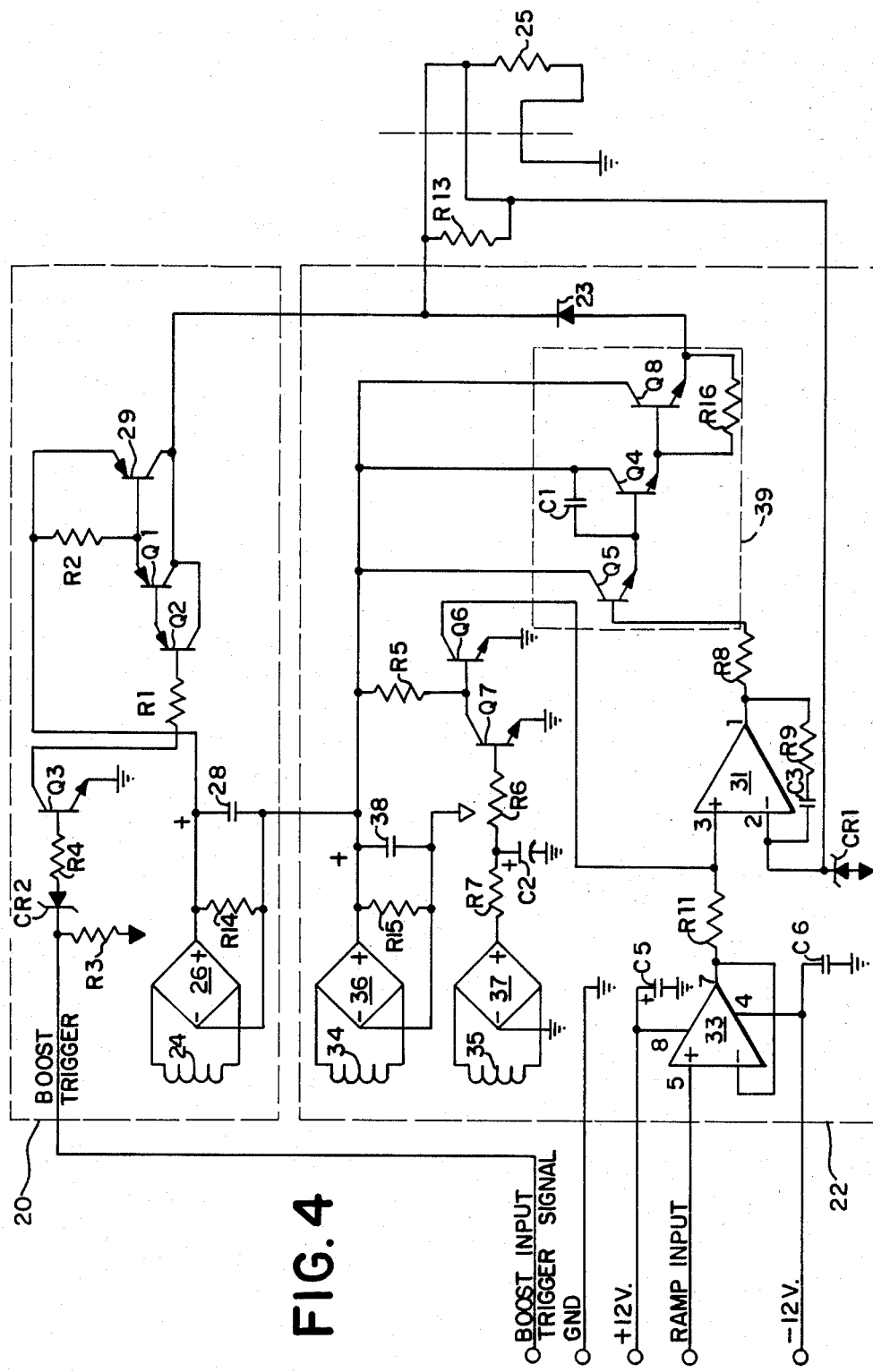
FIG. 4 is a schematic circuit diagram corresponding to the blocks of FIG. 3.

FIG. 4—Power Supplies Schematic

As stated above, there are two power supplies, the boost power supply 20 for the initial supply of the high power pulse to the pyrolysis probe 25 and the main power supply 22. Both supplies are operating at the time, computed by the CPU, that the boost power supply 20 is triggered by the boost trigger signal from the CPU. The trigger signal is applied to Zener diode CR2, through resistor R4 to an amplifying circuit comprising transistors Q3, Q2, and Q1. The amplified boost trigger signal from Q1 is applied to the base of switching transistor 29 whose emitter receives the DC from capacitor 28.

The DC is derived from a secondary winding 24 coupled to a primary winding (not shown) energized with AC. This power supply is not regulated. The line AC voltage is measured by the CPU and that quantity is factored into an equation by the CPU which sends the boost trigger signal in response thereto. The AC induced in winding 24 is rectified in bridge 26 and stored in a very high capacitor 28 which may have a value of, for example, 67,000 mf. With this large capacitor, even if there is a small initial AC applied to it, a voltage of approximately 20 volts DC can be produced. It is this voltage which is essentially switched into the circuit via switching transistor 29 when the latter has been rendered conductive by the amplified boost trigger signal originating in the probe driver 16 when commanded by the CPU 18. The DC signal is applied to the probe represented by the resistance 25. While it is so applied, the blocking diode 23 prevents the high power from affecting adversely the components of the main power supply 22.

The duration of the boost pulse might be, typically, 5.0 milliseconds, depending upon the ultimate temperature to be generated in the probe. Calculation of the duration of the initial pulse is accomplished in CPU 18 and when the boost trigger signal is applied to the switching transistor 29, about 40 volts may be produced across the probe.

The main power supply 22 includes a secondary winding 34 for producing an AC voltage which is then rectified in bridge 36 and applied to another very large capacitor 38 which may have the same or similar value as capacitor 28. The voltage builds up across the capacitor 38 and is applied to an amplifying circuit comprising Q5, Q4, and Q8. The isolating diode 23 is not needed to protect the main power supply 22 once the pulse from boost supply 20 has terminated since the latter power supply then goes off. However, once the boost pulse is ended, the amplified output appearing at the emitter of transistor Q8, which is a power transistor, passes through diode 23 and energizes the probe 25.

Not shown in the block diagram of FIG. 3 is a circuit just below coil 34, bridge 36, capacitor 38 and resistance R5 in FIG. 4. That includes a winding 35 into which AC is induced from a transformer primary, a bridge 37, and a filter (R7, C2) that supplies DC through resistor R6 to the base of Q7 which is in series with the base of Q6, the latter two transistors operating to determine whether or not AC power is present. If someone were to unplug the unit, or should there be a power failure, Q6 and Q7 operate to prevent the ramp signal, shown in FIG. 4 being applied to amplifier 33, from passing through amplifier 31 since the output signal of transistor Q6 will not appear at the positive input of circuit 31. This prevents possible burnout of the expensive platinum sensing element of probe 25.

In certain applications, it is desired that the temperature of the probe be raised or lowered in response to a ramp signal fed to main power supply by CPU 18. This signal is derived in accordance with a predetermined program for producing programmed temperatures at the probe. The ramp signal comes from the probe driver (from an output of digital-analog converter Z13 of FIG. 6) as will be explained later. The ramp signal goes to a buffer amplifier 33 whose output is applied to another amplifier 31. The latter amplifier must be protected from the high voltage produced in the boost power supply and for the reason Zener diode CR1 is used at one of its inputs. It prevents an excessive voltage pulse from being applied to one of the inputs of circuit 31. Amplifier 31 responds only to signals at its inputs having a predetermined ratio whereupon its output signal energizes the probe after amplification in the amplifier circuit 39 comprising transistors Q5, Q4 and Q8.

FIG. 5—CPU 18

As stated above, the CPU 18 instructs and controls the probe driver 16 which supplies the boost input signal to the boost power supply 20 and the ramp signal to the main power supply 22. The CPU includes a keyboard 50 and a monitor display 49 coupled to a keyboard display controller 48. The person at the keyboard controls the operation of the entire system. Commands are entered on the keyboard and displayed on display 49 and the signals are relayed from the keyboard via the keyboard display controller 48 to the various components of the CPU. While many connections are shown as single lines, it is to be understood that they represent, in most cases, a plurality of leads, the number of them being shown in parentheses in many cases. The commands entered onto the keyboard by the operator are executed by the CPU according to the program entered into the PROM 46. Processing of the command signals is done in the microprocessor 45 to which an AC timer 52 is connected. Cooperating with the microprocessor are a plurality of address latches 51 that are coupled to the PROM 46 and RAM 47, respectively. Batteries 53 are provided as a back up for the RAM 47 in case of power loss. A control bus conveys the READ, WRITE, RESET, clock, S1 (timing), and IO/M signals to the probe driver 16. The IO/M signal controls the directing of signals between the CPU and memory and between the CPU and the hardware devices. There is also a connection between the miroprocessor 45 and the address latches 51 for the ALE (address latch-enable) signal which actuates various ones of the address latches 57 as determined by the microprocessor 45. The display 49 may be, for example, 24 discrete LED's and 8 IEE alphanumeric LED's. The keyboard 50, for example, may be a keyboard manufactured by KB Denver Company of Denver, Colo.

Figure 6:
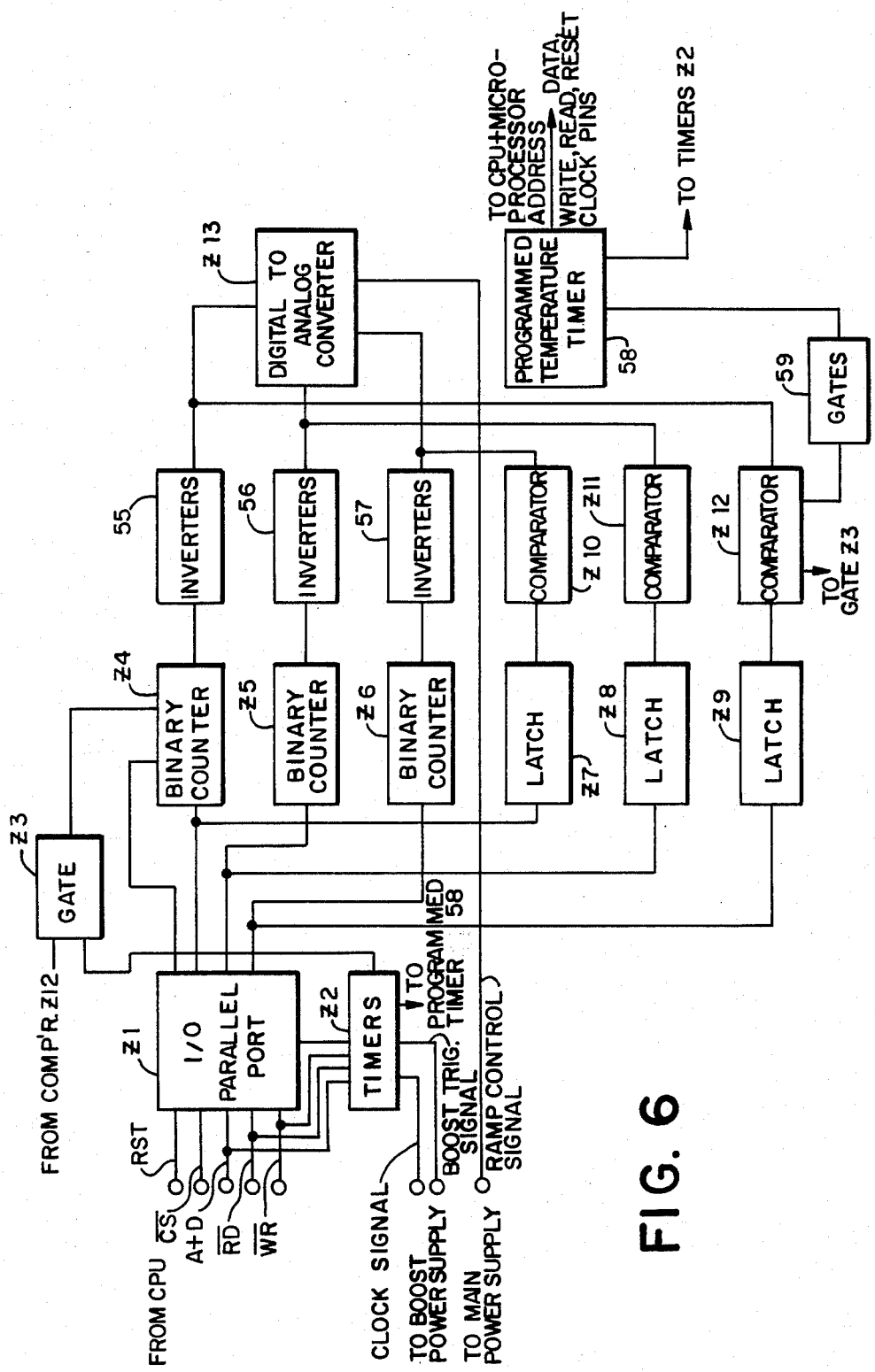
FIG. 6 is a block diagram of the probe driver shown in FIG. 3.
Figure 7:
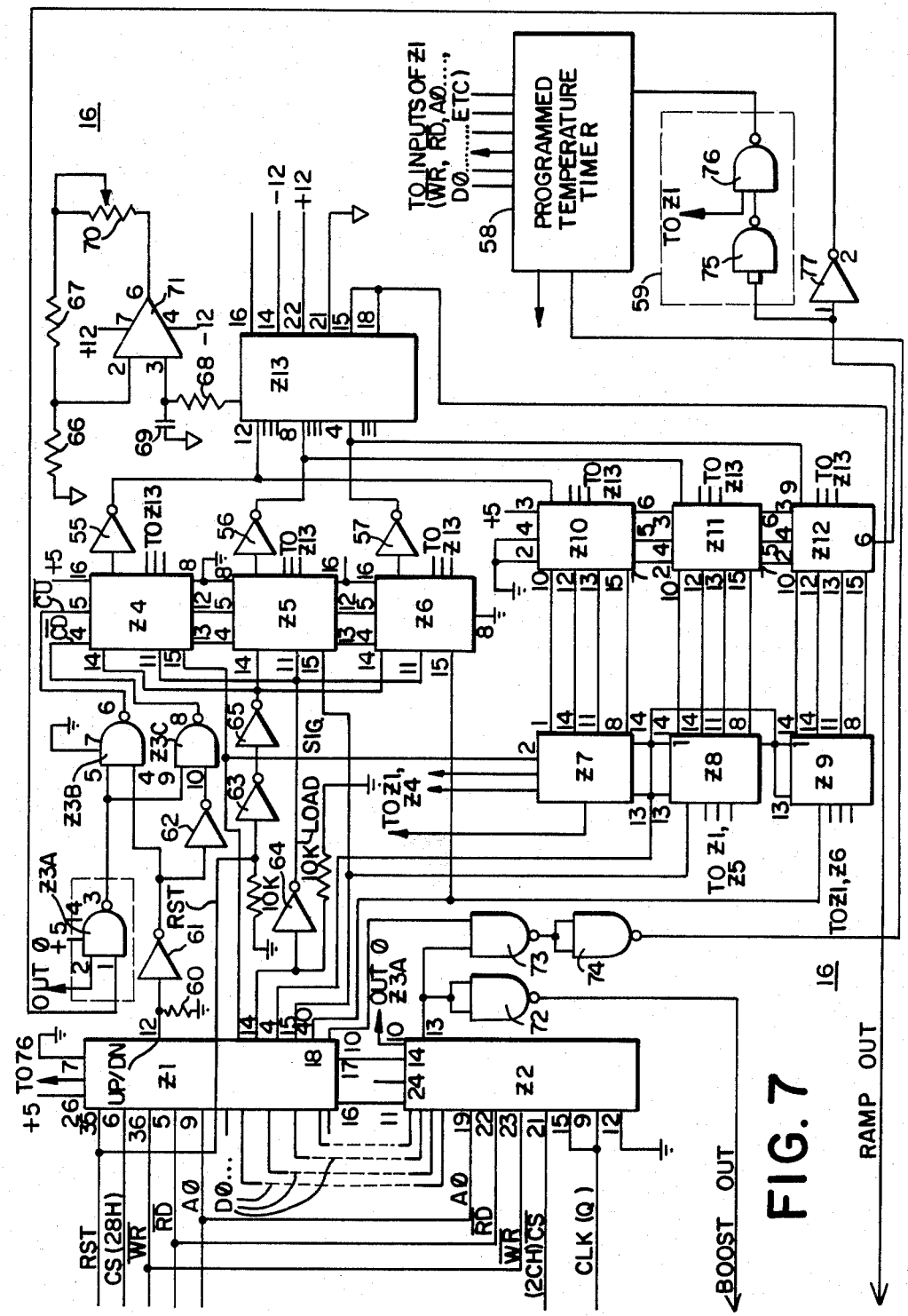
FIG. 7 is a schematic electrical diagram of a probe driver corresponding to the block diagram in FIG. 6.

FIGS. 6 and 7—Probe Driver 16

FIG. 6 is a block diagram of the probe driver 16 shown in shematic form in FIG. 7. The driver includes an input-output chip Z1. It serves to couple the CPU 18 to the external hardware. It also provides an analog voltage output signal corresponding to the value of the digital signal computed in CPU 18. This output signal, appearing at an output of digital-analog converter Z13, constitutes the ramp signal that is applied to main power supply 22. Additionally, it provides signals, in response to information received from the CPU 18, which instructs its counters whether they should count up or down so that the slope of the ramp signal may be determined accordingly. Z1 receives control, reset, write, read, address and data information from CPU 18 as do timers Z2 to which it is connected. Z1 also transmits a load signal to counters Z4, Z5 and Z6 for transferring the digital information at their inputs to outputs of Z4, Z5 and Z6 and to the inputs of the converter Z13.

A variable frequency pulse train of pin 10 of Z2 controls the rate at which the temperature of probe 25 is increased or decreased. This signal is applied to one input of a gate Z3A. So long as the probe is not of the desired temperature, Z3A passes the pulses on to gates Z3B and Z3C. The latter also receive on $\overline{UP}$/DN signal from Z1 which determines which way the counters Z4, Z5, and Z6 should count, i.e., up to the desired temperature or down to it.

Eventually the CPU 18 must know when the correct set or predetermined temperature has been generated and thus cease supplying digital signals representing higher temperatures to be generated. Since the CPU is not fast enough to work at the speeds required to drive the probe, there are provided a number of latches Z7, Z8 and Z9 which cooperate with a number of comparators Z10, Z11 and Z12 to monitor the count in counters Z6, Z5 and Z4. Latches store the temperature-representative digital signals from CPU, and comparators Z10, Z11 and Z12 continuously compare the count in Z7, Z8 and Z9 with the count of the digital signal relayed via counters Z4, Z5 and Z6 to converter Z13. So long as the two counts are unequal, gate Z3A will allow the pulses from Z2 to pass and this continues until parity of the counts is attained. At that instant a parity signal is generated at pin 6 of Z12 which is applied to amplifier 77 whose output signal applied to gate Z3A cuts the latter off. The same parity signal is applied to gate 75 and thence to one input of gate 76. The other input of the latter is connected to Z1 which supplies it with the probe ramp interrupt enable signal.

Associated with converter Z13 is an operational amplifier 71 which calibrates Z13. The potentiometer 70 setting determines how many volts one bit is equal to.

A reset signal from CPU 18 is applied to an input to Z1 and also directly to counters Z4, Z5 and Z6 to clear them so there is no voltage on probe 25 when the system is actuated.

Z2 provides at one of its outputs the boost trigger signal just discussed in connection with the boost power supply. This trigger signal is applied via gate 72 to power supply 20. Z2 is also coupled via gate 73 and 74 to a programmed temperature timing circuit 58 which times the steps of the ramp signal that controls the heating of the probe 25. Timer 58 consists of three chips which are coupled to Z2 for receiving time interval instructions computed by the CPU 18 in response to operation of the keyboard 50. After the predetermined time interval has elapsed, the timer 58 informs Z1 that it has timed out and steady state operation begins.

The particular digital-analog converter Z13 used requires negative inputs to produce an output. Associated with converter Z13 is an operational amplifier 71 which is used to set a reference voltage across the potentiometer 70 that calibrates Z13.

Z2, as stated above, provides the boost trigger voltage through gate 72. It is also coupled via gates 73 and 74 to the programmed timer 58.

| FIG. 4 | |
|---|---|
| Item | Description |
| R1 | 10K |
| R2 | 1K |
| R3 | 20K |
| R4 | 10K |
| R5 | 10K |
| R6 | 10K |
| R7 | 10K |
| R8 | 1K |
| R9 | 10K |
| R10 | 10K |
| R11 | 10K |
| R12 | 10K |
| R13 | 1K |
| R14 | 310 |
| R15 | 310 |
| R16 | 47 |
| Q1 | 2N5195 |
| Q2 | 2N2907A |
| Q3 | 2N3416 |
| Q4 | MJE200 |
| Q5 | MPS2222 |
| Q6 | 2N3416 |
| Q7 | 2N3416 |
| Q8 | 2N3055 |
| C1 | .01 mf |
| 28 | 67K mf |
| 38 | 67K mf |
| C2 | .1 mf |
| C3 | .01 mf |
| C5 | 1 mf |
| C6 | 1 mf |

FIG. 4 -continued

| Item | Description |
|---|---|
| CR1 | 1N4742A |
| 23 | MDA9906 |
| 29 | 2N5745 |
| 31 | LM1458 |
| 33 | LM1458 |

FIG. 5

| Item | Description |
|---|---|
| 45 | 8085 |
| 46 | 2716 |
| 47 | 5101 (NEC) or 6116 (Hitachi) |
| 48 | 8279 |
| 49 | 8-IEE alphanumeric LED's and is also 24 discrete LED's |
| 50 | KB Denver keyboard |
| 51 | 8212 |

FIG. 7

| | |
|---|---|
| Z1 | 8255 |
| Z2 | 8253 |
| Z3 | 7400 |
| Z4 | 74LS193 |
| Z5 | 74LS193 |
| Z6 | 74LS193 |
| Z7 | 74LS75 |
| Z8 | 74LS75 |
| Z9 | 74LS75 |
| Z10 | 74LS75 |
| Z11 | 74LS75 |
| Z12 | 74LS75 |
| Z13 | 7580 |
| 55 | 7404 |
| 56 | 7404 |
| 57 | 740W |
| 58 | 8253, 8255, 8259A |
| 59 | (2)74LS00 |
| 60 | 10K |
| 61 | 4049 |
| 62 | 4049 |
| 63 | 4049 |
| 64 | 4049 |
| 65 | 4049 |
| 66 | 100K |
| 67 | 1K |
| 68 | 10K |
| 69 | .01 mf |
| 70 | 5K |
| 71 | OP-07 |
| 72 | 74LS00 |
| 73 | 74LS00 |
| 74 | 74LS00 |
| 75 | 74LS00 |
| 76 | 74LS00 |
| 77 | 7404 |

APPENDIX

The accompanying print out of the program sets forth the program steps for controlling the apparatus shown in FIG. 3. Many of the program steps are directed to functions which are not pertinent to the invention, such as the keyboard/display interface and the oven control interface.

Those program steps which relate to the pyroprobe control are pertinent to the present invention. The pyroprobe control receives data inputted through the keyboard and performs calculations based on the inputted parameters as well as current temperature, final temperature, oven type and probe type. The calculations are completed before control of the probe is initiated. The results of the calculations are used to set the timers Z2 and 58 and the comparators Z10 through Z12. The "boost time" required to operate the second power supply to obtain high heating rates without overshoot or temperature dip is also determined along with the other calculations.

The program steps following the title "PYRO PROBE 1000" are broadly directed to the pyroprobe control. The initial portion of program steps under the aforementioned title deal with initially setting up the control.

The MSEC subroutine (steps 3303 through 331C) obtains the value for the time (in milliseconds) the probe is to be fired.

The RAMP subroutine (steps 331D through 3336) obtains the controlled heating rate for operating the second power supply.

The Boost subroutine (steps 3337 through 3350) provides the turn on for the second power supply.

The CALCULAPT (calculate probe temperature subroutine beginning at step 400C) performs preliminary calculations and sets up the IC's employed to control the pyroprobe.

The FAST LEVEL INTERVAL routine (beginning at program step 42FA) determines the corrections necessary for removing the dip in the temperature curve.

The VERY FAST RAMP routines 1 through 8 (program steps 451E through 48F8) performs the dip correction by generating 8 segments which comprise a mirror image of the dip in the temperature curve.

MAKRO ASSEMBLER AMA.2

```
0000                    NOEXP
8D00         SIM        MACRO        ; 8085 SIM INSTRUCTION
                        DB           30H
                        MACND
8D00         RIM        MACRO        ; 8085 RIM INSTRUCTION
                        DB           20H
                        MACND
8D00         CLC        MACRO
                        ORA          A
                        MACND
8D00         TIMER      MACRO        INTAL,RESET,COMPL,CBLOCK
                        LXI          H,INTAL
                        SHLD         CBLOCK
                        LXI          H,RESET
                        SHLD         CBLOCK+2
                        LXI          H,COMPL
                        SHLD         CBLOCK+4
                        LXI          H,CBLOCK
                        CALL         QUEUE
                        MACND
8D00         DELETE     MACRO        CBLOCK
                        LXI          H,CBLOCK
                        CALL         DEQUE
                        MACND
8D00         SAVE       MACRO
                                     ^S
                        PUSH         ^N^N
                                     ^Q
                        MACND
8D00         RESTOR     MACRO
                                     ^S
                        POP          ^N^N
                                     ^Q
                        MACND
8D00         SAVEALL    MACRO
                        SAVE         PSW,H,B,D
                        MACND
8D00         RESTALL    MACRO
                        RESTOR       D,B,H,PSW
                        MACND
8D00         MOVE       MACRO        BUFF1,BUFF2,NCH
                        LXI          B,BUFF1
                        LXI          D,BUFF2
                        MVI          L,NCH
             MV#
                        LDAX         B
                        INX          B
                        STAX         D
                        INX          D
                        DCR          L
                        JNZ          MV#
                        MACND
8D00         FILL       MACRO        BUFF1,CHAR,SIZE
                        LXI          B,BUFF1
                        MVI          A,CHAR
                        MVI          L,SIZE
             FL#
                        STAX         B
                        INX          B
                        DCR          L
                        JNZ          FL#
                        MACND
8D00         COMAND     MACRO        NCS,RTNS,CMDS
                        MVI          B,NCS
                        LXI          D,RTNS
                        LXI          H,CMDS
                        CALL         COMMD
                        MACND
8D00         WORDS      MACRO
                                     ^S
                        MVI          A,^N^N
                        OUT          KBDAT
                                     ^Q
                        MACND
8D00         RFIFO      MACRO
                        ; THIS MACRO SETS THE 8279 UP FOR A FIFO READ
                        MVI          A,40H
                        OUT          KBCNT
                        NOP
                        MACND
8D00         RDRAM      MACRO        ADDR,AUTO
                        MVI          A,ADDR+10H*AUTO+60H
                        OUT          KBCNT
                        NOP
                        MACND
8D00         WDRAM      MACRO        ADDR,AUTO
                        MVI          A,ADDR+10H*AUTO+80H
                        OUT          KBCNT
                        NOP
                        MACND
```

```
8D00        CLEAR       MACRO       CLR,CF,CX,LOOPN
                        MVI         A,0C0H+CLR*10H+CX+2*CF
                        OUT         KBCNT
            LOOPN       IN          KBCNT
                        ANI         80H ; CHECK FOR DISPLAY NOT AVAILABLE
                        JNZ         LOOPN
                        MACND
8D00        DRLC        MACRO       ARG1
                        IFEQ        ARG1,H;L1
                        ENDIF
                        IFEQ        ARG1,D;L2
                        ENDIF
                        PUSH        ARG1
                        XTHL
                        DAD         H
                        XTHL
                        POP         ARG1
                        GOTO        L3
            L1
                        DAD         H
                        GOTO        L3
            L2
                        XCHG
                        DAD         H
                        XCHG
                        GOTO        L3
            L3
                        MACND
8D00        DRCM        MACRO       ARG1
                        IFEQ        ARG1,H;L1
                        ENDIF
                        IFEQ        ARG1,B;L2
                        ENDIF
                        IFEQ        ARG1,D;L3
                        ENDIF
            L1
                        MOV         A,L
                        CMA
                        MOV         L,A
                        MOV         A,H
                        CMA
                        MOV         H,A
                        GOTO        L4
            L2
                        MOV         A,C
                        CMA
                        MOV         C,A
                        MOV         A,B
                        CMA
                        MOV         B,A
                        GOTO        L4
            L3
                        MOV         A,E
                        CMA
                        MOV         E,A
                        MOV         A,D
                        CMA
                        MOV         D,A
                        GOTO        L4
            L4
                        MACND
8D00        DR2CM       MACRO       ARG1
                        DRCM        ARG1
                        INX         ARG1
                        MACND
8D00        DRRC        MACRO       ARG1
                        CLC
                        IFEQ        ARG1,H;L1
                        ENDIF
                        IFEQ        ARG1,B;L2
                        ENDIF
                        IFEQ        ARG1,D;L3
                        ENDIF
            L1
                        MOV         A,H
                        RAR
                        MOV         H,A
                        MOV         A,L
                        RAR
                        MOV         L,A
                        GOTO        L4
            L2
                        MOV         A,B
                        RAR
                        MOV         B,A
                        MOV         A,C
                        RAR
                        MOV         C,A
                        GOTO        L4
            L3
                        MOV         A,D
                        RAR
                        MOV         D,A
```

```
                    MOV       A,E
                    RAR
                    MOV       E,A
                    GOTO      L4
           L4
                    MACND
SD00       INPIC    MACRO
                    MVI       A,10010111B
                    OUT       PIC.CNTR ; ICW1: VECTORS AT 0080H, 4 BYTES, SINGLE, ICW4
                    XRA       A
                    OUT       PIC.CNTR+1 ; ICW2: VECTORS AT 0080H
                    MVI       A,002H
                    OUT       PIC.CNTR+1 ; ICW4: AUTO-EOI
                    MACND
SD00       KILLPROB MACRO
                    XRA       A
                    STA       P.IMAGE
                    OUT       PRB.PIA+2
                    STA       T.IMAGE
                    OUT       TIM.PIA
                    MACND
SD00       INPROB   MACRO
                    MVI       A,10000000B ; ALL OUTPUTS
                    OUT       PRB.PIA+3
                    XRA       A
                    OUT       PRB.PIA ; ZERO TEMPERATURE
                    OUT       PRB.PIA+1
                    MVI       A,P.LOAD
                    OUT       PRB.PIA+2 ; CLEAR FUNCTIONS
                    XRA       A
                    OUT       PRB.PIA+2
                    STA       P.IMAGE
                    LXI       H,DUMMY
                    SHLD      RNEXT
                    SHLD      BNEXT
                    SHLD      PNEXT
                    MACND
SD00       SETEMP   MACRO     ARG1
                    IFEQ      ARG1,H;L1
                    ENDIF
                    IFEQ      ARG1,B;L2
                    ENDIF
                    IFEQ      ARG1,D;L3
                    ENDIF
                    GOTO      L4
           L1
                    MOV       A,L
                    OUT       PRB.PIA
                    MOV       A,H
                    OUT       PRB.PIA+1
                    GOTO      L5
           L2
                    MOV       A,C
                    OUT       PRB.PIA
                    MOV       A,B
                    OUT       PRB.PIA+1
                    GOTO      L5
           L3
                    MOV       A,E
                    OUT       PRB.PIA
                    MOV       A,D
                    OUT       PRB.PIA+1
                    GOTO      L5
           L4
                    LDA       ARG1
                    OUT       PRB.PIA
                    LDA       ARG1+1
                    OUT       PRB.PIA+1
                    GOTO      L5
           L5
                    LDA       P.IMAGE
                    ORI       P.LOAD
                    OUT       PRB.PIA+2
                    ANI       "P.LOAD
                    OUT       PRB.PIA+2
                    MACND
SD00       SETFNL   MACRO     ARG1
                    IFEQ      ARG1,H;L1
                    ENDIF
                    IFEQ      ARG1,B;L2
                    ENDIF
                    IFEQ      ARG1,D;L3
                    ENDIF
                    GOTO      L4
           L1
                    MOV       A,L
                    OUT       PRB.PIA
                    MOV       A,H
                    OUT       PRB.PIA+1
                    GOTO      L5
           L2
                    MOV       A,C
                    OUT       PRB.PIA
```

```
                MOV     A,B
                OUT     PRB.PIA+1
                GOTO    L5
        L3
                MOV     A,E
                OUT     PRB.PIA
                MOV     A,D
                OUT     PRB.PIA+1
                GOTO    L5
        L4
                LDA     ARG1
                OUT     PRB.PIA
                LDA     ARG1+1
                OUT     PRB.PIA+1
                GOTO    L5
        L5
                LDA     P.IMAGE
                ORI     P.FNL
                OUT     PRB.PIA+2
                ANI     "P.FNL
                OUT     PRB.PIA+2
                MACND
SD00    SETRATE MACRO   ARG1
                MVI     A,00110110B ; COUNTER0,LOAD,MODE3,BINARY
                OUT     PRB.CNTR+3
                IFEQ    ARG1,H;L1
                ENDIF
                IFEQ    ARG1,B;L2
                ENDIF
                IFEQ    ARG1,D;L3
                ENDIF
                GOTO    L4
        L1
                MOV     A,L
                OUT     PRB.CNTR
                MOV     A,H
                OUT     PRB.CNTR
                GOTO    L5
        L2
                MOV     A,C
                OUT     PRB.CNTR
                MOV     A,B
                OUT     PRB.CNTR
                GOTO    L5
        L3
                MOV     A,E
                OUT     PRB.CNTR
                MOV     A,D
                OUT     PRB.CNTR
                GOTO    L5
        L4
                LDA     ARG1
                OUT     PRB.CNTR
                LDA     ARG1+1
                OUT     PRB.CNTR
                GOTO    L5
        L5
                MACND
SD00    GORAMP  MACRO
                LDA     P.IMAGE
                OUT     PRB.PIA+2
                MACND
SD00    SETBST  MACRO   ARG1
                MVI     A,01110000B ; COUNTER1,LOAD,MODE1,BINARY
                OUT     PRB.CNTR+3
                IFEQ    ARG1,H;L1
                ENDIF
                IFEQ    ARG1,B;L2
                ENDIF
                IFEQ    ARG1,D;L3
                ENDIF
                GOTO    L4
        L1
                MOV     A,L
                OUT     PRB.CNTR+1
                MOV     A,H
                OUT     PRB.CNTR+1
                GOTO    L5
        L2
                MOV     A,C
                OUT     PRB.CNTR+1
                MOV     A,B
                OUT     PRB.CNTR+1
                GOTO    L5
        L3
                MOV     A,E
                OUT     PRB.CNTR+1
                MOV     A,D
                OUT     PRB.CNTR+1
                GOTO    L5
        L4
                LDA     ARG1
                OUT     PRB.CNTR+1
```

```
                              LDA        ARG1+1
                              OUT        PRB.CNTR+1
                              GOTO       L5
                   L5
                              MACND
8D00               GOBST      MACRO
                              LDA        P.IMAGE
                              OUT        PRB.PIA+2
                              MACND
8D00               DELAY      MACRO      ARG1
                              MVI        A,070H ; LOAD COUNTER 2, ONESHOT
                              OUT        TIM.CNTR+3
                              IFEQ       ARG1,H;L1
                              ENDIF
                              IFEQ       ARG1,B;L2
                              ENDIF
                              IFEQ       ARG1,D;L3
                              ENDIF
                              GOTO       L4
                   L1
                              MOV        A,L
                              OUT        TIM.CNTR+1
                              MOV        A,H
                              OUT        TIM.CNTR+1
                              GOTO       L5
                   L2
                              MOV        A,C
                              OUT        TIM.CNTR+1
                              MOV        A,B
                              OUT        TIM.CNTR+1
                              GOTO       L5
                   L3
                              MOV        A,E
                              OUT        TIM.CNTR+1
                              MOV        A,D
                              OUT        TIM.CNTR+1
                              GOTO       L5
                   L4
                              LDA        ARG1
                              OUT        TIM.CNTR+1
                              LDA        ARG1+1
                              OUT        TIM.CNTR+1
                              GOTO       L5
                   L5
                              LDA        T.IMAGE
                              ORI        T.INTE+T.TRGR ; ENABLE TIMER INTERUPTS
                              STA        T.IMAGE
                              OUT        TIM.PIA
                              MACND
8D00               INTIME     MACRO
                              MVI        A,10000000B
                              OUT        TIM.PIA+3
                              XRA        A
                              OUT        TIM.PIA ; CLEAR TIMER ENABLE AND INTERUPT ENABLE
                              STA        T.IMAGE
                              MVI        A,036H ; FIRST TIMER GIVES MILLISECOND PULSES
                              OUT        TIM.CNTR+3
                              LXI        H,1785 ; MILLISECONDS
                              MOV        A,L
                              OUT        TIM.CNTR
                              MOV        A,H
                              OUT        TIM.CNTR
                              MVI        A,T.MSEC
                              OUT        TIM.PIA+1
                              LXI        H,DUMMY
                              SHLD       TNEXT
                              MACND
0000                          ;
0000                          LINK       LABL.MAC,2
0000                          LINK       SYST.MAC,2
0000                          LINK       STEV.MAC,2
0000                          LINK       PYRO.MAC,2
0000                          LINK       PROB.MAC,2
0000                          LINK       IFAC.MAC,2
0000                          LINK       PRMT.MAC,2
0000                          END
0000    00                    NOP        ; BECAUSE OF ASHLEYS SCREWED UP ASSEMBLER
C800               RAMM0      SET        0C800H
D000               RAMM1      SET        0D000H
E000               RAMM2      SET        0E000H
E800               RAMM3      SET        0E800H
F000               RAMM4      SET        0F000H
F800               RAMM5      SET        0F800H
0001                          ;
0001                          USE        RAMM0
C800    AA         CONDIT1    DB         10101010B
0011               SZ.MTH     EQU        17
C801    1000       IMETHD0    DS         SZ.MTH
C812    1000       IMETHD1    DS         SZ.MTH
C823    1000       IMETHD2    DS         SZ.MTH
C834    1000       IMETHD3    DS         SZ.MTH
C845    1000       IMETHD4    DS         SZ.MTH
C856    1000       IMETHD5    DS         SZ.MTH
```

```
C867  1000        IMETHD6      DS    SZ.MTH
C878  1000        IMETHD7      DS    SZ.MTH
C889  1000        IMETHD8      DS    SZ.MTH
C89A  1000        IMETHD9      DS    SZ.MTH
C8AB  0B00        NDAYS        DS    12
C8B7  00          SECS         DS    1
C8B8  00          MINS         DS    1
C8B9  00          HOURS        DS    1
C8BA  00          DAYS         DS    1
C8BB  00          MONTHS       DS    1
C8BC  00          YEARS        DS    1
C8BD  0700        TIME         DS    8
C8C5  0700        DATE         DS    8
C8CD  0300        SCRATCH      DS    4
C8D1  0100        TSTFCTR      DS    2
C8D3  0F00        TSTRATES     DS    16
C8E3  0100        TSTFCTR1     DS    2
C8E5  0100        TSTSLP1      DS    2
C8E7  0100        TSTSLP2      DS    2
C8E9  0100        TSTFCTR2     DS    2
C8EB  0100        TSTFCTR3     DS    2
C8ED              ;
C8ED                           USE   RAMM1
D000  55          CONDIT2      DB    01010101B
D001  1000        PMETHD0      DS    SZ.MTH
D012  1000        PMETHD1      DS    SZ.MTH
D023  1000        PMETHD2      DS    SZ.MTH
D034  1000        PMETHD3      DS    SZ.MTH
D045  1000        PMETHD4      DS    SZ.MTH
D056  1000        PMETHD5      DS    SZ.MTH
D067  1000        PMETHD6      DS    SZ.MTH
D078  1000        PMETHD7      DS    SZ.MTH
D089  1000        PMETHD8      DS    SZ.MTH
D09A  1000        PMETHD9      DS    SZ.MTH
D0AB              ;
D0AB                           USE   RAMM2
E000  00          A1ST         DS    1 ; LEDS, 2 TOP ROWS
E001  00          B1ST         DS    1 ; LEDS, 2 MIDDLE ROWS
E002  00          C1ST         DS    1 ; LEDS, 2 BOTTOM ROWS
E003  00          A2ST         DS    1 ; IO PORT IMAGE
E004  00          B2ST         DS    1 ; IO PORT IMAGE
E005  00          C2ST         DS    1 ; IO PORT IMAGE
E006  00          A3ST         DS    1
E007  00          B3ST         DS    1
E008  00          C3ST         DS    1
E009  00          CH1IN        DS    1
E00A  00          CH1INH       DS    1
E00B  00          CH2IN        DS    1
E00C  00          CH2INH       DS    1
E00D  00          CH3IN        DS    1
E00E  00          CH3INH       DS    1
E00F  00          CH4IN        DS    1
E010  00          CH4INH       DS    1
E011  00          CH5IN        DS    1
E012  00          CH5INH       DS    1
E013  00          CH6IN        DS    1
E014  00          CH6INH       DS    1
E015  00          CH7IN        DS    1
E016  00          CH7INH       DS    1
E017  00          CH8IN        DS    1
E018  00          CH8INH       DS    1
E019  00          CH1OUT       DS    1
E01A  00          CH1OUTH      DS    1
E01B  00          CH2OUT       DS    1
E01C  00          CH2OUTH      DS    1
E01D  00          CH3OUT       DS    1
E01E  00          CH3OUTH      DS    1
E01F  00          CH4OUT       DS    1
E020  00          CH4OUTH      DS    1
E021  00          CH5OUT       DS    1
E022  00          CH5OUTH      DS    1
E023  00          CH6OUT       DS    1
E024  00          CH6OUTH      DS    1
E025  00          CH7OUT       DS    1
E026  00          CH7OUTH      DS    1
E027  00          CH8OUT       DS    1
E028  00          CH8OUTH      DS    1
E029              ;
E029                           USE   RAMM3
002C              SZ.RCBLK     EQU   44 ; SIZE OF A RAMP CONTROL BLOCK
E800  2B00        R1.CBLK      DS    SZ.RCBLK
E82C  2B00        R2.CBLK      DS    SZ.RCBLK
000A              SZ.IRCBK     EQU   10
E858              IR1.CBLK
E858  00          IR1.DIR      DS    1
E859  0100        IR1.DUR      DS    2
E85B  0100        IR1.DEST     DS    2
E85D  00          IR1.CNTRL    DS    1
E85E  0100        IR1.RATE     DS    2
E860  0100        IR1.STRT     DS    2
E862              IR2.CBLK
E862  00          IR2.DIR      DS    1
E863  0100        IR2.DUR      DS    2
```

```
E865  0100    IR2.DEST    DS    2
E867  00      IR2.CNTRL   DS    1
E868  0100    IR2.RATE    DS    2
E86A  0100    IR2.STRT    DS    2
E86C          IR.CBLK
E86C  00      IR.DIR      DS    1
E86D  0100    IR.DUR      DS    2
E86F  0100    IR.DEST     DS    2
E871  00      IR.CNTRL    DS    1
E872  0100    IR.RATE     DS    2
E874  0100    IR.STRT     DS    2
E876          ;
E876          USE RAMM4
0020          QSIZE  EQU  32
F000  3F00    QUELST   DS   QSIZE*2
F040  0500    CBLK01   DS   6
F046  0500    CBLK02   DS   6
F04C  0500    CBLK03   DS   6
F052  0500    CBLK04   DS   6
F058  0500    CBLK05   DS   6
F05E  0500    CBLK06   DS   6
F064  0500    CBLK07   DS   6
F06A  0500    CBLK08   DS   6
F070  0500    CBLK09   DS   6
F076  0500    CBLK10   DS   6
F07C  0500    CBLK11   DS   6
F082  0500    CBLK12   DS   6
F088  0500    CBLK13   DS   6
F08E  0500    CBLK14   DS   6
F094  0500    CBLK15   DS   6
F09A  0500    CBLK16   DS   6
F0A0  0500    CBLK17   DS   6
F0A6  0500    CBLK18   DS   6
F0AC  0500    CBLK19   DS   6
F0B2  0500    CBLK20   DS   6
F0B8          ;
F0B8          USE RAMM5
F800  0100    DSPTR1    DS   2
F802  0300    ABSLUT    DS   4
F806  00      IRUNFLG   DS   1
F807  00      IHLDFLG   DS   1
F808  00      UNUSED1   DS   1
F809  0700    DTBUF     DS   8
F811  00      CNT       DS   1
F812  00      DATI      DS   1
F813  00      RATE      DS   1
F814  0100    IELAPSE   DS   2
F816  0100    INEXT     DS   2
F818  0100    ITEMP     DS   2
F81A  00      CHAR      DS   1
F81B  0700    ETBUF     DS   8
F823  0700    IACTBUF   DS   8
F82B  0100    IRTIME    DS   2
F82D  0100    DSPTR2    DS   2
F82F  0700    PACTBUF   DS   8
F837  0100    ACTIVE    DS   2
F839  0100    INACTIVE  DS   2
F83B  0100    PELAPSE   DS   2
F83D  0100    PNEXT     DS   2
F83F  0100    PRTIME    DS   2
F841  0100    PTEMP     DS   2
F843  00      PRUNFLG   DS   1
F844  00      PHLDFLG   DS   1
F845  00      UNUSED2   DS   1
F846  0100    COUNT0    DS   2
F848  0100    COUNT1    DS   2
F84A  0100    COUNT2    DS   2
F84C  0100    COUNT3    DS   2
F84E  0100    COUNT4    DS   2
F850  0100    COUNT5    DS   2
F852  0100    COUNT6    DS   2
F854  0100    COUNT7    DS   2
F856  0100    COUNT8    DS   2
F858  0100    COUNT9    DS   2
F85A  0100    COUNTA    DS   2
F85C  0100    COUNTB    DS   2
F85E  0B00    PSTACK    DS   12
F86A          R.CBLK
F86A  00      R.DIR     DS   1
F86B  0100    R.DUR     DS   2
F86D  00      R.CNTRL1  DS   1
F86E  00      R.CNTRL2  DS   1
F86F  0100    R.STRT    DS   2
F871  0100    R.DEST1   DS   2
F873  0100    R.DEST2   DS   2
F875  0100    R.DEST3   DS   2
F877  0100    R.DEST4   DS   2
F879  0100    R.DEST5   DS   2
F87B  0100    R.DEST6   DS   2
F87D  0100    R.DEST7   DS   2
F87F  0100    R.DEST    DS   2
F881  0100    R.RATE    DS   2
F883  0100    R.RATE1   DS   2
```

```
F885  0100          R.RATE2      DS       2
F887  0100          R.RATE3      DS       2
F889  0100          R.RATE4      DS       2
F88B  0100          R.RATE5      DS       2
F88D  0100          R.RATE6      DS       2
F88F  0100          R.RATE7      DS       2
F891  0100          R.NEXT       DS       2
F893  00            R.IMPL       DS       1
F894  0100          R.SPACE      DS       2
F896  0100          TNEXT        DS       2
F898  0100          RNEXT        DS       2
F89A  0100          BNEXT        DS       2
F89C  00            P.IMAGE      DS       1
F89D  00            T.IMAGE      DS       1
F89E  00            PIRTN        DS       1
F89F  0100          CALPROBE     DS       2
F8A1  00            GASFACTOR    DS       1
F8A2  00            NFINTRPT     DB       0
0010                EQUAL        EQU      10H ; FIRST INPUT (C4) OF PORT C2 WHICH IS THE 710 COMPARATOR OUTPUT
0020                GCREADYIN    EQU      20H ; GC READY INPUT
F8A3                ;
F8A3                ;                     LED DEFINITIONS
F8A3                ;
0001                LD.MSEC      EQU      001H ; MILLISECOND
0002                LD.SEC       EQU      002H ; SECONDS
0004                LD.MIN       EQU      004H ; MINUTES
0008                LD.HOUR      EQU      008H ; HOURS
0010                LD.IFC       EQU      010H ; INTERFACE LED, A1ST
0020                LD.PRB       EQU      020H ; PROBE LED, A1ST
0040                LD.HBT       EQU      040H ; HEART BEAT
0080                LD.PRT       EQU      080H ; PRINT
0001                LD.AUS       EQU      001H ; AUTO-SAMPLE
0002                LD.GCST      EQU      002H ; GC START
0004                LD.AGCS      EQU      004H ; AUTO GC START
0008                LD.FTMP2     EQU      008H ; FINAL TEMP 2
0010                LD.GCRDY     EQU      010H ; GC READY
0020                LD.FTMP1     EQU      020H ; FINAL TEMP 1
0040                LD.RMP2      EQU      040H ; RAMP 2
0080                LD.IVL2      EQU      080H ; INTERVAL 2
0001                LD.RMP1      EQU      001H ; RAMP 1
0002                LD.IVL       EQU      002H ; INTERVAL
0004                LD.THP       EQU      004H ; THERMAL PROCESSING
0008                LD.AGCS2     EQU      008H ; AUTO GC START 2
0010                LD.INTH      EQU      010H ; INITIAL HOLD
0020                LD.PGC       EQU      020H ; PGC
0040                LD.DHS       EQU      040H ; DYNAMIC HEADSPACE
0080                LD.STA       EQU      080H ; THERMAL ANALYSIS
F8A3                ;
F8A3                ;                     MULTIPLEXER DEFINITIONS
F8A3                ;
008F                MUXMK        EQU      8FH ; MUX CODE MASK TO SAVE ALL EXCEPT MUX BITS TO MUXER
0070                MUX0         EQU      70H ; SPARGE MUX
0060                MUX1         EQU      60H ; DESORB MUX
0050                MUX2         EQU      50H ; VALVE OVEN MUX
0040                MUX3         EQU      40H ; TRAP A MUX
0030                MUX4         EQU      30H ; TRAP B MUX
0020                MUX5         EQU      20H ; TRANSFER LINE MUX
0010                MUX6         EQU      10H ; SPARE A MUX
0000                MUX7         EQU      0; SPARE B MUX
F8A3                ; I/O PORT DEFINITIONS
0000                A1           EQU      000H
0001                B1           EQU      001H
0002                C1           EQU      002H
0003                X1           EQU      003H
0004                A2           EQU      004H
0005                B2           EQU      005H
0006                C2           EQU      006H
0007                X2           EQU      007H
0008                A3           EQU      008H
0009                B3           EQU      009H
000A                C3           EQU      00AH
000B                X3           EQU      00BH
B800                TABLE1       EQU      0B800H ; TABLE OF TEMPERATURE TO DAC INPUT CONVERSIONS
B000                TABLE2       EQU      0B000H ; TABLE OF ADC OUTPUT TO TEMPERATURE CONVERSIONS
000C                KBDAT        EQU      00CH ; DATA FOR 8279
000D                KBCNT        EQU      00DH ; CONTROL FOR 8279
0001                DOT          EQU      1; DECIMAL POINT ON DISPLAY
0010                PREAD        EQU      10H ; A2 PORT PROCESSOR READY
0020                HEART        EQU      20H ; A2 PORT HEARTBEAT
0040                BATTRY       EQU      40H ;        12H PORT BATTERY CONDITION
F8A3                ;
F8A3                ;                     KEY DEFINITIONS
F8A3                ;
00E2                RMPRAT       EQU      0E2H ; RAMP RATE KEY
00C8                ENTER        EQU      0C8H ; ENTER KEY
00CB                DISPLY       EQU      0CBH ; DISPLAY KEY
00CF                KY.BOTH      EQU      0CFH ; BOTH KEY
00F4                KY.MTHR      EQU      0F4H ; METH RCL KEY
00EC                KY.MTHS      EQU      0ECH ; METH STR KEY
00E2                KY.RMPR      EQU      0E2H ; RAMP RATE KEY
00C8                KY.ENTER     EQU      0C8H ; ENTER KEY
00C9                KY.DTCLK     EQU      0C9H ; TIME DATE KEY
00CA                KY.STACT     EQU      0CAH ; SET ACT KEY
```

```
00CB            KY.DSPLY        EQU             0CBH ; DISPLAY KEY
00CC            KY.TBASE        EQU             0CCH ; TBASE KEY
00CD            KY.IFACE        EQU             0CDH ; INTER FACE KEY
00CE            KY.PROBE        EQU             0CEH ; PROBE KEY
00E6            KY.RESET        EQU             0E6H ; RESET KEY
00E4            KY.START        EQU             0E4H ; START KEY
00DC            KY.STOP         EQU             0DCH ; STOP KEY
00EE            KY.RESUM        EQU             0EEH ; RESUME KEY
00EF            KY.HOLD         EQU             0EFH ; HOLD KEY
00D7            KY.HOLD1        EQU             0D7H ; HOLD 1 KEY
00D6            KY.RAMP2        EQU             0D6H ; RAMP 2 KEY
00E5            KY.INIT         EQU             0E5H ; INIT KEY
00E9            KY.ZERO1        EQU             0E9H ; ZERO KEY
00EA            KY.ZERO2        EQU             0EAH ; ZERO KEY
00E8            KY.ZERO3        EQU             0E8H ; ZERO KEY
00F2            KY.ONE          EQU             0F2H ; ONE KEY
00F1            KY.TWO          EQU             0F1H ; TWO KEY
00F0            KY.THREE        EQU             0F0H ; THREE KEY
00C2            KY.FOUR         EQU             0C2H ; FOUR KEY
00C1            KY.FIVE         EQU             0C1H ; FIVE KEY
00C0            KY.SIX          EQU             0C0H ; SIX KEY
00D2            KY.SEVEN        EQU             0D2H ; SEVEN KEY
00D1            KY.EIGHT        EQU             0D1H ; EIGHT KEY
00D0            KY.NINE         EQU             0D0H ; NINE KEY
00D5            KY.FINAL        EQU             0D5H ; FINAL KEY
00DD            KY.RAMP1        EQU             0DDH ; RAMP 1 KEY
00F7            KY.DUMP         EQU             0F7H ; DUMP KEY
00DB            KY.INPT         EQU             0DBH ; INPUT KEY
00E3            KY.OUTPT        EQU             0E3H ; OUTPUT KEY
00DE            KY.SHFT         EQU             0DEH ; SHIFT
00CD            KY.PRBTP        EQU             0CDH ; PROBE TYPE
00D3            KY.PGC          EQU             0D3H ; PGC
00D4            KY.STC          EQU             0D4H ; SAMPLER TC
00DA            KY.GCF          EQU             0DAH ; CARRIER GAS FACTOR
00C7            KY.CAL          EQU             0C7H ; PROBE CALIBRATION
F8A3            ;
F8A3            ;                       DISPLAYABLE CHARACTERS
F8A3            ;
0010            CODE0           EQU             010H ; 0
0020            CODE1           EQU             020H ; 1
0030            CODE2           EQU             030H ; 2
0040            CODE3           EQU             040H ; 3
0050            CODE4           EQU             050H ; 4
0060            CODE5           EQU             060H ; 5
0070            CODE6           EQU             070H ; 6
0080            CODE7           EQU             080H ; 7
0090            CODE8           EQU             090H ; 8
00A0            CODE9           EQU             0A0H ; 9
0000            BLANK           EQU             000H ; SPACE
00B0            ACODE           EQU             0B0H ; A
00C0            BCODE           EQU             0C0H ; B
00E0            DCODE           EQU             0E0H ; C
00D0            CCODE           EQU             0D0H ; D
00F0            ECODE           EQU             0F0H ; E
0002            FCODE           EQU             002H ; F
0012            GCODE           EQU             012H ; G
0022            HCODE           EQU             022H ; H
0032            ICODE           EQU             032H ; I
0042            LCODE           EQU             042H ; L
0052            MCODE           EQU             052H ; M
0062            NCODE           EQU             062H ; N
0072            OCODE           EQU             072H ; O
0082            PCODE           EQU             082H ; P
0092            RCODE           EQU             092H ; R
00A2            SCODE           EQU             0A2H ; S
00B2            TCODE           EQU             0B2H ; T
00C2            UCODE           EQU             0C2H ; U
00D2            VCODE           EQU             0D2H ; V
00E2            WCODE           EQU             0E2H ; W
00F2            YCODE           EQU             0F2H ; Y
F8A3            ;
F8A3            ;                       SYSTEM CONSTANTS
F8A3            ;
0000            OF.INT          EQU             0 ; INITIAL OFFSET IN A METHOD BLOCK
0006            OF.HD1          EQU             6 ; HOLD 1 OFFSET              "
000C            OF.FNL          EQU             12 ; FINAL OFFSET              "
0005            OF.RP1          EQU             5 ; RAMP 1 OFFSET              "
000B            OF.RP2          EQU             11 ; RAMP 2 OFFSET             "
E400            STACK           EQU             0E400H ; STACK LOCATION
00FA            T.MAX           EQU             250 ; MAX INTERFACE TEMP
0006            T.MIN           EQU             006 ; MIN INTERFACE TEMP
0038            PIC.CNTR        EQU             038H ; PROGRAMMABLE INTERUPT CONTROLLER
0028            PRB.PIA         EQU             028H ; ADDRESS OF PROBE PIA
002C            PRB.CNTR        EQU             02CH ; ADDRESS OF PROBE RAMP COUNTER
0001            P.LOAD          EQU             001H ; PROBE SET TEMPERATURE BIT
0002            P.FNL           EQU             002H ; PROBE FINAL TEMP LATCH BIT
0004            P.TRGR          EQU             004H ; PROBE RAMP TRIGGER BIT
0010            P.INTE          EQU             010H ; PROBE RAMP INTERUPT ENABLE
0020            P.UPDN          EQU             020H ; PROBE RAMP DIRECTION BIT
0040            P.CLR           EQU             040H ; PROBE COUNTER CLEAR BIT
0008            B.TRGR          EQU             008H ; BOOST TRIGGER BIT
0080            B.INTE          EQU             080H ; BOOST ENABLE BIT
```

```
0030              TIM.CNTR    EQU         030H  ; INTERUPT TIMER
0034              TIM.PIA     EQU         034H  ; INTERUPT TIMER CONTROL PORT
0004              T.INTE      EQU         004H  ; TIMER INTERUPT ENABLE
0002              T.TRGR      EQU         002H  ; INTERUPT TIMER TRIGGER
0001              T.MSEC      EQU         001H  ; MILLISECOND TIMER ENABLE BIT
0003              BEEP.1      EQU         003H  ; LOW TONE
0005              BEEP.2      EQU         005H  ; MIDDLE TONE
0009              BEEP.3      EQU         009H  ; HIGH TONE
0031              GAS.PORT    EQU         031H
0032              CAL.PORT    EQU         032H
0080              AIR.FCTR    EQU         128
0080              HEL.FCTR    EQU         128
0080              VAC.FCTR    EQU         128
F8A3                          END
F8A3                          NOEXP
F8A3                          TITLE       --- PYRO PROBE 1000 ---
F8A3              ;                       PYRO PROBE 1000
F8A3              ;                       27-MAY-82
F8A3              ;                       ANDREW N. MESSENT
F8A3              ;                       COPYRIGHT MAY 1982, CHEMICAL DATA SYSTEMS
F8A3              ;
0000              AORG        SET         0000H ; RESET
0008              BORG        SET         0008H ; RST 1
0010              CORG        SET         0010H ; RST 2
0018              DORG        SET         0018H ; RST 3
0020              EORG        SET         0020H ; RST 4
0024              FORG        SET         0024H ; TRAP
0028              GORG        SET         0028H ; RST 5
002C              HORG        SET         002CH ; RST 5.5
0030              IORG        SET         0030H ; RST 6
0034              JORG        SET         0034H ; RST 6.5
0038              KORG        SET         0038H ; RST 7
003C              LORG        SET         003CH ; RST 7.5
0080              MORG        SET         0080H
0084              NORG        SET         0084H
0088              OORG        SET         0088H
008C              PORG        SET         008CH
0090              QORG        SET         0090H
0094              RORG        SET         0094H
0098              SORG        SET         0098H
009C              TORG        SET         009CH
3000              SYSTEM      SET         03000H ; SYSTEM ROUTINES AND LIBRARY FUNCTIONS
4000              EPROM4      SET         04000H ; WORK AREA
5000              EPROM5      SET         05000H
6000              EPROM6      SET         06000H
7000              EPROM7      SET         07000H
8000              PRGM        SET         08000H ; PROGRAM
F8A3              ;
F8A3              ;*********************************************************************
F8A3              ;
F8A3              ;             VECTORS            * * * * * * * * * * *
F8A3              ;
F8A3                          USE         AORG
0000  C30080                  JMP         INITAL ; POWER UP
0003                          USE         BORG
0008  C3B830                  JMP         UNUSED
000B                          USE         CORG
0010  C3B830                  JMP         UNUSED
0013                          USE         DORG
0018  C3B830                  JMP         UNUSED
001B                          USE         EORG
0020  C3B830                  JMP         UNUSED
0023                          USE         FORG
0024  C30030                  JMP         TIMQUE ; TRAP INTERUPTS
0027                          USE         GORG
0028  C3B830                  JMP         UNUSED
002B                          USE         HORG
002C  C3B830                  JMP         UNUSED
002F                          USE         IORG
0030  C3B830                  JMP         UNUSED
0033                          USE         JORG
0034  C3B830                  JMP         UNUSED
0037                          USE         KORG
0038  C3B830                  JMP         UNUSED
003B                          USE         LORG
003C  C3AA30                  JMP         RST75 ; KEYBOARD INTERUPT
003F                          USE         MORG
0080  C30333                  JMP         MSEC  ; EXECUTE MILLISECOND TIMER SERVICE ROUTINE
0083                          USE         NORG
0084  C31D33                  JMP         RAMP  ; EXECUTE RAMP SERVICE ROUTINE
0087                          USE         OORG
0088  C33733                  JMP         BOOST ; EXECUTE BOOST SERVICE ROUTINE
008B                          USE         PORG
008C  C3B830                  JMP         UNUSED
008F                          USE         QORG
0090  C3B830                  JMP         UNUSED
0093                          USE         RORG
0094  C3B830                  JMP         UNUSED
0097                          USE         SORG
0098  C3B830                  JMP         UNUSED
009B                          USE         TORG
009C  C3B830                  JMP         UNUSED
```

```
009F         ;***************************************************************************
009F         ;
009F                       USE          SYSTEM
3000         ;
3000         ;                  TIMER QUE ROUTINE          * * * * * * * * * * * *
3000         ;         CHECKS THE QUE FOR ANY ROUTINES DUE TO BE EXECUTED AT THE
3000         ;         CURRENT INTERVAL.
3000         ;
3000            TIMQUE
3000                       SAVEALL
3004 FB                    EI
3005 3AA2F8                LDA          NFINTRPT
3008 87                    ADD          A
3009 32A2F8                STA          NFINTRPT
300C 0620                  MVI          B,QSIZE ; GET THE NUMBER OF QUE ENTRIES
300E 2100F0                LXI          H,QUELST ; GET POINTER TO QUELIST
3011            TQ01
3011 AF                    XRA          A ; CLEAR ACCUMULATOR
3012 5E                    MOV          E,M
3013 B6                    ORA          M ; GET LEAST SIGNIFICANT BYTE
3014 23                    INX          H
3015 56                    MOV          D,M
3016 B6                    ORA          M ; OR WITH MOST SIGNIFICANT BYTE
3017 CA5030                JZ           TQ02 ; IF CURRENT QUE ENTRY IS EMPTY
301A                       SAVE         H
301B EB                    XCHG         ; PUT CONTROL BLOCK POINTER INTO 'HL'
301C 5E                    MOV          E,M ; GET THE COUNTER
301D 23                    INX          H
301E 56                    MOV          D,M
301F 1B                    DCX          D ; DECREMENT IT
3020 72                    MOV          M,D ; STORE IT
3021 2B                    DCX          H
3022 73                    MOV          M,E
3023 7A                    MOV          A,D ; SEE IF COUNTER IS 0
3024 B3                    ORA          E
3025 C24F30                JNZ          TQ03 ; NOT YET
3028                       SAVE         H
3029                       RESTOR       D ; POINT TO COUNTER
302A 23                    INX          H ; POINT TO RELOAD VALUE
302B 23                    INX          H
302C 7E                    MOV          A,M ; GET THE RELOAD VALUE
302D 12                    STAX         D
302E 4F                    MOV          C,A ; SAVE IT FOR THE 0 CHECK
302F 23                    INX          H
3030 13                    INX          D
3031 7E                    MOV          A,M
3032 12                    STAX         D
3033 B1                    ORA          C
3034 C23C30                JNZ          TQ04 ; IF THERE IS A RELOAD VALUE
3037                       RESTOR       H ; GET THE QUE LIST POINTER
3038                       SAVE         H
3039 77                    MOV          M,A ; ZERO IT
303A 2B                    DCX          H
303B 77                    MOV          M,A
303C            TQ04
303C 13                    INX          D ; POINT TO SUBROUTINE ADDRESS
303D 13                    INX          D
303E 13                    INX          D
303F 1A                    LDAX         D ; GET ADDRESS
3040 6F                    MOV          L,A ; PUT INTO 'HL'
3041 13                    INX          D
3042 1A                    LDAX         D
3043 67                    MOV          H,A
3044                       SAVEALL
3048 CD6130                CALL         INDRCT ; GOSUB (HL)
304B                       RESTALL      ; RESTORE ALL
304F            TQ03
304F                       RESTOR       H ; POINTER TO QUE LIST
3050            TQ02
3050 23                    INX          H ; POINT TO NEXT QUE ENTRY
3051 05                    DCR          B ; KEEP TRACK OF QUE ENTRIES
3052 C21130                JNZ          TQ01 ; IF MORE TO CHECK
3055 3AA2F8                LDA          NFINTRPT
3058 3D                    DCR          A
3059 32A2F8                STA          NFINTRPT
305C                       RESTALL
3060 C9                    RET
3061         ;***************************************************************************
3061         ;
3061                       USE          SYSTEM
3061         ;
3061         ;           INDIRECT ALLOWS AN INDIRECT SUBROUTINE CALL ON THE
3061         ;         HL REGISTER PAIR.
3061         ;              I.E.:   CALL INDRCT = CALL (HL)
3061         INDRCT
3061 E9                    PCHL         ; LOAD THE PC FROM THE MEMORY POINTED TO BY HL(A RET WORKS)
3062         ;***************************************************************************
3062         ;
3062                       USE          SYSTEM
3062         ;
3062         ;           QUEUE CHECKS THE TIMER QUE AND INSERTS THE CONTENTS
3062         ;         OF THE HL REGISTER PAIR IF A VACANT ENTRY IS FOUND.
3062            QUEUE
```

```
3062  CD8330           CALL     DEQUE
3065  0620             MVI      B,QSIZE ; GET THE QSIZE
3067  1100F0           LXI      D,QUELST ; POINT TO THE QUE
306A  EB               XCHG     ; PUT QUE PTR IN 'HL' AND SAVE CBLOCK PTR IN 'DE'
306B           IN01
306B  AF               XRA      A ; CLEAR A REGISTER
306C  B6               ORA      M ; SEE IF IT IS EMPTY
306D  23               INX      H
306E  B6               ORA      M
306F  CA7A30           JZ       STIKIT ; IF EMPTY
3072  23               INX      H ; POINT TO NEXT LOCATION
3073  05               DCR      B ; COUNT OF REMAINING LOCATIONS
3074  C26B30           JNZ      IN01 ; GO CHECK NEXT LOCATION
3077  EB               XCHG     ; PUT CBLOCK PTR INTO 'HL'
3078  37               STC      ; INDICATE NO ROOM
3079  C9               RET      ; IF NO ROOM
307A           ;
307A           STIKIT
307A  EB               XCHG     ; PUT QUE PTR INTO 'DE' AND CBLOCK PTR INTO 'HL'
307B  1B               DCX      D ; TO POINT TO FIRST BYTE
307C  7D               MOV      A,L ; GET ENTRY LO BYTE
307D  12               STAX     D ; STORE IT
307E  7C               MOV      A,H ; GET ENTRY HI BYTE
307F  13               INX      D
3080  12               STAX     D ; STORE IT
3081  A7               ANA      A ; CLEAR CARRY FLAG
3082  C9               RET
3083           ;***********************************************************
3083           ;
3083                    USE     SYSTEM
3083           ;
3083           ;        DEQUE REMOVES A TIMER QUE ENTRY
3083           ;   CARRY FLAG IS SET IF THE ENTRY IS NON-EXISTENT
3083           ;   'HL' CONTAINS THE CONTROL BLOCK ADDRESS
3083           ;
3083           DEQUE
3083  0E00             MVI      C,0
3085  0620             MVI      B,QSIZE
3087  1100F0           LXI      D,QUELST ; POINT TO QUE
308A  EB               XCHG     ; 'HL' => TO QUE
308B           DQ01
308B  7E               MOV      A,M ; CHECK AN ENTRY
308C  23               INX      H
308D  BB               CMP      E
308E  C29630           JNZ      DQ02 ; IF NOT A MATCH
3091  7E               MOV      A,M
3092  BA               CMP      D
3093  CAA130           JZ       DQ10 ; IF IT IS A MATCH
3096           DQ02
3096  23               INX      H
3097  05               DCR      B ; SEE IF DONE
3098  C28B30           JNZ      DQ01 ; NO
309B  EB               XCHG     ; PUT CBLOCK PTR INTO 'HL'
309C  79               MOV      A,C
309D  A7               ANA      A
309E  C0               RNZ
309F  37               STC      ; INDICATE NO SUCH ENTRY
30A0  C9               RET
30A1           ;
30A1           DQ10
30A1  AF               XRA      A ; CLEAR 'A'
30A2  77               MOV      M,A ; ZERO IT
30A3  2B               DCX      H
30A4  77               MOV      M,A
30A5  23               INX      H
30A6  0C               INR      C ; USED TO SET FLAG AT EXIT
30A7  C39630           JMP      DQ02 ; ZERO ALL ENTRIES FOR A CONTROL BLOCK
30AA           ;***********************************************************
30AA           ;
30AA                    USE     SYSTEM
30AA           ;
30AA           ;        RST 7.5 ROUTINE (KEYBOARD)
30AA           ;
30AA           ;
30AA           RST75
30AA                    SAVE    PSW
30AB  FB               EI
30AC                    RFIFO
30B1  DB0C             IN       KBDAT
30B3  321AF8           STA      CHAR
30B6                    RESTOR  PSW
30B7  C9               RET
30B8           ;***********************************************************
30B8           ;
30B8                    USE     SYSTEM
30B8           ;
30B8           ;        UNUSED INTERRUPT ROUTINE
30B8           UNUSED
30B8  FB               EI
30B9  C9               RET
30BA           ;***********************************************************
30BA           ;
30BA                    USE     SYSTEM
```

```
30BA           ;
30BA           ;
30BA           ;              UPDATE DISPLAY ROUTINE     * * * * * * * * *
30BA           ;
30BA           ;
30BA           DISPLAY
30BA           ;         POSITION 1, AUTO-INCREMENT
30BA                     WDRAM    0,1
30BF  2A00F8             LHLD     DSPTR1 ; GET POINTER TO POINTER TO RAM TO DISPLAY
30C2  5E                 MOV      E,M ; GET POINTER TO RAM TO DISPLAY
30C3  23                 INX      H
30C4  56                 MOV      D,M
30C5  1A                 LDAX     D ; GET A CHARACTER
30C6  D30C               OUT      KBDAT ; DISPLAY IT
30C8  13                 INX      D ; POINT TO NEXT BYTE
30C9  1A                 LDAX     D
30CA  D30C               OUT      KBDAT ; DISPLAY IT
30CC  13                 INX      D
30CD  1A                 LDAX     D
30CE  D30C               OUT      KBDAT ; DISPLAY IT
30D0  13                 INX      D
30D1  1A                 LDAX     D
30D2  D30C               OUT      KBDAT ; DISPLAY IT
30D4  13                 INX      D
30D5  1A                 LDAX     D
30D6  D30C               OUT      KBDAT ; DISPLAY IT
30D8  13                 INX      D
30D9  1A                 LDAX     D
30DA  D30C               OUT      KBDAT ; DISPLAY IT
30DC  13                 INX      D
30DD  1A                 LDAX     D
30DE  D30C               OUT      KBDAT ; DISPLAY IT
30E0  13                 INX      D
30E1  1A                 LDAX     D
30E2  D30C               OUT      KBDAT ; DISPLAY IT
30E4  C9                 RET
30E5           ;***********************************************************************
30E5           ;
30E5           ;         USE      SYSTEM
30E5           ;
30E5           ;              MAINTAINS 10 .1 SEC COUNT APPROXIMATELY EQUAL TO AVAILABLE
30E5           ;         PROCESSOR TIME.
30E5           ;
30E5           ;
30E5           UTILIZE
30E5  2A48F8             LHLD     COUNT1 ; RIPPLE THE COUNTS DOWN (FIFO)
30E8  2246F8             SHLD     COUNT0
30EB  2A4AF8             LHLD     COUNT2
30EE  2248F8             SHLD     COUNT1
30F1  2A4CF8             LHLD     COUNT3
30F4  224AF8             SHLD     COUNT2
30F7  2A4EF8             LHLD     COUNT4
30FA  224CF8             SHLD     COUNT3
30FD  2A50F8             LHLD     COUNT5
3100  224EF8             SHLD     COUNT4
3103  2A52F8             LHLD     COUNT6
3106  2250F8             SHLD     COUNT5
3109  2A54F8             LHLD     COUNT7
310C  2252F8             SHLD     COUNT6
310F  2A56F8             LHLD     COUNT8
3112  2254F8             SHLD     COUNT7
3115  2A58F8             LHLD     COUNT9
3118  2256F8             SHLD     COUNT8
311B  2A5AF8             LHLD     COUNTA ; GET CURRENT ACTIVE COUNT
311E  2258F8             SHLD     COUNT9
3121  210000             LXI      H,0 ; CLEAR ACTIVE COUNTER
3124  225AF8             SHLD     COUNTA
3127  C9                 RET
3128           ;***********************************************************************
3128           ;
3128           ;         USE      SYSTEM
3128           ;
3128           ;              CONVERT FROM A PERFECTLY GOOD PACKED DECIMAL NUMBER IN 'HL'
3128           ;         TO A DISPLAYABLE NUMBER POINTED TO BY 'BC'
3128           ;
3128           ;         PRVRT1 PRODUCES 1 DISPLAYABLE DIGIT
3128           ;         PRVRT2 PRODUCES 2 DISPLAYABLE DIGITS
3128           ;         PRVRT3 PRODUCES 3 DISPLAYABLE DIGITS
3128           ;         PRVRT4 PRODUCES 4 DISPLAYABLE DIGITS
3128           ;
3128           PRVRT1
3128                     SAVE     PSW
3129  C34D31             JMP      PRVRT7
312C           ;
312C           PRVRT2
312C                     SAVE     PSW
312D  C34631             JMP      PRVRT6
3130           ;
3130           PRVRT3
3130                     SAVE     PSW
3131  C33C31             JMP      PRVRT5
3134           ;
```

```
3134                PRVRT4
3134                          SAVE      PSW
3135   7D                     MOV       A,L ; GET THE HI BYTE
3136   E6F0                   ANI       0F0H ; JUST THE HI NIBBLE
3138   C610                   ADI       010H ; TO DISPLAYABLE
313A   02                     STAX      B ; SAVE IT
313B   03                     INX       B
313C                ;
313C                PRVRT5
313C   7D                     MOV       A,L ; GET THE HI BYTE
313D   E60F                   ANI       00FH ; JUST THE LO NIBBLE
313F   3C                     INR       A ; TO DISPLAYABLE
3140   07                     RLC
3141   07                     RLC
3142   07                     RLC
3143   07                     RLC
3144   02                     STAX      B ; SAVE IT
3145   03                     INX       B
3146                ;
3146                PRVRT6
3146   7C                     MOV       A,H ; GET THE LO BYTE
3147   E6F0                   ANI       0F0H ; JUST THE HI NIBBLE
3149   C610                   ADI       010H ; TO DISPLAYABLE
314B   02                     STAX      B
314C   03                     INX       B
314D                ;
314D                PRVRT7
314D   7C                     MOV       A,H ; GET THE LO BYTE
314E   E60F                   ANI       00FH ; JUST THE LO NIBBLE
3150   3C                     INR       A ; TO DISPLAYABLE
3151   07                     RLC
3152   07                     RLC
3153   07                     RLC
3154   07                     RLC
3155   02                     STAX      B ; SAVE IT
3156                          RESTOR    PSW
3157   C9                     RET
3158                ;************************************************************
3158                ;
3158                          USE       SYSTEM
3158                ;
3158                ;         CONVERT THE DISPLAYABLE CHARACTERS POINTED TO BY 'BC' TO
3158                ;         PACKED DECIMAL IN 'HL'
3158                ;
3158                ;         CNVRT1 TO CONVERT 1 DIGIT
3158                ;         CNVRT2 TO CONVERT 2 DIGITS
3158                ;         CNVRT3 TO CONVERT 3 DIGITS
3158                ;         CNVRT4 TO CONVERT 4 DIGITS
3158                ;
3158                CNVRT1
3158   210000                 LXI       H,0
315B   C37E31                 JMP       CNVRT7
315E                CNVRT2
315E   210000                 LXI       H,0
3161   C37931                 JMP       CNVRT6
3164                CNVRT3
3164   210000                 LXI       H,0
3167   C36F31                 JMP       CNVRT5
316A                CNVRT4
316A   0A                     LDAX      B ; GET A CHARACTER
316B   DE10                   SBI       010H ; TO A BINARY HI NIBBLE
316D   6F                     MOV       L,A ; SAVE IT
316E   03                     INX       B
316F                CNVRT5
316F   0A                     LDAX      B ; GET A CHARACTER
3170   DE10                   SBI       010H ; TO A BINARY LO NIBBLE
3172   0F                     RRC
3173   0F                     RRC
3174   0F                     RRC
3175   0F                     RRC
3176   B5                     ORA       L ; GET THE HI NIBBLE
3177   6F                     MOV       L,A ; SAVE IT
3178   03                     INX       B
3179                CNVRT6
3179   0A                     LDAX      B ; GET A CHARACTER
317A   DE10                   SBI       010H ; TO A BINARY HI NIBBLE
317C   67                     MOV       H,A ; SAVE IT
317D   03                     INX       B
317E                CNVRT7
317E   0A                     LDAX      B ; GET A CHARACTER
317F   DE10                   SBI       010H ; TO A BINARY LO NIBBLE
3181   0F                     RRC
3182   0F                     RRC
3183   0F                     RRC
3184   0F                     RRC
3185   B4                     ORA       H ; GET THE HI NIBBLE
3186   67                     MOV       H,A ; SAVE IT
3187   C9                     RET
3188                ;************************************************************
3188                ;
3188                          USE       SYSTEM
3188                ;
```

```
3188                    ;           ROUTINE TO CONVERT A PACKED DECIMAL NUMBER IN 'HL' INTO
3188                    ;           BINARY.
3188                    ;
3188            PK2BIN
3188                    SAVE        PSW,D,B
318B  EB              XCHG        ; PUT # INTO 'DE'
318C  7B              MOV         A,E ; GET THE HI BYTE
318D  210000          LXI         H,0 ; INITIALIZE
3190  07              RLC
3191  D29831          JNC         PB01
3194  01401F          LXI         B,8000
3197  09              DAD         B
3198            PB01
3198  07              RLC
3199  D2A031          JNC         PB02
319C  01A00F          LXI         B,4000
319F  09              DAD         B
31A0            PB02
31A0  07              RLC
31A1  D2A831          JNC         PB03
31A4  01D007          LXI         B,2000
31A7  09              DAD         B
31A8            PB03
31A8  07              RLC
31A9  D2B031          JNC         PB04
31AC  01E803          LXI         B,1000
31AF  09              DAD         B
31B0            PB04
31B0  07              RLC
31B1  D2B831          JNC         PB05
31B4  012003          LXI         B,800
31B7  09              DAD         B
31B8            PB05
31B8  07              RLC
31B9  D2C031          JNC         PB06
31BC  019001          LXI         B,400
31BF  09              DAD         B
31C0            PB06
31C0  07              RLC
31C1  D2C831          JNC         PB07
31C4  01C800          LXI         B,200
31C7  09              DAD         B
31C8            PB07
31C8  07              RLC
31C9  D2D031          JNC         PB08
31CC  016400          LXI         B,100
31CF  09              DAD         B
31D0            PB08
31D0  7A              MOV         A,D ; GET LO BYTE
31D1  07              RLC
31D2  D2D931          JNC         PB09
31D5  015000          LXI         B,80
31D8  09              DAD         B
31D9            PB09
31D9  07              RLC
31DA  D2E131          JNC         PB10
31DD  012800          LXI         B,40
31E0  09              DAD         B
31E1            PB10
31E1  07              RLC
31E2  D2E931          JNC         PB11
31E5  011400          LXI         B,20
31E8  09              DAD         B
31E9            PB11
31E9  07              RLC
31EA  D2F131          JNC         PB12
31ED  010A00          LXI         B,10
31F0  09              DAD         B
31F1            PB12
31F1  07              RLC
31F2  D2F931          JNC         PB13
31F5  010800          LXI         B,8
31F8  09              DAD         B
31F9            PB13
31F9  07              RLC
31FA  D20132          JNC         PB14
31FD  010400          LXI         B,4
3200  09              DAD         B
3201            PB14
3201  07              RLC
3202  D20932          JNC         PB15
3205  010200          LXI         B,2
3208  09              DAD         B
3209            PB15
3209  07              RLC
320A  D21132          JNC         PB16
320D  010100          LXI         B,1
3210  09              DAD         B
3211            PB16
3211                    RESTOR      B,D,PSW
3214  C9              RET
3215                    ;************************************************************************
3215                    ;
```

```
3215                         USE         SYSTEM
3215              ;
3215              ;              BINARY TO PACKED DECIMAL
3215              ;     'HL' CONTAINS THE BINARY NUMBER TO CONVERT
3215              ;
3215              BIN2PK
3215                         SAVE        PSW,B,D
3218  11E803                 LXI         D,1000
321B  0118FC                 LXI         B,(("1000)+1)
321E  CD4B32                 CALL        DIGIT
3221  07                     RLC
3222  07                     RLC
3223  07                     RLC
3224  07                     RLC
3225  5F                     MOV         E,A
3226  1600                   MVI         D,0
3228                         SAVE        D
3229  116400                 LXI         D,100
322C  019CFF                 LXI         B,(("100)+1)
322F  CD4B32                 CALL        DIGIT
3232                         RESTOR      D
3233  B3                     ORA         E
3234  5F                     MOV         E,A
3235                         SAVE        D
3236  110A00                 LXI         D,10
3239  01F6FF                 LXI         B,(("10)+1)
323C  CD4B32                 CALL        DIGIT
323F  07                     RLC
3240  07                     RLC
3241  07                     RLC
3242  07                     RLC
3243  B5                     ORA         L
3244  67                     MOV         H,A
3245                         RESTOR      D
3246  6B                     MOV         L,E
3247                         RESTOR      D,B,PSW
324A  C9                     RET
324B              ;
324B              DIGIT
324B  AF                     XRA         A ; CLEAR 'A'
324C              DG01
324C  A7                     ANA         A ; CLEAR CARRY
324D  09                     DAD         B ; ADD 2'S COMPLEMENT TO 'HL'
324E  D25532                 JNC         DG02 ; IF DONE
3251  3C                     INR         A ; ELSE, KEEP TRACK OF DIGIT
3252  C34C32                 JMP         DG01 ; GO DO AGAIN
3255              DG02
3255  19                     DAD         D ; ABOVE ROUTINE WILL SUBTRACT 1 TO MANY
3256  C9                     RET
3257              ;*********************************************************
3257                         USE         SYSTEM
3257              ;
3257              ;              UPDATE THE LED INDICATOR LIGHTS
3257              ;
3257              ;
3257              LEDUPD
3257  3A00E0                 LDA         A1ST
325A  D300                   OUT         A1
325C  3A01E0                 LDA         B1ST
325F  D301                   OUT         B1
3261  3A02E0                 LDA         C1ST
3264  D302                   OUT         C1
3266  C9                     RET
3267              ;*********************************************************
3267              ;
3267                         USE         SYSTEM
3267              ;
3267              ;        VALIDATE A COMMAND AND RETURN A SUBROUTINE ADDRESS IF VALID
3267              ;     SET THE CARRY FLAG OTHERWISE.
3267              ;              'HL' => TABLE OF LEGAL COMMANDS
3267              ;              'DE' => TABLE OF ROUTINE ADDRESSES
3267              ;              'B'  = # OF COMMANDS
3267              ;              'A'  = COMMAND KEY VALUE
3267              ;     ON RETURN:
3267              ;              'HL' => ROUTINE
3267              ;              CARRY SET IF INVALID COMMAND
3267              ;              CARRY CLEAR IF VALID
3267              ;
3267              COMMD
3267  BE                     CMP         M ; SEE IF THIS COMMAND
3268  CA7432                 JZ          CM01 ; YES, A MATCH
326B  23                     INX         H ; ELSE ...
326C  13                     INX         D
326D  13                     INX         D
326E  05                     DCR         B ; KEEP TRACK OF THE # OF COMMANDS
326F  C26732                 JNZ         COMMD ; IF MORE TO CHECK
3272  37                     STC         ; SET CARRY TO INDICATE INVALID
3273  C9                     RET
3274              CM01
3274                         SAVE        PSW
3275  1A                     LDAX        D ; PUT THE SUBROUTINE ADDRESS INTO 'HL'
3276  6F                     MOV         L,A
```

```
3277  13                      INX        D
3278  1A                      LDAX       D
3279  67                      MOV        H,A
327A                          RESTOR     PSW
327B  A7                      ANA        A ; CLEAR CARRY TO INDICATE VALID
327C  C9                      RET
327D            ;*********************************************************************
327D            ;
327D                          USE        SYSTEM
327D            ;
327D            ;             CHECK TO SEE IF THE CHARACTER IN 'A' IS A VALID KEYBOARD
327D            ;      NUMERAL.
327D            ;             CARRY FLAG SET IF NOGOOD
327D            ;             CARRY FLAG CLEAR IF GOOD
327D            ;             'A' = THE BINARY CONVERSION IF GOOD
327D            ;
327D  D0D1D2C0  NUMS          DB         0D0H,0D1H,0D2H,0C0H,0C1H,0C2H,0F0H,0F1H,0F2H,0E9H
      C1C2F0F1
      F2E9
3287            KB2BIN
3287                          SAVE       H,B
3289  0609                    MVI        B,9 ; START AT 9 AND WORK DOWN
328B  217D32                  LXI        H,NUMS ; POINT TO TABLE OF NUMERALS
328E            KB01
328E  BE                      CMP        M ; SEE IF A MATCH
328F  CA9B32                  JZ         KB02 ; IF A MATCH
3292  23                      INX        H ; POINT TO NEXT VALUE
3293  05                      DCR        B ; COUNT OF DIGITS
3294  F28E32                  JP         KB01 ; GO CHECK ANOTHER
3297  37                      STC        ; IF NOT FOUND
3298                          RESTOR     B,H
329A  C9                      RET
329B            KB02
329B  78                      MOV        A,B ; PUT BINARY CONVERSION INTO 'A'
329C                          RESTOR     B,H
329E  B7                      ORA        A ; CLEAR CARRY
329F  C9                      RET
32A0            ;*********************************************************************
32A0            ;
32A0                          USE        SYSTEM
32A0            ;
32A0            ;             CHECK TO SEE IF THE CHARACTER IN 'A' IS A VALID BINARY
32A0            ;      NUMERAL. IF SO, CONVERT TO DISPLAYABLE.
32A0            ;             'A' = THE DISPLAYABLE CONVERSION
32A0            ;
32A0            BIN2DS
32A0  FE0A                    CPI        10
32A2  F2AC32                  JP         BD01 ; IF ILLEGAL
32A5  3C                      INR        A
32A6  07                      RLC
32A7  07                      RLC
32A8  07                      RLC
32A9  07                      RLC
32AA  B7                      ORA        A ; CLEAR CARRY FLAG
32AB  C9                      RET
32AC            BD01
32AC  37                      STC        ; INDICATE INVALID
32AD  C9                      RET
32AE            ;*********************************************************************
32AE            ;
32AE                          USE        SYSTEM
32AE            ;
32AE            ;             CONVERT THE DISPLAYABLE NUMERAL IN 'A' INTO A BINARY
32AE            ;      NUMBER.
32AE            ;             CARRY FLAG SET IF NO GOOD
32AE            ;             CARRY FLAG CLEAR IF GOOD
32AE            ;             'A' = THE BINARY CONVERSION
32AE            ;
32AE            DS2BIN
32AE  0F                      RRC
32AF  0F                      RRC
32B0  0F                      RRC
32B1  0F                      RRC
32B2  3D                      DCR        A
32B3  FE0A                    CPI        10 ; SEE IF VALID
32B5  F2BA32                  JP         DB01 ; IF INVALID
32B8  B7                      ORA        A ; CLEAR CARRY
32B9  C9                      RET
32BA            DB01
32BA  37                      STC        ; INDICATE NO GOOD
32BB  C9                      RET
32BC            ;*********************************************************************
32BC            ;
32BC            ;             INTEGER MULTIPLY ROUTINE
32BC            ;      ARGUMENTS:
32BC            ;             'BC' IS THE MULTIPLICAND
32BC            ;             'DE' IS THE MULTIPLIER
32BC            ;      RETURNS:
32BC            ;             'HLDE' IS THE PRODUCT
32BC            ;
32BC            I4MULT
32BC                          SAVE       PSW
```

```
32BD                            ;               BIT COUNTER
32BD    3E10                    MVI     A,16
32BF    210000                  LXI     H,0
32C2                            SAVE    H
32C3            I4M01
32C3                    ;       SHIFT THE 32 BIT PRODUCT LEFT 1 BIT
32C3                            DRLC    H
32C4    E3                      XTHL
32C5                            DRLC    H
32C6    E3                      XTHL
32C7    D2CB32                  JNC     I4M02
32CA    23                      INX     H
32CB            I4M02
32CB                    ;       SHIFT THE MULTIPLIER LEFT 1 BIT
32CB                            DRLC    D
32CE    D2D832                  JNC     I4M03 ; IF NO CARRY
32D1    E3                      XTHL          ; ELSE, ADD TO PRODUCT
32D2    09                      DAD     B
32D3    E3                      XTHL
32D4    D2D832                  JNC     I4M03
32D7    23                      INX     H
32D8            I4M03
32D8                    ;       KEEP TRACK OF NUMBER OF BITS
32D8    3D                      DCR     A
32D9    C2C332                  JNZ     I4M01 ; IF MORE TO DO
32DC                            RESTOR  D,PSW
32DE    C9                      RET
32DF    ;************************************************************
32DF            ;
32DF            ;               INTEGER DIVISION ROUTINE
32DF            ;       ARGUMENTS:
32DF            ;               'HLDE' CONTAINS THE DIVIDEND
32DF            ;               'BC'   CONTAINS THE DIVISOR
32DF            ;       RETURNS:
32DF            ;               'DE' IS THE QUOTIENT
32DF            ;               'HL' IS THE REMAINDER
32DF            ;               'DE' WILL CONTAIN 'FFFF' IF OVERFLOW
32DF            ;
32DF            I4DIVD
32DF                            SAVE    PSW,B
32E1                    ;       2'S COMPLEMENT THE DIVISOR
32E1    79                      MOV     A,C
32E2    2F                      CMA
32E3    4F                      MOV     C,A
32E4    78                      MOV     A,B
32E5    2F                      CMA
32E6    47                      MOV     B,A
32E7    03                      INX     B
32E8                    ;       BIT COUNT
32E8    3E10                    MVI     A,16
32EA            I4D01
32EA                    ;       SHIFT 32 BIT DIVIDEND LEFT 1 BIT
32EA                            DRLC    H
32EB                            DRLC    D
32EE    D2F232                  JNC     I4D02
32F1    23                      INX     H
32F2            I4D02
32F2                    ;       SEE IF DIVISOR IS > 16 MSB'S OF DIVIDEND
32F2                            SAVE    H
32F3    09                      DAD     B
32F4    D2F932                  JNC     I4D03 ; YES, GO RESTORE DIVEDEND
32F7    13                      INX     D ; ELSE, INCREMENT QUOTIENT
32F8    E3                      XTHL      ; AND PUT NEW DIVIDEND ON STACK
32F9            I4D03
32F9                            RESTOR  H ; RESTORE DIVIDEND
32FA    3D                      DCR     A ; KEEP TRACK OF NUMBER OF BITS
32FB    C2EA32                  JNZ     I4D01 ; IF MORE TO DO
32FE                            RESTOR  B,PSW
3300    C9                      RET
3301    ;************************************************************
3301            ;
3301            DUMMY
3301    FB                      EI
3302    C9                      RET
3303    ;************************************************************
3303            ;
3303            MSEC
3303                            SAVEALL
3307    3A9DF8                  LDA     T.IMAGE ; GET IMAGE OF TIMER
330A    E6F9                    ANI     "(T.TRGR+T.INTE) ; CLEAR INTERUPT ENABLE AND TRIGGER BITS
330C    329DF8                  STA     T.IMAGE ; SAVE IMAGE
330F    D334                    OUT     TIM.PIA
3311    FB                      EI
3312    2A96F8                  LHLD    TNEXT ; GET NEXT ROUTINE TO EXECUTE
3315    CD6130                  CALL    INDRCT
3318                            RESTALL
331C    C9                      RET
331D    ;************************************************************
331D            RAMP
331D                            SAVEALL
3321    3A9CF8                  LDA     P.IMAGE ; GET IMAGE
3324    E6CB                    ANI     "(P.TRGR+P.INTE+P.UPDN) ; CLEAR INTERUPT ENABLE AND TRIGGER BITS
3326    329CF8                  STA     P.IMAGE ; SAVE IMAGE
```

```
3329  D32A              OUT       PRB.PIA+2
332B  FB                EI
332C  2A98F8            LHLD      RNEXT ; GET NEXT ROUTINE TO EXECUTE
332F  CD6130            CALL      INDRCT
3332                    RESTALL
3336  C9                RET
3337           ;**********************************************************************
3337           BOOST
3337                    SAVEALL
333B  3A9CF8            LDA       P.IMAGE ; GET IMAGE
333E  E677              ANI       "(B.INTE+B.TRGR)
3340  329CF8            STA       P.IMAGE ; SAVE IMAGE
3343  D32A              OUT       PRB.PIA+2
3345  FB                EI
3346  2A9AF8            LHLD      BNEXT ; GET NEXT ROUTINE
3349  CD6130            CALL      INDRCT
334C                    RESTALL
3350  C9                RET
3351           ;**********************************************************************
3351           BEEP1
3351                    SAVEALL
3355  3A03E0            LDA       A2ST
3358  F603              ORI       BEEP.1
335A  3203E0            STA       A2ST
335D                    TIMER     1,0,BEEP,CBLK17
3375                    RESTALL
3379  C9                RET
337A           BEEP2
337A                    SAVEALL
337E  3A03E0            LDA       A2ST
3381  F605              ORI       BEEP.2
3383  3203E0            STA       A2ST
3386                    TIMER     1,0,BEEP,CBLK17
339E                    RESTALL
33A2  C9                RET
33A3           BEEP3
33A3                    SAVEALL
33A7  3A03E0            LDA       A2ST
33AA  F609              ORI       BEEP.3
33AC  3203E0            STA       A2ST
33AF                    TIMER     1,0,BEEP,CBLK17
33C7                    RESTALL
33CB  C9                RET
33CC           BEEP
33CC  3A03E0            LDA       A2ST
33CF  D304              OUT       A2
33D1                    TIMER     1,0,KILLBEEP,CBLK17
33E9  C9                RET
33EA           KILLBEEP
33EA  3A03E0            LDA       A2ST
33ED  E6F0              ANI       0F0H
33EF  3203E0            STA       A2ST
33F2  D304              OUT       A2
33F4  C9                RET
33F5           ;**********************************************************************
33F5                    END
33F5           ;**********************************************************************
33F5           ;
33F5                    USE       SYSTEM
33F5           ;
33F5           ; INTEGER MULTIPLY
33F5           ; HL=HL*DE
33F5           IMULT
33F5  C5                PUSH      B
33F6  F5                PUSH      PSW
33F7  44                MOV       B,H ; RETURNS HL=HL*DE
33F8  4D                MOV       C,L
33F9  210000            LXI       H,0
33FC           IM01
33FC  79                MOV       A,C
33FD  1F                RAR
33FE  D20234            JNC       IM02
3401  19                DAD       D
3402           IM02
3402  B7                ORA       A
3403  78                MOV       A,B
3404  1F                RAR
3405  47                MOV       B,A
3406  79                MOV       A,C
3407  1F                RAR
3408  4F                MOV       C,A
3409  B0                ORA       B
340A  C21034            JNZ       IM03
340D  F1                POP       PSW
340E  C1                POP       B
340F  C9                RET
3410           IM03
3410  EB                XCHG
3411  29                DAD       H
3412  EB                XCHG
3413  C3FC33            JMP       IM01
3416           ;***********************************text
```

```
3416                VIN
3416                ;CALLING THIS ROUTINE READS ALL INPUT VOLTAGES AND STORES
3416                ;THEM IN CH1IN-CH8HIN(10 BITS, STORED LOW , HIGH)
3416  E5                        PUSH     H
3417  D5                        PUSH     D
3418  C5                        PUSH     B
3419  F5                        PUSH     PSW
341A  0680                      MVI      B,80H
341C  210000                    LXI      H,0
341F                VINLP
341F  78                        MOV      A,B
3420  D610                      SUI      10H
3422  47                        MOV      B,A
3423  CD7C34                    CALL     MULTPLX
3426  CDDF34                    CALL     MATOD
3429  CD3534                    CALL     STORE
342C  78                        MOV      A,B
342D  FE00                      CPI      0
342F  CA8334                    JZ       EXIT
3432  C31F34                    JMP      VINLP
3435  78          STORE         MOV      A,B
3436  FE70                      CPI      70H
3438  CA5C34                    JZ       CH1ST
343B  FE60                      CPI      60H
343D  CA6034                    JZ       CH2ST
3440  FE50                      CPI      50H
3442  CA6434                    JZ       CH3ST
3445  FE40                      CPI      40H
3447  CA6834                    JZ       CH4ST
344A  FE30                      CPI      30H
344C  CA6C34                    JZ       CH5ST
344F  FE20                      CPI      20H
3451  CA7034                    JZ       CH6ST
3454  FE10                      CPI      10H
3456  CA7434                    JZ       CH7ST
3459  C37834                    JMP      CH8ST
345C  2209E0      CH1ST         SHLD     CH1IN
345F  C9                        RET
3460  220BE0      CH2ST         SHLD     CH2IN
3463  C9                        RET
3464  220DE0      CH3ST         SHLD     CH3IN
3467  C9                        RET
3468  220FE0      CH4ST         SHLD     CH4IN
346B  C9                        RET
346C  2211E0      CH5ST         SHLD     CH5IN
346F  C9                        RET
3470  2213E0      CH6ST         SHLD     CH6IN
3473  C9                        RET
3474  2215E0      CH7ST         SHLD     CH7IN
3477  C9                        RET
3478  2217E0      CH8ST         SHLD     CH8IN
347B  C9                        RET
347C  3A06E0      MULTPLX       LDA      A3ST
347F  B0                        ORA      B
3480  D308                      OUT      A3
3482  C9                        RET
3483  F1          EXIT          POP      PSW
3484  C1                        POP      B
3485  D1                        POP      D
3486  E1                        POP      H
3487  C9                        RET
3488                ;************************************
3488                VOUT
3488                ;CALLING THIS ROUTINE SENDS CH1OUT-CH8OUT TO THE SAMPLE&HOLDS
3488  E5                        PUSH     H
3489  D5                        PUSH     D
348A  C5                        PUSH     B
348B  F5                        PUSH     PSW
348C  2A19E0                    LHLD     CH1OUT
348F  0E01                      MVI      C,1
3491  CDCF34                    CALL     SENDV
3494  2A1BE0                    LHLD     CH2OUT
3497  0E02                      MVI      C,2
3499  CDCF34                    CALL     SENDV
349C  2A1DE0                    LHLD     CH3OUT
349F  0E04                      MVI      C,4
34A1  CDCF34                    CALL     SENDV
34A4  2A1FE0                    LHLD     CH4OUT
34A7  0E08                      MVI      C,8
34A9  CDCF34                    CALL     SENDV
34AC  2A21E0                    LHLD     CH5OUT
34AF  0E10                      MVI      C,10H
34B1  CDCF34                    CALL     SENDV
34B4  2A23E0                    LHLD     CH6OUT
34B7  0E20                      MVI      C,20H
34B9  CDCF34                    CALL     SENDV
34BC  2A25E0                    LHLD     CH7OUT
34BF  0E40                      MVI      C,40H
34C1  CDCF34                    CALL     SENDV
34C4  2A27E0                    LHLD     CH8OUT
34C7  0E80                      MVI      C,80H
34C9  CDCF34                    CALL     SENDV
34CC  C38334                    JMP      EXIT
```

```
34CF  7C        SENDV   MOV    A,H
34D0  D306              OUT    C2
34D2  3205E0            STA    C2ST
34D5  7D                MOV    A,L
34D6  D305              OUT    B2
34D8  3204E0            STA    B2ST
34DB  CD9335            CALL   SAMPL
34DE  C9                RET
34DF            ;************************************
34DF            ; THIS IS THE MAIN SUCCESSIVE APPROXIMATION A TO D ROUTINE
34DF            ; 10 BIT CONVERSION IS MATOD
34DF            ; 8 BIT CONVERSION IS ATOD8
34DF            ; THIS PROGRAM RETURNS A VALUE IN DACVH (HIGH BYTE) AND DACVL (LOW BYTE)
34DF            ; WHICH EQUALS THE VALUE OF THE VOLTAGE PRESENT AT THE 710 COMPARATOR INPUT
34DF            ; IN INCREMENTS OF 10 MV. 100 = 1 VOLT
34DF            MATOD   ENTRY
34DF  AF                XRA    A ; SETS DAC TO 0 VOLTS
34E0  D305              OUT    B2
34E2  D306              OUT    C2
34E4  67                MOV    H,A
34E5  3E02              MVI    A,2 ; TRY MOST SIGNIFICANT BIT FIRST - SET MSB DAC ON
34E7  D306              OUT    C2
34E9  CD6935            CALL   J2
34EC  CAF234            JZ     SA100
34EF  3E02              MVI    A,2
34F1  67                MOV    H,A
34F2  7C        SA100   MOV    A,H
34F3  F601              ORI    1
34F5  CD6935            CALL   J2
34F8  CAFF34            JZ     ATOD8
34FB  7C                MOV    A,H
34FC  F601              ORI    1
34FE  67                MOV    H,A
34FF  AF        ATOD8   XRA    A
3500  6F                MOV    L,A
3501  7C                MOV    A,H
3502  D306              OUT    C2
3504  3E80              MVI    A,80H
3506  CD7135            CALL   J1
3509  CA0F35            JZ     SA40
350C  3E80              MVI    A,80H
350E  6F                MOV    L,A
350F  7D        SA40    MOV    A,L
3510  F640              ORI    40H
3512  CD7135            CALL   J1
3515  CA1C35            JZ     SA20
3518  7D                MOV    A,L
3519  F640              ORI    40H
351B  6F                MOV    L,A
351C  7D        SA20    MOV    A,L
351D  F620              ORI    20H
351F  CD7135            CALL   J1
3522  CA2935            JZ     SA10
3525  7D                MOV    A,L
3526  F620              ORI    20H
3528  6F                MOV    L,A
3529  7D        SA10    MOV    A,L
352A  F610              ORI    10H
352C  CD7135            CALL   J1
352F  CA3635            JZ     SA8
3532  7D                MOV    A,L
3533  F610              ORI    10H
3535  6F                MOV    L,A
3536  7D        SA8     MOV    A,L
3537  F608              ORI    8
3539  CD7135            CALL   J1
353C  CA4335            JZ     SA4
353F  7D                MOV    A,L
3540  F608              ORI    8
3542  6F                MOV    L,A
3543  7D        SA4     MOV    A,L
3544  F604              ORI    4
3546  CD7135            CALL   J1
3549  CA5035            JZ     SA2
354C  7D                MOV    A,L
354D  F604              ORI    4
354F  6F                MOV    L,A
3550  7D        SA2     MOV    A,L
3551  F602              ORI    2
3553  CD7135            CALL   J1
3556  CA5D35            JZ     SA1
3559  7D                MOV    A,L
355A  F602              ORI    2
355C  6F                MOV    L,A
355D  7D        SA1     MOV    A,L
355E  F601              ORI    1
3560  CD7135            CALL   J1
3563  C8                RZ     ;
3564  7D                MOV    A,L
3565  F601              ORI    1
3567  6F                MOV    L,A
3568  C9                RET
3569  D306      J2      OUT    C2 ; SEND DATA TO DAC UPPER BITS
```

```
356B  3205E0              STA     C2ST ; AND STORE IMAGE
356E  C37635              JMP     J12 ; AND DO SAME FOR LOWER BITS
3571  D305        J1      OUT     B2 ; SEND DATA TO LOWER BITS
3573  3204E0              STA     B2ST ; SAVE IT
3576  CD8035      J12     CALL    WAIT ; DELAY FOR 710 & DAC TO SETTLE
3579  DB06                IN      C2 ; GET 710 OUTPUT
357B  E610                ANI     EQUAL
357D  FE00                CPI     0 ; IS IT ZERO
357F  C9                  RET
3580                      ;****************************
3580              WAIT    ENTRY
3580  E5                  PUSH    H ; THIS SUBROUTINE WAITS FOR THE DAC & 710 TO SETTLE OUT
3581  210700              LXI     H,7 ; PRESET COUNTER
3584  2B          WAITLP2 DCX     H ; DECREMENT IT & IF NOT = 0 THEN LOOP AGAIN ELSE ALL DONE
3585  7C                  MOV     A,H
3586  FE00                CPI     0
3588  C28435              JNZ     WAITLP2
358B  7D                  MOV     A,L
358C  FE00                CPI     0
358E  C28435              JNZ     WAITLP2
3591  E1                  POP     H
3592  C9                  RET
3593                      ;****************************
3593              SAMPL   ENTRY   ; THIS OUTPUTS THE SAMPLE MUX CODE TO THE SAMPLE & HOLDS
3593                      ; FOR ABOUT 200 MICROSECONDS TO ENABLE THE SAMPLE AND HOLDS
3593  79                  MOV     A,C
3594  D309                OUT     B3 ; TURN ON SAMPLE
3596  CD8035              CALL    WAIT
3599  AF                  XRA     A
359A  D309                OUT     B3 ; TURNS OFF SAMPLE
359C  C9                  RET
359D                      ;*********************************************************
359D                      END
359D                      ;*********************************************************
359D                      ;
359D                      USE     PRGM
8000                      ;           MAIN ROUTINE        * * * * * * * *
8000                      ;
8000                      ;
8000              INITAL  ENTRY
8000  C34D80              JMP     INIT00
8003                      ;
8003              MAIN    ENTRY
8003  C37F80              JMP     MAIN00
8006                      ;
8006  D0E0A200    CDSMSG  DB      CCODE,DCODE,SCODE,BLANK,CODE1,CODE0,CODE0,CODE0
      20101010
800E  C9E5DDD7    COMMDS  DB      KY.DTCLK,KY.INIT,KY.RAMP1,KY.HOLD1,KY.RAMP2,KY.FINAL,KY.MTHR
      D6D5F4
8015  ECE4DCEF            DB      KY.MTHS,KY.START,KY.STOP,KY.HOLD,KY.RESUM,KY.DUMP,KY.INPT,KY.OUTPT
      EEF7DBE3
801D  C7DA                DB      KY.CAL,KY.GCF
801F  E0850060    ROUTNS  DW      DTECLK,SRINT,SRMP1,SRHD1,SRMP2,SRFNL,SRMRCL,SRMSTR
      03600660
      09600C60
      BA8A338A
802F  A682E782            DW      SRSTRT,SRSTOP,SRHOLD,SRRESM,SRDUMP,SRINP,SROUT
      00835583
      538BD28C
      658C
803D  358D3A8E            DW      SRCAL,SRGCF
0011              NCOMDS  EQU     ROUTNS-COMMDS
8041  31283130    INDAY   DB      031H,028H,031H,030H,031H,030H,031H,031H,030H,031H,030H,031H
      31303131
      30313031
804D                      ;
804D              INIT00  ENTRY
804D  F3                  DI
804E  3E0B                MVI     A,11 ; MASK RST 5.5 AND 6.5
8050                      SIM
8051  3E99                MVI     A,10011001B
8053  D313                OUT     13H
8055  3E80                MVI     A,10000000B ; ALL OUTPUTS
8057  D303                OUT     X1
8059  3E88                MVI     A,10001000B ; C4-C7 INPUTS, REST OUTPUTS
805B  D307                OUT     X2
805D  3E80                MVI     A,10000000B ; ALL OUTPUTS
805F  D30B                OUT     X3
8061  AF                  XRA     A
8062  D30D                OUT     KBCNT
8064  3E32                MVI     A,00110010B
8066  D30D                OUT     KBCNT
8068  3EA0                MVI     A,10100000B
806A  D30D                OUT     KBCNT
806C                      CLEAR   1,1,1,LOOP1
8077  3E40                MVI     A,01000000B
8079  D30D                OUT     KBCNT
807B  3E92                MVI     A,10010010B
807D  D30D                OUT     KBCNT
807F                      ;
807F              MAIN00  ENTRY
807F  F3                  DI              ; KILL INTERUPTS
8080                      ;       KILL TRAP INTERUPTS
8080  3A03E0              LDA     A2ST ; GET PORT IMAGE
```

```
8083  E6EF              ANI        "PREAD ; CLEAR PROCESSOR READY
8085  3203E0            STA        A2ST
8088  D304              OUT        A2
808A            ;            SET TOP OF STACK
808A  3100E4            LXI        SP,STACK
808D            ;            SET UP HARDWARE
808D                    INPIC      ; INITIALIZE PROGRAMMABLE INTERUPT CONTROLLER
8098                    INPROB     ; INITIALIZE PROBE HARDWARE
80B7                    INTIME     ; INITIALIZE TIMER HARDWARE
80D8            ;            CLEAR RAM IF NEEDED
80D8            ;
80D8  3A00C8            LDA        CONDIT1 ; GET FIRST BYTE OF MEMORY CONDITION FLAG
80DB  2100D0            LXI        H,CONDIT2 ; POINT TO 2ND MEMORY CONDITION FLAG
80DE  AE                XRA        M
80DF  FEFF              CPI        0FFH ; SEE IF GARBAGE
80E1  CAEA80            JZ         MAIN00.5 ; IF IT IS GOOD
80E4  2100C8            LXI        H,0C800H ; ELSE, POINT TO START OF RAM
80E7  C3ED80            JMP        MAIN00.7
80EA          MAIN00.5
80EA  2100E0            LXI        H,0E000H
80ED          MAIN00.7
80ED  3600              MVI        M,0
80EF  23                INX        H ; CLEAR, CLEAR, CLEAR, CLEAR
80F0  7D                MOV        A,L
80F1  B4                ORA        H
80F2  C2ED80            JNZ        MAIN00.7 ; TO LOCATION 'FFFF'
80F5            ;            SET THE MEMORY CONDITION FLAGS
80F5  3EAA              MVI        A,10101010B
80F7  3200C8            STA        CONDIT1
80FA  3E55              MVI        A,01010101B
80FC  3200D0            STA        CONDIT2
80FF            ;            INITIALIZE INTERUPT DIAGNOSTIC
80FF  3E01              MVI        A,1
8101  32A2F8            STA        NFINTRPT
8104            ;            SET UP DUMMY INTERUPT ROUTINES
8104  210133            LXI        H,DUMMY
8107  2296F8            SHLD       TNEXT
810A  2298F8            SHLD       RNEXT
810D  229AF8            SHLD       BNEXT
8110  223DF8            SHLD       PNEXT
8113            ;            INITIALIZE RATES FOR DIP CORRECTION ETC.
8113                    MOVE       07000H,TSTRATES,26
8123            ;            INITIALIZE NDAYS TABLE
8123                    MOVE       INDAY,NDAYS,12
8133            ;            DEFAULT DISPLAY MESSAGE
8133  210680            LXI        H,CDSMSG
8136  2239F8            SHLD       INACTIVE
8139  2139F8            LXI        H,INACTIVE
813C  2200F8            SHLD       DSPTR1
813F  2123F8            LXI        H,IACTBUF
8142  2237F8            SHLD       ACTIVE
8145  2137F8            LXI        H,ACTIVE
8148  222DF8            SHLD       DSPTR2
814B            ;            LOAD THE DEFAULT METHOD
814B                    MOVE       IMETHD1,IMETHD0,SZ.MTH
815B                    MOVE       PMETHD1,PMETHD0,SZ.MTH
816B            ;            INITIALIZE INTERFACE TEMPERATURE AND FLAGS
816B  CD0350            CALL       EIXIT
816E            ;            INITIALIZE PROBE TEMPERATURE AND FLAGS
816E  CD0340            CALL       EPXIT
8171            ;            ENABLE TRAP INTERUPTS
8171  3A03E0            LDA        A2ST ; GET PORT STATUS
8174  F610              ORI        PREAD ; SET TRAP ENABLE
8176  3203E0            STA        A2ST ; SET PORT STATUS
8179  D304              OUT        A2
817B            ;
817B            ;            BENCHMARK, MAXIMUM AVAILABLE PROCESSOR TIME
817B  210000            LXI        H,0 ; CLEAR THE BENCHMARK
817E  225AF8            SHLD       COUNTA
8181  225CF8            SHLD       COUNTB
8184            ;            TO SYNCHRONIZE ON A TICK
8184                    TIMER      1,0,BMXIT,CBLK01
819C  CD0585            CALL       INPUT ; WAIT
819F  210000            LXI        H,0 ; CLEAR ACTIVE COUNTER
81A2  225AF8            SHLD       COUNTA
81A5            ;            GET AN ACCURATE COUNT
81A5                    TIMER      1,0,BMXIT,CBLK01
81BD  CD0585            CALL       INPUT ; WAIT
81C0  210000            LXI        H,0 ; CLEAR THE ACTIVE COUNT
81C3  225AF8            SHLD       COUNTA
81C6            ;
81C6            ;            CHECK INTERFACE TEMPERATURE
81C6                    TIMER      1,7,CHKTMP,CBLK01
81DE            ;            CHECK BATTERY
81DE                    TIMER      2,7,CHKBAT,CBLK02
81F6            ;            UPDATE DISPLAY
81F6                    TIMER      1,1,DISPLAY,CBLK03
820E            ;            PROCESSOR UTILIZATION ROUTINE
820E                    TIMER      1,1,UTILIZE,CBLK04
8226            ;            UPDATE CLOCK COUNTERS
8226                    TIMER      3,10,CLOCK,CBLK05
823E            ;            LIGHT THE HEARTBEAT LED
823E                    TIMER      2,3,HBEAT,CBLK07
```

```
8256                ;              UPDATE THE LED'S
8256                           TIMER    2,2,LEDUPD,CBLK08
826E                ;              MAINTAIN INTERFACE TEMPERATURE
826E                           TIMER    1,1,IFCTMP,CBLK12
8286                ;           DEFAULT TO THE PROBE AND SECONDS
8286   3A00E0                  LDA      A1ST
8289   F622                    ORI      LD.PRB+LD.SEC
828B   3200E0                  STA      A1ST
828E   212FF8                  LXI      H,PACTBUF
8291   2237F8                  SHLD     ACTIVE
8294                ;
8294            MAIN01         ENTRY
8294   CD0585                  CALL     INPUT ; WAIT FOR SOME OPERATOR INPUT
8297                ;
8297            MAIN02         ENTRY
8297                           COMAND   NCOMDS,ROUTNS,COMMDS ; SEE IF A VALID COMMAND
82A2   DA9482                  JC       MAIN01 ; IF NOT VALID COMMAND
82A5   E9                      PCHL     ; ELSE JUMP TO THE ROUTINE
82A6                ;
82A6            SRSTRT         ENTRY
82A6                ;              DO THE INTERFACE
82A6   3A00E0                  LDA      A1ST ; GET LEDS
82A9   E610                    ANI      LD.IFC ; INTERFACE ?
82AB   CAC582                  JZ       SRT01 ; NO ...
82AE   3A06F8                  LDA      IRUNFLG ; SEE IF RUNNING
82B1   FEFF                    CPI      OFFH
82B3   CC7A33                  CZ       BEEP2
82B6   CAC582                  JZ       SRT01 ; YES ...
82B9   3EFF                    MVI      A,OFFH ; SET RUNNING FLAG
82BB   3206F8                  STA      IRUNFLG
82BE   AF                      XRA      A
82BF   3207F8                  STA      IHLDFLG ; CLEAR HELD FLAG
82C2   CD0050                  CALL     EIINT ; GO START INTERFACE
82C5                ;              DO THE PROBE
82C5            SRT01
82C5   3A00E0                  LDA      A1ST ; GET LEDS
82C8   E620                    ANI      LD.PRB ; PROBE ?
82CA   CA9482                  JZ       MAIN01 ; NO ...
82CD   3A43F8                  LDA      PRUNFLG ; SEE IF RUNNING
82D0   FEFF                    CPI      OFFH
82D2   CC7A33                  CZ       BEEP2
82D5   CA9482                  JZ       MAIN01 ; YES ...
82D8   3EFF                    MVI      A,OFFH ; SET RUNNING FLAG
82DA   3243F8                  STA      PRUNFLG
82DD   AF                      XRA      A
82DE   3244F8                  STA      PHLDFLG ; CLEAR HELD FLAG
82E1   CD0040                  CALL     EPINT ; GO START PROBE
82E4   C39482                  JMP      MAIN01
82E7                ;
82E7            SRSTOP         ENTRY
82E7                ;              DO THE INTERFACE
82E7   3A00E0                  LDA      A1ST ; GET LEDS
82EA   E610                    ANI      LD.IFC ; INTERFACE ?
82EC   CAF282                  JZ       SRP01 ; NO ...
82EF   CD0350                  CALL     EIXIT ; RESET TO INITIAL STATE
82F2                ;              DO THE PROBE
82F2            SRP01
82F2   3A00E0                  LDA      A1ST ; GET LEDS
82F5   E620                    ANI      LD.PRB ; PROBE ?
82F7   CA9482                  JZ       MAIN01 ; NO ...
82FA   CD0340                  CALL     EPXIT ; RESET TO INITIAL STATE
82FD   C39482                  JMP      MAIN01
8300                ;
8300            SRHOLD         ENTRY
8300                ;              DO THE INTERFACE
8300   3A00E0                  LDA      A1ST ; GET LEDS
8303   E610                    ANI      LD.IFC ; INTERFACE ?
8305   CA2983                  JZ       SRH01 ; NO ...
8308   3A06F8                  LDA      IRUNFLG ; SEE IF RUNNING
830B   FEFF                    CPI      OFFH
830D   C22983                  JNZ      SRH01 ; NOT RUNNING
8310   3A07F8                  LDA      IHLDFLG ; SEE IF ALREADY HELD
8313   FEFF                    CPI      OFFH
8315   CA2983                  JZ       SRH01 ; YES ...
8318   3EFF                    MVI      A,OFFH ; INDICATE IT IS HELD
831A   3207F8                  STA      IHLDFLG
831D                           DELETE   CBLK09 ; REMOVE STEP TIMER
8323                           DELETE   CBLK13 ; REMOVE RAMP TIMER
8329                ;              DO THE PROBE
8329            SRH01
8329   3A00E0                  LDA      A1ST ; GET LEDS
832C   E620                    ANI      LD.PRB ; PROBE ?
832E   CA9482                  JZ       MAIN01 ; NO ...
8331   3A43F8                  LDA      PRUNFLG ; SEE IF RUNNING
8334   FEFF                    CPI      OFFH
8336   C29482                  JNZ      MAIN01 ; NOT RUNNING
8339   3A44F8                  LDA      PHLDFLG ; SEE IF ALREADY HELD
833C   FEFF                    CPI      OFFH
833E   CA9482                  JZ       MAIN01 ; YES ...
8341   3EFF                    MVI      A,OFFH ; INDICATE IT IS HELD
8343   3244F8                  STA      PHLDFLG
8346                           DELETE   CBLK14 ; REMOVE STEP TIMER
```

```
834C                         DELETE    CBLK15 ; REMOVE RAMP TIMER
8352  C39482                 JMP       MAIN01
8355            ;
8355            SRRESM       ENTRY
8355                 ;                 DO THE INTERFACE
8355  3A00E0                 LDA       A1ST ; GET LEDS
8358  E610                   ANI       LD.IFC ; INTERFACE ?
835A  CA7D83                 JZ        SRR02 ; NO ...
835D  3A06F8                 LDA       IRUNFLG ; SEE IF IT IS RUNNING
8360  FEFF                   CPI       0FFH
8362  C27D83                 JNZ       SRR02 ; NO ...
8365  3A07F8                 LDA       IHLDFLG ; SEE IF HELD
8368  FEFF                   CPI       0FFH
836A  C27D83                 JNZ       SRR02 ; NO ...
836D  2188F0                 LXI       H,CBLK13 ; PUT RAMP TIMER INTO QUE
8370  CD6230                 CALL      QUEUE
8373  2170F0                 LXI       H,CBLK09 ; PUT STEP TIMER INTO QUE
8376  CD6230                 CALL      QUEUE
8379  AF                     XRA       A ; CLEAR THE FLAGS
837A  3207F8                 STA       IHLDFLG
837D            ;                      DO THE PROBE
837D            SRR02
837D  3A00E0                 LDA       A1ST ; GET LEDS
8380  E620                   ANI       LD.PRB ; PROBE ?
8382  CA9482                 JZ        MAIN01 ; NO ...
8385  3A43F8                 LDA       PRUNFLG ; SEE IF IT IS RUNNING
8388  FEFF                   CPI       0FFH
838A  C29482                 JNZ       MAIN01 ; NO ...
838D  3A44F8                 LDA       PHLDFLG ; SEE IF HELD
8390  FEFF                   CPI       0FFH
8392  C29482                 JNZ       MAIN01 ; NO ...
8395  2194F0                 LXI       H,CBLK15 ; PUT RAMP TIMER INTO QUE
8398  CD6230                 CALL      QUEUE
839B  218EF0                 LXI       H,CBLK14 ; PUT STEP TIMER INTO QUE
839E  CD6230                 CALL      QUEUE
83A1  AF                     XRA       A ; CLEAR THE FLAGS
83A2  3244F8                 STA       PHLDFLG
83A5  C39482                 JMP       MAIN01
83A8            ;*************************************************************
83A8            ;
83A8                         USE       PRGM
83A8            ;
83A8            ;                      BATTERY CHECK ROUTINE      * * * * * * * * * *
83A8            ;
83A8  0000C0B0   BATERR      DB        BLANK,BLANK,BCODE,ACODE,DCODE,BCODE,ACODE,TCODE
      E0C0B0B2
83B0            ;
83B0            CHKBAT       ENTRY
83B0  DB12                   IN        012H ; GET THE PORT STATUS
83B2  E640                   ANI       BATTRY ; SEE IF THE BATTERYS ARE THERE
83B4  CAC083                 JZ        CB01 ; YES, SO EXIT
83B7  21A883                 LXI       H,BATERR ; ELSE TELL THEM THAT THE BATTERYS ARE SHOT
83BA  2237F8                 SHLD      ACTIVE
83BD  2239F8                 SHLD      INACTIVE
83C0            CB01
83C0  C9                     RET
83C1            ;*************************************************************
83C1            ;
83C1                         USE       PRGM
83C1            ;
83C1            ;                      TEMPERATURE MONITOR ROUTINE    * * * * * * * *
83C1            ;
83C1  0000C0B0   BDTMSG      DB        BLANK,BLANK,BCODE,ACODE,DCODE,TCODE,MCODE,PCODE
      E0B25282
83C9            ;
83C9            CHKTMP       ENTRY
83C9  CD1634                 CALL      VIN
83CC  2A09E0                 LHLD      CH1IN ; GET ACTUAL TEMP
83CF  29                     DAD       H ; TIMES 2 FOR OFFSET
83D0  0100B0                 LXI       B,TABLE2 ; POINT TO CONVERSION TABLE
83D3  09                     DAD       B ; POINT TO CONVERSION
83D4  5E                     MOV       E,M ; PUT TRUE TEMP INTO 'DE'
83D5  23                     INX       H
83D6  56                     MOV       D,M
83D7                         SAVE      D,D,D ; PUT TRUE TEMP INTO 'HL' AND STACK TWICE
83DA                         RESTOR    H
83DB  CD1532                 CALL      BIN2PK ; CONVERT TO PACKED IN 'HL'
83DE  0125F8                 LXI       B,IACTBUF+2 ; POINT TO DISPLAY BUFFER
83E1  CD3031                 CALL      PRVRT3 ; CONVERT TO DISPLAYABLE
83E4                         RESTOR    H
83E5  0105FF                 LXI       B,"T.MAX ; GET COMPLEMENT OF MAX TEMP
83E8  09                     DAD       B
83E9  DAF583                 JC        CT01 ; OVERTEMP
83EC                         RESTOR    H ; GET TRUE TEMP
83ED  01F9FF                 LXI       B,"T.MIN ; GET COMPLEMENT OF MIN TEMP
83F0  09                     DAD       B
83F1  D2F683                 JNC       CT02 ; UNDER TEMP
83F4  C9                     RET       ; TEMP GOOD
83F5            CT01
83F5                         RESTOR    H ; FIX STACK
83F6            CT02
83F6  CD0350                 CALL      EIXIT
83F9  210000                 LXI       H,0 ; TURN OFF INTERFACE HEATER
```

```
83FC  2218F8              SHLD    ITEMP
83FF  CD0340              CALL    EPXIT
8402  21C183              LXI     H,BDTMSG ; DISPLAY MESSAGE
8405  2237F8              SHLD    ACTIVE
8408  2239F8              SHLD    INACTIVE
840B  C9                  RET
840C          ;************************************************************
840C          ;
840C          ;           USE     PRGM
840C          ;
840C          ;              PULSE THE HEARTBEAT LED
840C          ;
840C          ;
840C          ;
840C          HBEAT       ENTRY
840C  3A00E0              LDA     A1ST
840F  EE40                XRI     LD.HBT
8411  3200E0              STA     A1ST
8414  C9                  RET
8415          ;************************************************************
8415          ;
8415          ;           USE     PRGM
8415          ;
8415          ;         CLOCK COUNTER ROUTINE, KY.ENTERED EVERY SECOND    * * * * *
8415          ;         MAINTAINS TIME AND DATE IN PACKED DECIMAL FORMAT
8415          ;
8415          ;
8415          CLOCK       ENTRY
8415          ;
8415  3AB7C8              LDA     SECS ; GET THE SECONDS COUNTER
8418  3C                  INR     A
8419  27                  DAA
841A  32B7C8              STA     SECS
841D  FE60                CPI     060H
841F  FAA184              JM      CLKXIT
8422  AF                  XRA     A
8423  32B7C8              STA     SECS
8426          ;
8426  3AB8C8              LDA     MINS ; GET THE MINUTES COUNTER
8429  3C                  INR     A
842A  27                  DAA
842B  32B8C8              STA     MINS
842E  FE60                CPI     060H
8430  FAA184              JM      CLKXIT
8433  AF                  XRA     A
8434  32B8C8              STA     MINS
8437          ;
8437  3AB9C8              LDA     HOURS ; GET THE HOURS COUNTER
843A  3C                  INR     A
843B  27                  DAA
843C  32B9C8              STA     HOURS
843F  FE24                CPI     024H
8441  FAA184              JM      CLKXIT
8444  AF                  XRA     A
8445  32B9C8              STA     HOURS
8448          ;
8448  3ABAC8              LDA     DAYS ; GET THE DAY COUNTER
844B  3C                  INR     A
844C  27                  DAA
844D  32BAC8              STA     DAYS
8450  01AAC8              LXI     B,NDAYS-1 ; POINT TO THE NUMBER OF DAYS/MONTH TABLE
8453  3ABBC8              LDA     MONTHS ; GET THE CURRENT MONTH
8456  CLK01
8456  03                  INX     B ; POINT TO THE NEXT TABLE ENTRY
8457  3D                  DCR     A
8458  C25684              JNZ     CLK01
845B  0A                  LDAX    B ; GET THE NUMBER OF DAYS THIS MONTH
845C  21BAC8              LXI     H,DAYS ; POINT TO THE DAYS COUNTER
845F  BE                  CMP     M ; SEE IF THIS MONTH IS OVER
8460  F2A184              JP      CLKXIT ; NO ...
8463  3E01                MVI     A,1 ; RESET TO DAY 1
8465  32BAC8              STA     DAYS
8468          ;
8468  3ABBC8              LDA     MONTHS ; GET THE MONTHS COUNTER
846B  3C                  INR     A
846C  27                  DAA
846D  32BBC8              STA     MONTHS
8470  FE12                CPI     012H
8472  FAA184              JM      CLKXIT
8475  CAA184              JZ      CLKXIT
8478  3E01                MVI     A,1
847A  32BBC8              STA     MONTHS
847D          ;
847D  3ABCC8              LDA     YEARS ; GET THE YEARS COUNTER
8480  3C                  INR     A
8481  27                  DAA
8482  32BCC8              STA     YEARS
8485          ;      CHECK FOR A LEAP YEAR
8485  B7                  ORA     A ; CLEAR CARRY
8486  1F                  RAR
8487  B7                  ORA     A
8488  1F                  RAR
8489  B7                  ORA     A
848A  17                  RAL
```

```
848B  B7                        ORA       A
848C  17                        RAL
848D  21BCC8                    LXI       H,YEARS
8490  BE                        CMP       M ; SEE IF DIVISIBLE BY 4
8491  C29C84                    JNZ       CLK02 ; NO ...
8494  3E29                      MVI       A,029H
8496  32ACC8                    STA       NDAYS+1 ; RESET FEBRUAURY TO 29 DAYS
8499  C3A184                    JMP       CLKXIT
849C                 CLK02
849C  3E28                      MVI       A,028H
849E  32ACC8                    STA       NDAYS+1 ; RESET FEBRUARY TO 28 DAYS
84A1                 CLKXIT
84A1  C9                        RET
84A2                         ;***************************************************************
84A2                         ;
84A2                                       USE       PRGM
84A2                         ;
84A2                         ;             DATE/TIME ROUTINE       * * * * * * * * * * *
84A2                         ;      MAINTAINS DATE/TIME DISPLAY BUFFERS
84A2
84A2                         ;
84A2                 DATIM    ENTRY
84A2                                       FILL      TIME,BLANK,8
84AF  01C3C8                    LXI       B,TIME+6 ; POINT TO TIME BUFFER
84B2  3AB7C8                    LDA       SECS
84B5  67                        MOV       H,A
84B6  2E00                      MVI       L,0
84B8  CD2C31                    CALL      PRVRT2
84BB  01C0C8                    LXI       B,TIME+3
84BE  3AB8C8                    LDA       MINS
84C1  67                        MOV       H,A
84C2  2E00                      MVI       L,0
84C4  CD2C31                    CALL      PRVRT2
84C7  01BDC8                    LXI       B,TIME
84CA  3AB9C8                    LDA       HOURS
84CD  67                        MOV       H,A
84CE  2E00                      MVI       L,0
84D0  CD2C31                    CALL      PRVRT2
84D3                         ;
84D3                                       FILL      DATE,BLANK,8
84E0  01CBC8                    LXI       B,DATE+6 ; POINT TO THE DATE BUFFER
84E3  3ABCC8                    LDA       YEARS
84E6  67                        MOV       H,A
84E7  2E00                      MVI       L,0
84E9  CD2C31                    CALL      PRVRT2
84EC  01C8C8                    LXI       B,DATE+3
84EF  3ABAC8                    LDA       DAYS
84F2  67                        MOV       H,A
84F3  2E00                      MVI       L,0
84F5  CD2C31                    CALL      PRVRT2
84F8  01C5C8                    LXI       B,DATE
84FB  3ABBC8                    LDA       MONTHS
84FE  67                        MOV       H,A
84FF  2E00                      MVI       L,0
8501  CD2C31                    CALL      PRVRT2
8504  C9                        RET
8505                         ;***************************************************************
8505                         ;
8505                                       USE       PRGM
8505                         ;
8505                         ;             KEYBOARD INPUT ROUTINE
8505                         ;      'A' WILL CONTAIN THE KEY VALUE.
8505                         ;      WILL NOT RETURN UNTIL A KEY IS HIT.
8505                         ;
8505                 INPUT    ENTRY
8505                                       SAVE      H,D
8507                 INP00
8507  11FFFF                    LXI       D,0FFFFH
850A  215500                    LXI       H,85 ; 85 SHOULD GIVE ONE COUNT EACH MILLISECOND
850D                 INP00.5
850D  19                        DAD       D
850E  DA0D85                    JC        INP00.5
8511  2A5AF8                    LHLD      COUNTA ; COUNT FOR PROCESSOR UTILIZATION
8514  23                        INX       H
8515  225AF8                    SHLD      COUNTA
8518  3A1AF8                    LDA       CHAR ; SEE IF ANY INPUT
851B  FE00                      CPI       0
851D  CA0785                    JZ        INP00 ; NO ...
8520  FEE6                      CPI       KY.RESET ; SEE IF A RESET IS DESIRED
8522  CA0380                    JZ        MAIN ; YES ...
8525  CDA333                    CALL      BEEP3
8528  FECC                      CPI       KY.TBASE ; SEE IF A CHANGE OF TIME BASE IS DESIRED
852A  CA5F85                    JZ        INP05 ; YES ...
852D  FECE                      CPI       KY.PROBE ; SEE IF THE PROBE IS DESIRED
852F  CA6985                    JZ        INP10 ; YES ...
8532  FECA                      CPI       KY.STACT ; SEE IF TOGGLE SET/ACTUAL IS DESIRED
8534  CAAC85                    JZ        INP40 ; YES ...
8537  FECF                      CPI       KY.BOTH ; SEE IF BOTH INTERFACE AND PROBE ARE DESIRED
8539  CAC185                    JZ        INP50 ; YES ...
853C  FEEA                      CPI       KY.ZERO2
853E  C24385                    JNZ       INP01
8541  3EE9                      MVI       A,KY.ZERO1
8543                 INP01
8543  FEE8                      CPI       KY.ZERO3
```

```
8545  C24A85              JNZ      INP02
8548  3EE9                MVI      A,KY.ZERO1
854A         INP02
854A                      SAVE     PSW ; SAVE THE CHARACTER
854B  AF                  XRA      A ; CLEAR THE CHARACTER BUFFER READY FOR THE NEXT
854C  321AF8              STA      CHAR
854F                      RESTOR   PSW,D,H
8552  C9                  RET
8553         ;
8553         BMXIT
8553  2A5AF8              LHLD     COUNTA ; GET ACTIVE COUNT
8556  225CF8              SHLD     COUNTB ; SAVE AS BENCH MARK
8559  3EFF                MVI      A,OFFH ; TO ENABLE RETURN
855B  321AF8              STA      CHAR
855E  C9                  RET
855F         ;                  TOGGLE TIMEBASE LED
855F         INP05
855F  AF                  XRA      A
8560  321AF8              STA      CHAR ; CLEAR IT
8563  CDE289              CALL     TGLTBS ; TOGGLE TIME BASE
8566  C30785              JMP      INP00
8569         ;                  TOGGLE INTERFACE/PROBE LEDS
8569         INP10
8569  3A00E0              LDA      A1ST ; GET THE LED STATUS
856C  E610                ANI      LD.IFC ; SEE IF INTERFACE LED IS LIT
856E  C28185              JNZ      INP11 ; NO, GO SET PROBE LED ON
8571  3A00E0              LDA      A1ST
8574  F610                ORI      LD.IFC
8576  E6DF                ANI      "LD.PRB
8578  3200E0              STA      A1ST
857B  2123F8              LXI      H,IACTBUF ; POINT TO INTERFACE ACTIVITY BUFFER
857E  C38E85              JMP      INP12
8581         INP11
8581  3A00E0              LDA      A1ST
8584  F620                ORI      LD.PRB
8586  E6EF                ANI      "LD.IFC
8588  3200E0              STA      A1ST
858B  212FF8              LXI      H,PACTBUF ; POINT TO PROBE ACTIVITY BUFFER
858E         INP12
858E  2237F8              SHLD     ACTIVE
8591  3A9EF8              LDA      PIRTN ; SEE IF THE RETURN FLAG IS SET
8594  FEFF                CPI      OFFH
8596  C2A585              JNZ      INP12.5 ; NO ...
8599  AF                  XRA      A ; ELSE CLEAR RETURN FLAG
859A  329EF8              STA      PIRTN
859D  321AF8              STA      CHAR ; AND CHARACTER
85A0  3ECE                MVI      A,KY.PROBE ; RETURN CORRECT KEY
85A2                      RESTOR   D,H
85A4  C9                  RET
85A5         INP12.5
85A5  AF                  XRA      A ; CLEAR IT
85A6  321AF8              STA      CHAR
85A9  C30785              JMP      INP00
85AC         ;                  SET/ACTIVE DISPLAY TOGGLE
85AC         INP40
85AC  2A00F8              LHLD     DSPTR1
85AF                      SAVE     H
85B0  2A2DF8              LHLD     DSPTR2
85B3  2200F8              SHLD     DSPTR1
85B6                      RESTOR   H
85B7  222DF8              SHLD     DSPTR2
85BA  AF                  XRA      A
85BB  321AF8              STA      CHAR
85BE  C30785              JMP      INP00
85C1         ;
85C1         INP50
85C1  3A00E0              LDA      A1ST
85C4  F630                ORI      LD.IFC+LD.PRB
85C6  3200E0              STA      A1ST
85C9  AF                  XRA      A ; CLEAR IT
85CA  321AF8              STA      CHAR
85CD  C30785              JMP      INP00
85D0         ;********************************************************************
85D0         ;
85D0                      USE      PRGM
85D0         ;
85D0         ;               DATE AND TIME USER FUNCTIONS
85D0         ;        ALLOW THE USER TO EXAMINE AND/OR SET THE TIME AND DATE
85D0         ;
85D0         ;
85D0  D0422222  TMMSG     DB       CCODE,LCODE,HCODE,HCODE,MCODE,MCODE,SCODE,SCODE
      5252A2A2
85D8  E0B25252  DTMSG     DB       DCODE,TCODE,MCODE,MCODE,DCODE,DCODE,YCODE,YCODE
      E0E0F2F2
85E0         ;
85E0         ;
85E0         DTECLK      ENTRY
85E0  2109F8              LXI      H,DTBUF ; SETUP DISPLAY BUFFER FOR PANEL
85E3  2239F8              SHLD     INACTIVE
85E6         ;
85E6  3A12F8              LDA      DATI ; SEE IF TO DISPLAY DATE OR TIME
85E9  A7                  ANA      A
85EA  C26987              JNZ      DT010 ; GO DISPLAY DATE
85ED         ;
85ED         ;                  ELSE DISPLAY TIME
```

```
85ED                   ;
85ED                         MOVE      TMMSG,DTBUF,8 ; TIME PROMPT
85FD                   ;
85FD   3EFF                  MVI       A,OFFH ; TOGGLE DATE/TIME PROMPTING
85FF   3212F8                STA       DATI
8602                   ;
8602             DT01
8602   CD0585                CALL      INPUT ; GET A KEY
8605   FECB                  CPI       KY.DSPLY
8607   CA6189                JZ        DISDT
860A                         COMAND    NCOMDS,ROUTNS,COMMDS
8615   D2E189                JNC       DT100 ; IF A VALID COMMAND
8618   CD8732                CALL      KB2BIN ; ELSE SEE IF A NUMERAL
861B   DC7A33                CC        BEEP2
861E   DA0286                JC        DT01 ; NO, MUST BE GARBAGE
8621   CDA032                CALL      BIN2DS ; CONVERT TO DISPLAYABLE FORM
8624   FE40                  CPI       CODE3 ; SEE IF A 3 OR HIGHER
8626   F47A33                CP        BEEP2
8629   F20286                JP        DT01 ; YES ...
862C   320BF8                STA       DTBUF+2
862F   FE30                  CPI       CODE2 ; SEE IF A 2
8631   CA5C86                JZ        DT01.1 ; YES ...
8634             DT01.0
8634   CD0585                CALL      INPUT ; GET A KEY
8637   FECB                  CPI       KY.DSPLY
8639   CA6189                JZ        DISDT
863C                         COMAND    NCOMDS,ROUTNS,COMMDS
8647   D2E189                JNC       DT100 ; IF A VALID COMMAND
864A   CD8732                CALL      KB2BIN ; ELSE SEE IF A NUMERAL
864D   DC7A33                CC        BEEP2
8650   DA3486                JC        DT01.0 ; NO, MUST BE GARBAGE
8653   CDA032                CALL      BIN2DS ; CONVERT TO DISPLAYABLE FORM
8656   320CF8                STA       DTBUF+3
8659   C38986                JMP       DT01.2
865C             DT01.1
865C   CD0585                CALL      INPUT
865F   FECB                  CPI       KY.DSPLY
8661   CA6189                JZ        DISDT
8664                         COMAND    NCOMDS,ROUTNS,COMMDS
866F   D2E189                JNC       DT100
8672   CD8732                CALL      KB2BIN
8675   DC7A33                CC        BEEP2
8678   DA5C86                JC        DT01.1
867B   CDA032                CALL      BIN2DS
867E   FE50                  CPI       CODE4 ; SEE IF HIGHER THAN 3
8680   F47A33                CP        BEEP2
8683   F25C86                JP        DT01.1 ; YES ...
8686   320CF8                STA       DTBUF+3
8689             DT01.2
8689   CD0585                CALL      INPUT
868C   FECB                  CPI       KY.DSPLY
868E   CA6189                JZ        DISDT
8691                         COMAND    NCOMDS,ROUTNS,COMMDS
869C   D2E189                JNC       DT100
869F   CD8732                CALL      KB2BIN
86A2   DC7A33                CC        BEEP2
86A5   DA8986                JC        DT01.2
86A8   CDA032                CALL      BIN2DS
86AB   FE70                  CPI       CODE6 ; SEE IF HIGHER THAN 5
86AD   F47A33                CP        BEEP2
86B0   F28986                JP        DT01.2 ; YES ...
86B3   320DF8                STA       DTBUF+4
86B6             DT01.3
86B6   CD0585                CALL      INPUT
86B9   FECB                  CPI       KY.DSPLY
86BB   CA6189                JZ        DISDT
86BE                         COMAND    NCOMDS,ROUTNS,COMMDS
86C9   D2E189                JNC       DT100
86CC   CD8732                CALL      KB2BIN
86CF   DC7A33                CC        BEEP2
86D2   DAB686                JC        DT01.3
86D5   CDA032                CALL      BIN2DS
86D8   320EF8                STA       DTBUF+5
86DB             DT01.4
86DB   CD0585                CALL      INPUT
86DE   FECB                  CPI       KY.DSPLY
86E0   CA6189                JZ        DISDT
86E3                         COMAND    NCOMDS,ROUTNS,COMMDS
86EE   D2E189                JNC       DT100
86F1   CD8732                CALL      KB2BIN
86F4   DC7A33                CC        BEEP2
86F7   DADB86                JC        DT01.4
86FA   CDA032                CALL      BIN2DS
86FD   FE70                  CPI       CODE6 ; SEE IF HIGHER THAN 5
86FF   F47A33                CP        BEEP2
8702   F2DB86                JP        DT01.4 ; YES ...
8705   320FF8                STA       DTBUF+6
8708             DT01.5
8708   CD0585                CALL      INPUT
870B   FECB                  CPI       KY.DSPLY
870D   CA6189                JZ        DISDT
8710                         COMAND    NCOMDS,ROUTNS,COMMDS
871B   D2E189                JNC       DT100
871E   CD8732                CALL      KB2BIN
8721   DC7A33                CC        BEEP2
```

```
8724  DA0887              JC       DT01.5
8727  CDA032              CALL     BIN2DS
872A  3210F8              STA      DTBUF+7
872D           DT01.6
872D  CD0585              CALL     INPUT
8730  FECB                CPI      KY.DSPLY
8732  CA6189              JZ       DISDT
8735  FEC8                CPI      KY.ENTER
8737  CA4887              JZ       DT01.7
873A                      COMAND   NCOMDS,ROUTNS,COMMDS
8745  D2E189              JNC      DT100
8748                      JMP DT01.6
8748           ;          SAVE THE NEW TIME
8748           DT01.7
8748  010BF8              LXI      B,DTBUF+2
874B  CD5E31              CALL     CNVRT2
874E  7C                  MOV      A,H
874F  32B9C8              STA      HOURS
8752  010DF8              LXI      B,DTBUF+4
8755  CD5E31              CALL     CNVRT2
8758  7C                  MOV      A,H
8759  32B8C8              STA      MINS
875C  010FF8              LXI      B,DTBUF+6
875F  CD5E31              CALL     CNVRT2
8762  7C                  MOV      A,H
8763  32B7C8              STA      SECS
8766  C35989              JMP      DT020
8769           ;
8769           ;          DO THE DATE
8769           ;
8769           DT010
8769  2109F8              LXI      H,DTBUF
876C  2239F8              SHLD     INACTIVE
876F           ;
876F                      MOVE     DTMSG,DTBUF,8
877F           ;
877F  AF                  XRA      A ; TOGGLE DATE/TIME PROMPTING
8780  3212F8              STA      DATI
8783           ;
8783           DT011
8783  CD0585              CALL     INPUT
8786  FECB                CPI      KY.DSPLY
8788  CA6189              JZ       DISDT
878B                      COMAND   NCOMDS,ROUTNS,COMMDS
8796  D2E189              JNC      DT100
8799  CD8732              CALL     KB2BIN
879C  DC7A33              CC       BEEP2
879F  DA8387              JC       DT011
87A2  CDA032              CALL     BIN2DS
87A5  FE30                CPI      CODE2 ; SEE IF A 2 OR HIGHER
87A7  F47A33              CP       BEEP2
87AA  F28387              JP       DT011 ; YES ...
87AD  320BF8              STA      DTBUF+2
87B0  FE20                CPI      CODE1 ; SEE IF A 1
87B2  CAE587              JZ       DT011.1 ; YES ...
87B5           DT011.0
87B5  CD0585              CALL     INPUT
87B8  FECB                CPI      KY.DSPLY
87BA  CA6189              JZ       DISDT
87BD                      COMAND   NCOMDS,ROUTNS,COMMDS
87C8  D2E189              JNC      DT100
87CB  CD8732              CALL     KB2BIN
87CE  DC7A33              CC       BEEP2
87D1  DAB587              JC       DT011.0
87D4  CDA032              CALL     BIN2DS
87D7  FE10                CPI      CODE0 ; MUST BE 1 OR HIGHER
87D9  CC7A33              CZ       BEEP2
87DC  CAB587              JZ       DT011.0 ; IS NOT
87DF  320CF8              STA      DTBUF+3
87E2  C31288              JMP      DT011.2
87E5           DT011.1
87E5  CD0585              CALL     INPUT
87E8  FECB                CPI      KY.DSPLY
87EA  CA6189              JZ       DISDT
87ED                      COMAND   NCOMDS,ROUTNS,COMMDS
87F8  D2E189              JNC      DT100
87FB  CD8732              CALL     KB2BIN
87FE  DC7A33              CC       BEEP2
8801  DAE587              JC       DT011.1
8804  CDA032              CALL     BIN2DS
8807  FE40                CPI      CODE3 ; SEE IF HIGHER THAN 2
8809  F47A33              CP       BEEP2
880C  F2E587              JP       DT011.1 ; YES ...
880F  320CF8              STA      DTBUF+3
8812           DT011.2
8812  CD0585              CALL     INPUT
8815  FECB                CPI      KY.DSPLY
8817  CA6189              JZ       DISDT
881A                      COMAND   NCOMDS,ROUTNS,COMMDS
8825  D2E189              JNC      DT100
8828  CD8732              CALL     KB2BIN
882B  DC7A33              CC       BEEP2
882E  DA1288              JC       DT011.2
8831  CDA032              CALL     BIN2DS
8834  FE50                CPI      CODE4 ; SEE IF HIGHER THAN 3
```

```
8836  F47A33              CP      BEEP2
8839  F21288              JP      DT011.2 ; YES ...
883C  320DF8              STA     DTBUF+4
883F  FE40                CPI     CODE3 ; SEE IF A 3
8841  CA7488              JZ      DT011.3.1 ; YES ...
8844  FE10                CPI     CODE0 ; SEE IF A 0
8846  CC7A33              CZ      BEEP2
8849  CAA488              JZ      DT011.3.2 ; YES ...
884C          DT011.3
884C  CD0585              CALL    INPUT
884F  FECB                CPI     KY.DSPLY
8851  CA6189              JZ      DISDT
8854                      COMAND  NCOMDS,ROUTNS,COMMDS
885F  D2E189              JNC     DT100
8862  CD8732              CALL    KB2BIN
8865  DC7A33              CC      BEEP2
8868  DA4C88              JC      DT011.3
886B  CDA032              CALL    BIN2DS
886E  320EF8              STA     DTBUF+5
8871  C3D388              JMP     DT011.4
8874          DT011.3.1
8874  CD0585              CALL    INPUT
8877  FECB                CPI     KY.DSPLY
8879  CA6189              JZ      DISDT
887C                      COMAND  NCOMDS,ROUTNS,COMMDS
8887  D2E189              JNC     DT100
888A  CD8732              CALL    KB2BIN
888D  DC7A33              CC      BEEP2
8890  DA7488              JC      DT011.3.1
8893  CDA032              CALL    BIN2DS
8896  FE30                CPI     CODE2 ; SEE IF HIGHER THAN 1
8898  F47A33              CP      BEEP2
889B  F27488              JP      DT011.3.1 ; YES ...
889E  320EF8              STA     DTBUF+5
88A1  C3D388              JMP     DT011.4
88A4          DT011.3.2
88A4  CD0585              CALL    INPUT
88A7  FECB                CPI     KY.DSPLY
88A9  CA6189              JZ      DISDT
88AC                      COMAND  NCOMDS,ROUTNS,COMMDS
88B7  D2E189              JNC     DT100
88BA  CD8732              CALL    KB2BIN
88BD  DC7A33              CC      BEEP2
88C0  DAA488              JC      DT011.3.2
88C3  A7                  ANA     A
88C4  CC7A33              CZ      BEEP2
88C7  CAA488              JZ      DT011.3.2 ; IF A 0
88CA  CDA032              CALL    BIN2DS
88CD  F2A488              JP      DT011.3.2
88D0  320EF8              STA     DTBUF+5
88D3          DT011.4
88D3  CD0585              CALL    INPUT
88D6  FECB                CPI     KY.DSPLY
88D8  CA6189              JZ      DISDT
88DB                      COMAND  NCOMDS,ROUTNS,COMMDS
88E6  D2E189              JNC     DT100
88E9  CD8732              CALL    KB2BIN
88EC  DC7A33              CC      BEEP2
88EF  DAD388              JC      DT011.4
88F2  CDA032              CALL    BIN2DS
88F5  320FF8              STA     DTBUF+6
88F8          DT011.5
88F8  CD0585              CALL    INPUT
88FB  FECB                CPI     KY.DSPLY
88FD  CA6189              JZ      DISDT
8900                      COMAND  NCOMDS,ROUTNS,COMMDS
890B  D2E189              JNC     DT100
890E  CD8732              CALL    KB2BIN
8911  DC7A33              CC      BEEP2
8914  DAF888              JC      DT011.5
8917  CDA032              CALL    BIN2DS
891A  3210F8              STA     DTBUF+7
891D          ;           MUST EXIT WITH THE ENTER KEY
891D          DT011.6
891D  CD0585              CALL    INPUT
8920  FECB                CPI     KY.DSPLY
8922  CA6189              JZ      DISDT
8925  FEC8                CPI     KY.ENTER
8927  CA3B89              JZ      DT012
892A                      COMAND  NCOMDS,ROUTNS,COMMDS
8935  D2E189              JNC     DT100
8938  C31D89              JMP     DT011.6
893B          ;           SAVE THE NEW DATE
893B          DT012
893B  010BF8              LXI     B,DTBUF+2
893E  CD5E31              CALL    CNVRT2
8941  7C                  MOV     A,H
8942  32BBC8              STA     MONTHS
8945  010DF8              LXI     B,DTBUF+4
8948  CD5E31              CALL    CNVRT2
894B  7C                  MOV     A,H
894C  32BAC8              STA     DAYS
894F  010FF8              LXI     B,DTBUF+6
8952  CD5E31              CALL    CNVRT2
8955  7C                  MOV     A,H
```

```
8956   32BCC8                        STA        YEARS
8959              ;
8959              ;             JUST TO CHECK FOR THE DISPLAY KEY
8959              DT020
8959   CD0585                        CALL       INPUT
895C   FECB                          CPI        KY.DSPLY
895E   C29782                        JNZ        MAIN02
8961              ;
8961              DISDT             ENTRY
8961              ;             UPDATE THE TIME/DATE DISPLAY BUFFERS
8961                                 TIMER      1,10,DATIM,CBLK06
8979   CDA389                        CALL       DISTIM
897C              DIS01
897C   CD0585                        CALL       INPUT
897F   FECB                          CPI        KY.DSPLY ; SEE IF THE KY.DSPLY KEY
8981   CA6189                        JZ         DISDT ; IF SO, REDO
8984                                 COMAND     NCOMDS,ROUTNS,COMMDS
898F   DA7C89                        JC         DIS01
8992                                 SAVE       H
8993                                 DELETE     CBLK11 ; REMOVE DATE/TIME DISPLAY QUE ENTRY
8999                                 DELETE     CBLK06 ; REMOVE THE DATE/TIME BUFFER DISPLAY BUFFER UPDATE
899F                                 RESTOR     H
89A0   C3E189                        JMP        DT100
89A3              ;
89A3              DISTIM            ENTRY
89A3                                 TIMER      80,0,DISDAT,CBLK11
89BB   21BDC8                        LXI        H,TIME
89BE   2239F8                        SHLD       INACTIVE
89C1   C9                            RET
89C2              ;
89C2              DISDAT            ENTRY
89C2                                 TIMER      20,0,DISTIM,CBLK11
89DA   21C5C8                        LXI        H,DATE
89DD   2239F8                        SHLD       INACTIVE
89E0   C9                            RET
89E1              ;
89E1              DT100
89E1   E9                            PCHL
89E2              ;****************************************************************
89E2              ;
89E2                                 USE        PRGM
89E2              ;
89E2              ;             TOGGLE TIME BASE BITS
89E2              ;
89E2              TGLTBS            ENTRY
89E2                                 SAVE       PSW
89E3   3A00E0                        LDA        A1ST ; GET LEDS
89E6   E608                          ANI        LD.HOUR ; SEE IF IN HOURS
89E8   C2078A                        JNZ        TB01 ; YES ...
89EB   3A00E0                        LDA        A1ST ; GET LEDS
89EE   E604                          ANI        LD.MIN ; SEE IF IN MINS
89F0   C2138A                        JNZ        TB02 ; YES ...
89F3   3A00E0                        LDA        A1ST ; GET LEDS
89F6   E602                          ANI        LD.SEC ; SEE IF IN SECONDS
89F8   C21F8A                        JNZ        TB03 ; YES ...
89FB              ;             ASSUME IN MILLISECONDS
89FB   3A00E0                        LDA        A1ST ; GET LEDS
89FE   E6F0                          ANI        0F0H ; CLEAR TIME BASE BITS
8A00   F608                          ORI        LD.HOUR ; SET HOURS BIT
8A02   3200E0                        STA        A1ST ; SAVE LEDS
8A05                                 RESTOR     PSW
8A06   C9                            RET
8A07              ;             IF IN HOURS
8A07              TB01
8A07   3A00E0                        LDA        A1ST ; GET LEDS
8A0A   E6F0                          ANI        0F0H ; CLEAR TIME BASE BITS
8A0C   F604                          ORI        LD.MIN ; SET MINUTES BIT
8A0E   3200E0                        STA        A1ST ; SAVE LEDS
8A11                                 RESTOR     PSW
8A12   C9                            RET
8A13              ;             IF IN MINUTES
8A13              TB02
8A13   3A00E0                        LDA        A1ST ; GET LEDS
8A16   E6F0                          ANI        0F0H ; CLEAR TIME BASE BITS
8A18   F602                          ORI        LD.SEC ; SET SECONDS BIT
8A1A   3200E0                        STA        A1ST ; SAVE LEDS
8A1D                                 RESTOR     PSW
8A1E   C9                            RET
8A1F              ;             IF IN SECONDS
8A1F              TB03
8A1F   3A00E0                        LDA        A1ST ; GET LEDS
8A22   E6F0                          ANI        0F0H ; CLEAR TIME BASE BITS
8A24   F601                          ORI        LD.MSEC ; SET MILLISECONDS BIT
8A26   3200E0                        STA        A1ST ; SAVE LEDS
8A29                                 RESTOR     PSW
8A2A   C9                            RET
8A2B              ;****************************************************************
8A2B              ;
8A2B                                 USE        PRGM
8A2B              ;
8A2B              ;             ROUTINE TO PROMPT FOR A METHOD NUMBER AND STORE METHOD 0
8A2B              ;             IN IT.
8A2B              ;
8A2B   52A20100   MSTMSG            DB         MCODE,SCODE,BLANK^DOT,BLANK,BLANK,BLANK,BLANK,BLANK
       00000000
```

```
8A33                    ;
8A33            SRMSTR   ENTRY
8A33                     MOVE     MSTMSG,DTBUF,8 ; DISPLAY PROMPT
8A43  2109F8             LXI      H,DTBUF ; POINT TO DISPLAY BUFFER
8A46  2239F8             SHLD     INACTIVE
8A49            SMS01
8A49  CD0585             CALL     INPUT ; SEE WHAT TO DO
8A4C  FEC8               CPI      ENTER ; SEE IF TO STORE THE CURRENT BUFFER
8A4E  CA6F8A             JZ       SMS03 ; YES ...
8A51                          SEE IF A COMMAND
8A51                     COMAND   NCOMDS,ROUTNS,COMMDS
8A5C  DA608A             JC       SMS02 ; NO, MUST BE A METHOD NUMBER
8A5F  E9                 PCHL     ; ELSE EXECUTE THE NEW ROUTINE
8A60                    ;
8A60            SMS02
8A60  CD8732             CALL     KB2BIN ; CONVERT TO BINARY
8A63  DA498A             JC       SMS01 ; INVALID
8A66  CDA032             CALL     BIN2DS ; CONVERT TO DISPLAYABLE
8A69  320BF8             STA      DTBUF+2 ; DISPLAY IT
8A6C  C3498A             JMP      SMS01
8A6F                    ;
8A6F            SMS03
8A6F  3A0BF8             LDA      DTBUF+2 ; GET THE CURRENT METHOD NUMBER
8A72  CDAE32             CALL     DS2BIN ; CONVERT TO BINARY
8A75  DA498A             JC       SMS01 ; INVALID
8A78  6F                 MOV      L,A ; BINARY METHOD NUMBER INTO 'HL'
8A79  2600               MVI      H,0
8A7B  AF                 XRA      A ; CLEAR 'A'
8A7C                    ;
8A7C            SMS04
8A7C  C611               ADI      SZ.MTH ; 'A' WILL CONTAIN THE OFFSET
8A7E  2D                 DCR      L ; KEEP TRACK OF METHOD NUMBER
8A7F  C27C8A             JNZ      SMS04 ; IF MORE TO DO
8A82                    ;
8A82  2101C8             LXI      H,IMETHD0 ; POINT TO INTERFACE METHOD STORAGE
8A85  110000             LXI      D,0
8A88  5F                 MOV      E,A
8A89  19                 DAD      D
8A8A                     SAVE     H ; SAVE IT
8A8B  2101D0             LXI      H,PMETHD0 ; POINT TO PROBE METHOD STORAGE
8A8E  010000             LXI      B,0
8A91  4F                 MOV      C,A
8A92  09                 DAD      B
8A93  EB                 XCHG
8A94                    ;
8A94                    ;MOVE PMETHD0,,SZ.MTH ; STORE PMETHD0 IN PMETHDn
8A94  0101D0             LXI      B,PMETHD0
8A97  2E11               MVI      L,SZ.MTH
8A99            SMS05
8A99  0A                 LDAX     B
8A9A  03                 INX      B
8A9B  12                 STAX     D
8A9C  13                 INX      D
8A9D  2D                 DCR      L
8A9E  C2998A             JNZ      SMS05
8AA1                    ;
8AA1                     RESTOR   D ; GET IMETHD PTR
8AA2                    ;MOVE IMETHD0,,SZ.MTH ; STORE IMETHD0 IN IMETHDn
8AA2  0101C8             LXI      B,IMETHD0
8AA5  2E11               MVI      L,SZ.MTH
8AA7            SMS06
8AA7  0A                 LDAX     B
8AA8  03                 INX      B
8AA9  12                 STAX     D
8AAA  13                 INX      D
8AAB  2D                 DCR      L
8AAC  C2A78A             JNZ      SMS06
8AAF                    ;
8AAF  C39482             JMP      MAIN01 ; GO SEE WHAT TO DO
8AB2            ;***********************************************************************
8AB2            ;
8AB2                     USE      PRGM
8AB2            ;
8AB2            ;           ROUTINE TO PROMPT FOR A METHOD NUMBER AND RECALL IT
8AB2            ;
8AB2  52920100  MRCMSG   DB       MCODE,RCODE,BLANK^DOT,BLANK,BLANK,BLANK,BLANK,BLANK
      00000000
8ABA            ;
8ABA            SRMRCL   ENTRY
8ABA                     MOVE     MRCMSG,DTBUF,8 ; DISPLAY PROMPT
8ACA  2109F8             LXI      H,DTBUF ; POINT TO DISPLAY BUFFER
8ACD  2239F8             SHLD     INACTIVE
8AD0            ;
8AD0            SMR01
8AD0  CD0585             CALL     INPUT ; SEE WHAT TO DO
8AD3  FEC8               CPI      ENTER ; SEE IF TO RECALL THE CURRENT BUFFER
8AD5  CAF68A             JZ       SMR03 ; YES ...
8AD8                          SEE IF A COMMAND
8AD8                     COMAND   NCOMDS,ROUTNS,COMMDS
8AE3  DAE78A             JC       SMR02 ; NO, MUST BE A METHOD NUMBER
8AE6  E9                 PCHL     ; ELSE EXECUTE THE NEW ROUTINE
8AE7            ;
8AE7            SMR02
8AE7  CD8732             CALL     KB2BIN ; CONVERT TO BINARY
8AEA  DAD08A             JC       SMR01 ; INVALID
```

```
8AED  CDA032            CALL      BIN2DS ; CONVERT TO DISPLAYABLE
8AF0  320BF8            STA       DTBUF+2 ; DISPLAY IT
8AF3  C3D08A            JMP       SMR01
8AF6              ;
8AF6           SMR03
8AF6  3A0BF8            LDA       DTBUF+2 ; GET THE CURRENT METHOD NUMBER
8AF9  CDAE32            CALL      DS2BIN ; CONVERT TO BINARY
8AFC  DAD08A            JC        SMR01 ; IF NO GOOD
8AFF  6F                MOV       L,A ; BINARY METHOD NUMBER INTO "HL"
8B00  2600              MVI       H,0
8B02  AF                XRA       A ; CLEAR "A"
8B03           SMR04
8B03  C611              ADI       SZ.MTH ; "A" WILL CONTAIN THE OFFSET
8B05  2D                DCR       L ; KEEP TRACK OF METHOD NUMBER
8B06  C2038B            JNZ       SMR04 ; IF MORE TO DO
8B09              ;
8B09  2101C8            LXI       H,IMETHD0 ; POINT TO METHOD STORAGE
8B0C  010000            LXI       B,0
8B0F  4F                MOV       C,A
8B10  09                DAD       B
8B11                    SAVE      H ; SAVE PTR TO INTEFACE METHOD
8B12  2101D0            LXI       H,PMETHD0
8B15  010000            LXI       B,0
8B18  4F                MOV       C,A
8B19  09                DAD       B
8B1A                    SAVE      H
8B1B                    RESTOR    B ; PTR TO PROBE METHOD
8B1C              ;
8B1C              ;MOVE ,PMETHD0,SZ.MTH ; STORE PMETHD0 IN PMETHDn
8B1C  1101D0            LXI       D,PMETHD0
8B1F  2E11              MVI       L,SZ.MTH
8B21           SMR05
8B21  0A                LDAX      B
8B22  03                INX       B
8B23  12                STAX      D
8B24  13                INX       D
8B25  2D                DCR       L
8B26  C2218B            JNZ       SMR05
8B29              ;
8B29                    RESTOR    B
8B2A              ;MOVE ,IMETHD0,SZ.MTH ; STORE IMETHD0 IN METHDn
8B2A  1101C8            LXI       D,IMETHD0
8B2D  2E11              MVI       L,SZ.MTH
8B2F           SMR06
8B2F  0A                LDAX      B
8B30  03                INX       B
8B31  12                STAX      D
8B32  13                INX       D
8B33  2D                DCR       L
8B34  C22F8B            JNZ       SMR06
8B37              ;
8B37  CD0C40            CALL      CALCULATP
8B3A  CD0C50            CALL      CALCULATI
8B3D  C39482            JMP       MAIN01 ; GO SEE WHAT TO DO
8B40  ;*************************************************************
8B40              ;
8B40                    USE       PRGM
8B40              ;
8B40              ;         ROUTINE TO MAINTAIN THE INTERFACE TEMPERATURE
8B40              ;         ENTERED FROM TIMER QUE
8B40              ;
8B40           IFCTMP   ENTRY
8B40  2A18F8            LHLD      ITEMP ; GET THE TEMPERATURE
8B43  29                DAD       H ; TIMES 2 FOR OFFSET
8B44  1100B8            LXI       D,TABLE1 ; POINT TO RTD TABLE
8B47  19                DAD       D ; POINT TO CONVERSION
8B48  5E                MOV       E,M ; GET CONVERSION
8B49  23                INX       H
8B4A  56                MOV       D,M
8B4B  EB                XCHG      ; PUT CONVERSION INTO "HL"
8B4C  2219E0            SHLD      CH1OUT ; SET THE TEMPERATURE
8B4F  CD8334            CALL      VOUT
8B52  C9                RET
8B53  ;*************************************************************
8B53              ;
8B53                    USE       PRGM
8B53              ;
8B53           SRDUMP   ENTRY
8B53  2109F8            LXI       H,DTBUF
8B56  2239F8            SHLD      INACTIVE
8B59                    FILL      DTBUF,BLANK,8
8B66  CD0585            CALL      INPUT
8B69  CD1F8C            CALL      KB2HEX
8B6C  3209F8            STA       DTBUF
8B6F  CD0585            CALL      INPUT
8B72  CD1F8C            CALL      KB2HEX
8B75  320AF8            STA       DTBUF+1
8B78  CD0585            CALL      INPUT
8B7B  CD1F8C            CALL      KB2HEX
8B7E  320BF8            STA       DTBUF+2
8B81  CD0585            CALL      INPUT
8B84  CD1F8C            CALL      KB2HEX
8B87  320CF8            STA       DTBUF+3
8B8A  0109F8            LXI       B,DTBUF
8B8D  CD348C            CALL      HEX2BIN
```

```
8B90  67              MOV     H,A
8B91  CD348C          CALL    HEX2BIN
8B94  6F              MOV     L,A
8B95          SRD01
8B95  7C              MOV     A,H
8B96  0109F8          LXI     B,DTBUF
8B99  CDEA8B          CALL    DISBYT
8B9C  7D              MOV     A,L
8B9D  CDEA8B          CALL    DISBYT
8BA0  7E              MOV     A,M
8BA1  010FF8          LXI     B,DTBUF+6
8BA4  CDEA8B          CALL    DISBYT
8BA7  CD0585          CALL    INPUT
8BAA  FEC8            CPI     0C8H
8BAC  CAD28B          JZ      SRD02
8BAF  FEC9            CPI     0C9H
8BB1  CAD68B          JZ      SRD03
8BB4  FEF7            CPI     FY.DUMP
8BB6  CADA8B          JZ      SRD10
8BB9  CD1F8C          CALL    KB2HEX
8BBC  320FF8          STA     DTBUF+6
8BBF  CD0585          CALL    INPUT
8BC2  CD1F8C          CALL    KB2HEX
8BC5  3210F8          STA     DTBUF+7
8BC8  010FF8          LXI     B,DTBUF+6
8BCB  CD348C          CALL    HEX2BIN
8BCE  77              MOV     M,A
8BCF  C3958B          JMP     SRD01
8BD2          SRD02
8BD2  23              INX     H
8BD3  C3958B          JMP     SRD01
8BD6          SRD03
8BD6  2B              DCX     H
8BD7  C3958B          JMP     SRD01
8BDA          SRD10
8BDA                  FILL    DTBUF,BLANK,8
8BE7  C39482          JMP     MAIN01
8BEA          DISBYT
8BEA                  SAVE    PSW
8BEB  E6F0            ANI     0F0H
8BED  0F              RRC
8BEE  0F              RRC
8BEF  0F              RRC
8BF0  0F              RRC
8BF1  CD598C          CALL    HEX2DS
8BF4  02              STAX    B
8BF5  03              INX     B
8BF6                  RESTOR  PSW
8BF7  E60F            ANI     00FH
8BF9  CD598C          CALL    HEX2DS
8BFC  02              STAX    B
8BFD  03              INX     B
8BFE  C9              RET
8BFF  E9F2F1F0  KBCHAR  DB    0E9H,0F2H,0F1H,0F0H,0C2H,0C1H,0C0H,0D2H,0D1H,0D0H,0F4H,0F3H
      C2C1C0D2
      D1D0F4F3
8C0B  C4C3D4D3        DB      0C4H,0C3H,0D4H,0D3H
8C0F  10203040  HEXCHAR DB    CODE0,CODE1,CODE2,CODE3,CODE4,CODE5,CODE6,CODE7,CODE8
      50607080
      90
8C18  A0B0C0D0        DB      CODE9,ACODE,BCODE,CCODE,DCODE,ECODE,FCODE
      E0F002
8C1F          KB2HEX
8C1F                  SAVE    H,B
8C21  010F8C          LXI     B,HEXCHAR
8C24  21FF8B          LXI     H,KBCHAR
8C27          KH01
8C27  BE              CMP     M
8C28  CA308C          JZ      KH02
8C2B  03              INX     B
8C2C  23              INX     H
8C2D  C3278C          JMP     KH01
8C30          KH02
8C30  0A              LDAX    B
8C31                  RESTOR  B,H
8C33  C9              RET
8C34          HEX2BIN
8C34                  SAVE    H
8C35  0A              LDAX    B
8C36  FE02            CPI     2
8C38  C2408C          JNZ     HB01
8C3B  3EF0            MVI     A,0F0H
8C3D  C3428C          JMP     HB02
8C40          HB01
8C40  D610            SUI     010H
8C42          HB02
8C42  67              MOV     H,A
8C43  03              INX     B
8C44  0A              LDAX    B
8C45  FE02            CPI     2
8C47  C24F8C          JNZ     HB03
8C4A  3E0F            MVI     A,00FH
8C4C  C3558C          JMP     HB04
8C4F          HB03
8C4F  D610            SUI     010H
```

```
8C51  0F                     RRC
8C52  0F                     RRC
8C53  0F                     RRC
8C54  0F                     RRC
8C55              HB04
8C55  B4                     ORA      H
8C56  03                     INX      B
8C57                         RESTOR   H
8C58  C9                     RET
8C59              HEX2DS
8C59                         SAVE     H
8C5A  210F8C                 LXI      H,HEXCHAR
8C5D  110000                 LXI      D,0
8C60  5F                     MOV      E,A
8C61  19                     DAD      D
8C62  7E                     MOV      A,M
8C63                         RESTOR   H
8C64  C9                     RET
8C65              ;****************************************************************
8C65              SROUT       ENTRY
8C65  2109F8                 LXI      H,DTBUF
8C68  2239F8                 SHLD     INACTIVE
8C6B                         FILL     DTBUF,BLANK,8
8C78              SR001
8C78  CD0585                 CALL     INPUT
8C7B  F5                     PUSH     PSW
8C7C                         FILL     DTBUF,BLANK,8
8C89  F1                     POP      PSW
8C8A  FEE3                   CPI      KY.OUTPT
8C8C  CA9482                 JZ       MAIN01
8C8F  CD1F8C                 CALL     KB2HEX
8C92  320CF8                 STA      DTBUF+3
8C95  CD0585                 CALL     INPUT
8C98  CD1F8C                 CALL     KB2HEX
8C9B  320DF8                 STA      DTBUF+4
8C9E  CD0585                 CALL     INPUT
8CA1  CD1F8C                 CALL     KB2HEX
8CA4  320FF8                 STA      DTBUF+6
8CA7  CD0585                 CALL     INPUT
8CAA  CD1F8C                 CALL     KB2HEX
8CAD  3210F8                 STA      DTBUF+7
8CB0  3ED3                   MVI      A,0D3H
8CB2  32CDC8                 STA      SCRATCH
8CB5  010CF8                 LXI      B,DTBUF+3
8CB8  CD348C                 CALL     HEX2BIN
8CBB  32CEC8                 STA      SCRATCH+1
8CBE  3EC9                   MVI      A,0C9H
8CC0  32CFC8                 STA      SCRATCH+2
8CC3  010FF8                 LXI      B,DTBUF+6
8CC6  CD348C                 CALL     HEX2BIN
8CC9  21CDC8                 LXI      H,SCRATCH
8CCC  CD6130                 CALL     INDRCT
8CCF  C3788C                 JMP      SR001
8CD2              ;****************************************************************
8CD2              SRINP       ENTRY
8CD2  2109F8                 LXI      H,DTBUF
8CD5  2239F8                 SHLD     INACTIVE
8CD8                         FILL     DTBUF,BLANK,8
8CE5              SRIN01
8CE5  CD0585                 CALL     INPUT
8CE8  F5                     PUSH     PSW
8CE9                         FILL     DTBUF,BLANK,8
8CF6  F1                     POP      PSW
8CF7  FEDB                   CPI      KY.INPT
8CF9  CA9482                 JZ       MAIN01
8CFC  CD1F8C                 CALL     KB2HEX
8CFF  320CF8                 STA      DTBUF+3
8D02  CD0585                 CALL     INPUT
8D05  CD1F8C                 CALL     KB2HEX
8D08  320DF8                 STA      DTBUF+4
8D0B  3EDB                   MVI      A,0DBH
8D0D  32CDC8                 STA      SCRATCH
8D10  010CF8                 LXI      B,DTBUF+3
8D13  CD348C                 CALL     HEX2BIN
8D16  32CEC8                 STA      SCRATCH+1
8D19  3EC9                   MVI      A,0C9H
8D1B  32CFC8                 STA      SCRATCH+2
8D1E  21CDC8                 LXI      H,SCRATCH
8D21  CD6130                 CALL     INDRCT
8D24  010FF8                 LXI      B,DTBUF+6
8D27  CDEA8B                 CALL     DISBYT
8D2A  C3E58C                 JMP      SRIN01
8D2D              ;****************************************************************
8D2D  D0B04200   CALMSG       DB       CCODE,ACODE,LCODE,BLANK,BLANK^DOT,BLANK^DOT,BLANK^DOT,BLANK^DOT
      01010101
8D35              SRCAL       ENTRY
8D35                         MOVE     CALMSG,DTBUF,8
8D45  2109F8                 LXI      H,DTBUF
8D48  2239F8                 SHLD     INACTIVE
8D4B              SRC01
8D4B  CD0585                 CALL     INPUT
8D4E  FECB                   CPI      KY.DSPLY
8D50  CA098E                 JZ       SRC09
8D53                         COMAND   NCOMDS,ROUTNS,COMMDS ; SEE IF A COMMAND
8D5E  D2218E                 JNC      SRC90
```

```
8D61  CD8732           CALL    KB2BIN
8D64  D26D8D           JNC     SRC02   ; IF A VALID NUMBER
8D67  CD7A33           CALL    BEEP2
8D6A  C34B8D           JMP     SRC01
8D6D          SRC02
8D6D  CDA032           CALL    BIN2DS
8D70  320DF8           STA     DTBUF+4
8D73          SRC03
8D73  CD0585           CALL    INPUT
8D76  FECB             CPI     KY.DSPLY
8D78  CA098E           JZ      SRC09
8D7B                   COMAND  NCOMDS,ROUTNS,COMMDS ; SEE IF A COMMAND
8D86  D2218E           JNC     SRC90
8D89  CD8732           CALL    KB2BIN
8D8C  D2958D           JNC     SRC04   ; IF A VALID NUMBER
8D8F  CD7A33           CALL    BEEP2
8D92  C3738D           JMP     SRC03
8D95          SRC04
8D95  CDA032           CALL    BIN2DS
8D98  320EF8           STA     DTBUF+5
8D9B          SRC05
8D9B  CD0585           CALL    INPUT
8D9E  FECB             CPI     KY.DSPLY
8DA0  CA098E           JZ      SRC09
8DA3                   COMAND  NCOMDS,ROUTNS,COMMDS ; SEE IF A COMMAND
8DAE  D2218E           JNC     SRC90
8DB1  CD8732           CALL    KB2BIN
8DB4  D2BD8D           JNC     SRC06   ; IF A VALID NUMBER
8DB7  CD7A33           CALL    BEEP2
8DBA  C3B98D           JMP     SRC05
8DBD          SRC06
8DBD  CDA032           CALL    BIN2DS
8DC0  320FF8           STA     DTBUF+6
8DC3          SRC07
8DC3  CD0585           CALL    INPUT
8DC6  FECB             CPI     KY.DSPLY
8DC8  CA098E           JZ      SRC09
8DCB                   COMAND  NCOMDS,ROUTNS,COMMDS ; SEE IF A COMMAND
8DD6  D2218E           JNC     SRC90
8DD9  CD8732           CALL    KB2BIN
8DDC  D2E58D           JNC     SRC08   ; IF A VALID NUMBER
8DDF  CD7A33           CALL    BEEP2
8DE2  C3C38D           JMP     SRC07
8DE5          SRC08
8DE5  CDA032           CALL    BIN2DS
8DE8  3210F8           STA     DTBUF+7
8DEB  010DF8           LXI     B,DTBUF+4
8DEE  CD6A31           CALL    CNVRT4
8DF1  CD8831           CALL    PK2BIN
8DF4                   SAVE    H
8DF5  1198FB           LXI     D,"1127
8DF8  19               DAD     D
8DF9                   RESTOR  H
8DFA  DA358D           JC      SRCAL
8DFD                   SAVE    H
8DFE  1196FC           LXI     D,"873
8E01  19               DAD     D
8E02                   RESTOR  H
8E03  D2358D           JNC     SRCAL
8E06  229FF8           SHLD    CALPROBE
8E09          SRC09
8E09  2A9FF8           LHLD    CALPROBE
8E0C                   SAVE    H
8E0D  CD1532           CALL    BIN2PK
8E10  010DF8           LXI     B,DTBUF+4
8E13  CD3431           CALL    PRVRT4
8E16                   RESTOR  H
8E17  1198FC           LXI     D,"871
8E1A  19               DAD     D
8E1B  7D               MOV     A,L
8E1C  D332             OUT     CAL.PORT
8E1E  C39482           JMP     MAIN01
8E21          SRC90
8E21  E9               PCHL
8E22          ;****************************************************************
8E22  0000B032  AIRMSG DB      BLANK,BLANK,ACODE,ICODE,RCODE,NCODE,ICODE,TCODE
      926232B2
8E2A  000022F0  HELMSG DB      BLANK,BLANK,HCODE,ECODE,LCODE,ICODE,UCODE,MCODE
      4232C252
8E32  0000D2B0  VACMSG DB      BLANK,BLANK,VCODE,ACODE,CCODE,UCODE,UCODE,MCODE
      D0C2C252
8E3A          SRGCF    ENTRY
8E3A  2109F8           LXI     H,DTBUF
8E3D  2239F8           SHLD    INACTIVE
8E40  3AA1F8           LDA     GASFACTOR
8E43  FE01             CPI     1
8E45  C2D58E           JNZ     SRG01
8E48                   MOVE    AIRMSG,DTBUF,8
8E58  3E80             MVI     A,AIR.FCTR
8E5A  C3998E           JMP     SRG20
8E5D          SRG01
8E5D  FE02             CPI     2
8E5F  C2778E           JNZ     SRG02
8E62                   MOVE    HELMSG,DTBUF,8
8E72  3E80             MVI     A,HEL.FCTR
```

```
8E74   C3998E                    JMP         SRG20
8E77             SRG02
8E77   FE03                      CPI         3
8E79   C2918E                    JNZ         SRG03
8E7C                              MOVE        VACMSG,DTBUF,8
8E8C   3E80                      MVI         A,VAC.FCTR
8E8E   C3998E                    JMP         SRG20
8E91             SRG03
8E91   3E01                      MVI         A,1
8E93   32A1F8                    STA         GASFACTOR
8E96   C33A8E                    JMP         SRGCF
8E99             SRG20
8E99   D331                      OUT         GAS.PORT
8E9B   CD0585                    CALL        INPUT
8E9E   FEDA                      CPI         KY.GCF
8EA0   CAB28E                    JZ          SRG30
8EA3                              COMAND      NCOMDS,ROUTNS,COMMDS
8EAE   DA998E                    JC          SRG20
8EB1   E9                        PCHL
8EB2             SRG30
8EB2   3AA1F8                    LDA         GASFACTOR
8EB5   3C                        INR         A
8EB6   FE04                      CPI         4
8EB8   F2918E                    JP          SRG03
8EBB   32A1F8                    STA         GASFACTOR
8EBE   C33A8E                    JMP         SRGCF
8EC1         ;*********************************************************************
8EC1                              END
8EC1         ;*********************************************************************
8EC1                              USE         EPROM4
4000             EPINT
4000   C30F40                    JMP         PRBSTRT
4003             EPXIT
4003   C32E49                    JMP         PRBXIT
4006             EPTIM
4006   C31449                    JMP         PRBTIM
4009             INPTMP
4009   C39049                    JMP         PRBHOME
400C             CALCULATP
400C   C32A40                    JMP         PRBCALC
400F         ;           SET UP PROBE ROUTINES AND DO PRELIMINARY CALCULATIONS
400F             PRBSTRT          ENTRY
400F   CD0C40                    CALL        CALCULATP
4012   2A02D0                    LHLD        PMETHD0+OF.INT+1 ; GET INITIAL TEMP
4015                              SETEMP      H
4026   2A5EF8                    LHLD        PSTACK ; GET FIRST ROUTINE
4029   E9                        PCHL        ; EXECUTE IT
402A         ;
402A         ;      DO ALL PRELIMINARY CALCULATIONS
402A         ;
402A             PRBCALC          ENTRY
402A         ;*********************************************************************
402A         ;           FOR TEST PURPOSES ONLY
402A                              MOVE        TSTRATES,R1.CBLK+23,16
403A                              MOVE        TSTRATES,R2.CBLK+23,16
404A         ;*********************************************************************
404A                              FILL        PSTACK,0,12 ; CLEAR EXECUTION STACK
4057         ;                    INITIAL
4057   3A01D0                    LDA         PMETHD0+OF.INT
405A   E601                      ANI         LD.MSEC ; SEE IF FAST TIME
405C   CA6540                    JZ          PBS01
405F   21FA42                    LXI         H,FPLVL1
4062   C36840                    JMP         PBS02
4065             PBS01
4065   21BC41                    LXI         H,SPLVL1
4068             PBS02
4068   225EF8                    SHLD        PSTACK
406B         ;                    RAMP1
406B             PBS10
406B                              MOVE        R1.CBLK,R.CBLK,SZ.RCBLK
407B   2A02D0                    LHLD        PMETHD0+OF.INT+1 ; GET START TEMP
407E   EB                        XCHG
407F   2A08D0                    LHLD        PMETHD0+OF.HD1+1 ; GET END TEMP
4082                              DR2CM       D
4089   19                        DAD         D ; GET DIFFERENCE
408A   7D                        MOV         A,L ; SEE IF 0
408B   B4                        ORA         H
408C   CAE140                    JZ          PBS14 ; YES, NOT IMPLEMENTED
408F   3A06D0                    LDA         PMETHD0+OF.RP1 ; GET RAMP RATE
4092   FE1A                      CPI         NPRATES-1 ; SEE IF FASTEST
4094   C2B940                    JNZ         PBS10.5 ; NO ...
4097   2A02D0                    LHLD        PMETHD0+OF.INT+1 ; GET START TEMP
409A   7D                        MOV         A,L ; SEE IF 0
409B   B4                        ORA         H
409C   CAA640                    JZ          PBS10.1 ; YES ...
409F   2A08D0                    LHLD        PMETHD0+OF.HD1+1 ; GET END TEMP
40A2   19                        DAD         D ; SEE IF NEGATIVE SLOPE
40A3   D2B940                    JNC         PBS10.5 ; YES ...
40A6             PBS10.1
40A6   2A02D0                    LHLD        PMETHD0+OF.INT+1 ; GET START TEMP
40A9   EB                        XCHG
40AA   2A08D0                    LHLD        PMETHD0+OF.HD1+1 ; GET END TEMP
40AD   3A06D0                    LDA         PMETHD0+OF.RP1 ; GET RAMP RATE
40B0   CD424A                    CALL        VFRAMP ; GO SET UP VERY FAST RAMP
40B3   210846                    LXI         H,VFPRMP1 ; EXECUTION ROUTINE
```

```
40B6  C3E940              JMP      PBS12
40B9          PBS10.5
40B9  3A06D0              LDA      PMETHD0+OF.RP1 ; GET RAMP RATE
40BC  FE11                CPI      NSPRATES ; SEE IF FAST RAMP
40BE  FAD140              JM       PBS11 ; NO ...
40C1  2A02D0              LHLD     PMETHD0+OF.INT+1 ; GET START TEMP
40C4  EB                  XCHG
40C5  2A08D0              LHLD     PMETHD0+OF.HD1+1 ; GET END TEMP
40C8  CDFA49              CALL     FRAMP ; SET UP FAST RAMP
40CB  211E45              LXI      H,FPRMP1 ; EXECUTION ROUTINE
40CE  C3E940              JMP      PBS12
40D1          PBS11
40D1  2A02D0              LHLD     PMETHD0+OF.INT+1 ; GET START TEMP
40D4  EB                  XCHG
40D5  2A08D0              LHLD     PMETHD0+OF.HD1+1 ; GET END TEMP
40D8  CDB149              CALL     SRAMP ; SET UP SLOW RAMP
40DB  210F44              LXI      H,SPRMP1 ; EXECUTION ROUTINE
40DE  C3E940              JMP      PBS12
40E1          PBS14
40E1  3EFF                MVI      A,0FFH
40E3  3293F8              STA      R.IMPL
40E6  210F44              LXI      H,SPRMP1
40E9          PBS12
40E9  2260F8              SHLD     PSTACK+2
40EC                      MOVE     R.CBLK,R1.CBLK,SZ.RCBLK
40FC          ;                    HOLD1
40FC          PBS20
40FC  3A07D0              LDA      PMETHD0+OF.HD1
40FF  E601                ANI      LD.MSEC ; SEE IF FAST TIME
4101  CA0A41              JZ       PBS21
4104  212943              LXI      H,FPLVL2
4107  C30D41              JMP      PBS22
410A          PBS21
410A  21EB41              LXI      H,SPLVL2
410D          PBS22
410D  2262F8              SHLD     PSTACK+4
4110          ;                    RAMP2
4110          PBS30
4110                      MOVE     R2.CBLK,R.CBLK,SZ.RCBLK
4120  2A08D0              LHLD     PMETHD0+OF.HD1+1 ; GET START TEMP
4123  EB                  XCHG
4124  2A0ED0              LHLD     PMETHD0+OF.FNL+1 ; GET END TEMP
4127                      DR2CM    D
412E  19                  DAD      D ; GET DIFFERENCE
412F  7D                  MOV      A,L ; SEE IF 0
4130  B4                  ORA      H
4131  CA8641              JZ       PBS34 ; YES, NOT IMPLEMENTED
4134  3A0CD0              LDA      PMETHD0+OF.RP2 ; GET RAMP RATE
4137  FE1A                CPI      NPRATES-1 ; SEE IF FASTEST
4139  C25E41              JNZ      PBS30.5 ; NO ...
413C  2A08D0              LHLD     PMETHD0+OF.HD1+1 ; GET START TEMP
413F  7D                  MOV      A,L ; SEE IF 0
4140  B4                  ORA      H
4141  CA4B41              JZ       PBS30.1 ; YES ...
4144  2A0ED0              LHLD     PMETHD0+OF.FNL+1 ; GET END TEMP
4147  19                  DAD      D ; SEE IF NEGATIVE SLOPE
4148  D25E41              JNC      PBS30.5 ; YES ...
414B          PBS30.1
414B  2A08D0              LHLD     PMETHD0+OF.HD1+1 ; GET START TEMP
414E  EB                  XCHG
414F  2A0ED0              LHLD     PMETHD0+OF.FNL+1 ; GET END TEMP
4152  3A0CD0              LDA      PMETHD0+OF.RP2 ; GET RAMP RATE
4155  CD424A              CALL     VFRAMP ; GO SET UP VERY FAST RAMP
4158  213746              LXI      H,VFPRMP2 ; EXECUTION ROUTINE
415B  C38E41              JMP      PBS32
415E          PBS30.5
415E  3A0CD0              LDA      PMETHD0+OF.RP2 ; GET RAMP RATE
4161  FE11                CPI      NSPRATES ; SEE IF FAST RAMP
4163  FA7641              JM       PBS31 ; NO ...
4166  2A08D0              LHLD     PMETHD0+OF.HD1+1 ; GET START TEMP
4169  EB                  XCHG
416A  2A0ED0              LHLD     PMETHD0+OF.FNL+1 ; GET END TEMP
416D  CDFA49              CALL     FRAMP ; SET UP FAST RAMP
4170  215A45              LXI      H,FPRMP2 ; EXECUTION ROUTINE
4173  C38E41              JMP      PBS32
4176          PBS31
4176  2A08D0              LHLD     PMETHD0+OF.HD1+1 ; GET START TEMP
4179  EB                  XCHG
417A  2A0ED0              LHLD     PMETHD0+OF.FNL+1 ; GET END TEMP
417D  CDB149              CALL     SRAMP ; SET UP SLOW RAMP
4180  214B44              LXI      H,SPRMP2 ; EXECUTION ROUTINE
4183  C38E41              JMP      PBS32
4186          PBS34
4186  3EFF                MVI      A,0FFH
4188  3293F8              STA      R.IMPL
418B  214B44              LXI      H,SPRMP2
418E          PBS32
418E  2264F8              SHLD     PSTACK+6
4191                      MOVE     R.CBLK,R2.CBLK,SZ.RCBLK
41A1          ;                    FINAL
41A1          PBS40
41A1  3A0DD0              LDA      PMETHD0+OF.FNL
41A4  E601                ANI      LD.MSEC ; SEE IF FAST TIME
41A6  CAAF41              JZ       PBS41
41A9  215A43              LXI      H,FPLVL3
```

```
41AC  C3B241              JMP      PBS42
41AF              PBS41
41AF  211C42              LXI      H,SPLVL3
41B2              PBS42
41B2  2266F8              SHLD     PSTACK+8
41B5            ;              EXIT
41B5              PBS50
41B5  212E49              LXI      H,PRBXIT
41B8  2268F8              SHLD     PSTACK+10
41BB  C9                  RET
41BC            ;***********************************************************
41BC            ;
41BC            ;              SLOW LEVEL INTERVAL ROUTINE
41BC            ;
41BC            ;      INITIAL TIME/TEMP
41BC              SPLVL1
41BC  2A04D0              LHLD     PMETHD0+OF.INT+3 ; SEE IF IMPLEMENTED
41BF  7D                  MOV      A,L
41C0  B4                  ORA      H
41C1  C2C841              JNZ      SPLVL1.1 ; YES, GO EXECUTE IT
41C4  2A60F8              LHLD     PSTACK+2 ; ELSE, GET NEXT STEP
41C7  E9                  PCHL     ; GO EXECUTE
41C8              SPLVL1.1
41C8  2A60F8              LHLD     PSTACK+2 ; GET NEXT ROUTINE
41CB  223DF8              SHLD     PNEXT
41CE  2E32                MVI      L,ICODE ; TELL WHICH STEP
41D0  2662                MVI      H,NCODE
41D2  222FF8              SHLD     PACTBUF
41D5  2101D0              LXI      H,PMETHD0+OF.INT ; POINT TO INITIAL TIME/TEMP
41D8  3A02E0              LDA      C1ST
41DB  F610                ORI      LD.INTH
41DD  3202E0              STA      C1ST
41E0  3A01E0              LDA      B1ST
41E3  E6D7                ANI      "(LD.FTMP1+LD.FTMP2)
41E5  3201E0              STA      B1ST
41E8  C34D42              JMP      SPRB01
41EB            ;      HOLD 1 TIME/TEMP
41EB              SPLVL2
41EB  2A0AD0              LHLD     PMETHD0+OF.HD1+3 ; SEE IF IMPLEMENTED
41EE  7D                  MOV      A,L
41EF  B4                  ORA      H
41F0  C2F741              JNZ      SPLVL2.1 ; YES, GO EXECUTE
41F3  2A64F8              LHLD     PSTACK+6 ; ELSE, GET NEXT ROUTINE
41F6  E9                  PCHL     ; GO EXECUTE IT
41F7              SPLVL2.1
41F7  2A64F8              LHLD     PSTACK+6 ; GET NEXT ROUTINE
41FA  223DF8              SHLD     PNEXT
41FD  2E22                MVI      L,HCODE ; TELL WHICH STEP
41FF  2620                MVI      H,CODE1
4201  222FF8              SHLD     PACTBUF
4204  2107D0              LXI      H,PMETHD0+OF.HD1 ; POINT TO HOLD1 TIME/TEMP
4207  3A01E0              LDA      B1ST
420A  F620                ORI      LD.FTMP1
420C  E6F7                ANI      "LD.FTMP2
420E  3201E0              STA      B1ST
4211  3A02E0              LDA      C1ST
4214  E6EF                ANI      "LD.INTH
4216  3202E0              STA      C1ST
4219  C34D42              JMP      SPRB01
421C            ;      FINAL TIME/TEMP
421C              SPLVL3
421C  2A10D0              LHLD     PMETHD0+OF.FNL+3 ; SEE IF IMPLEMENTED
421F  7D                  MOV      A,L
4220  B4                  ORA      H
4221  C22842              JNZ      SPLVL3.1 ; YES, GO EXECUTE
4224  2A68F8              LHLD     PSTACK+10 ; ELSE, GET NEXT ROUTINE
4227  E9                  PCHL     ; GO EXECUTE IT
4228              SPLVL3.1
4228  2A68F8              LHLD     PSTACK+10 ; GET NEXT ROUTINE
422B  223DF8              SHLD     PNEXT
422E  2E02                MVI      L,FCODE ; TELL WHICH STEP
4230  2632                MVI      H,ICODE
4232  222FF8              SHLD     PACTBUF
4235  210DD0              LXI      H,PMETHD0+OF.FNL ; POINT TO FINAL TIME/TEMP
4238  3A01E0              LDA      B1ST
423B  F608                ORI      LD.FTMP2
423D  E6DF                ANI      "LD.FTMP1
423F  3201E0              STA      B1ST
4242  3A02E0              LDA      C1ST
4245  E6EF                ANI      "LD.INTH
4247  3202E0              STA      C1ST
424A  C34D42              JMP      SPRB01
424D            ;      COMMON CODE
424D              SPRB01
424D  3A01E0              LDA      B1ST
4250  E6BF                ANI      "LD.RMP2
4252  3201E0              STA      B1ST
4255  3A02E0              LDA      C1ST
4258  E6FE                ANI      "LD.RMP1
425A  3202E0              STA      C1ST
425D                      SAVE     H
425E                      FILL     PACTBUF+5,CODE0,3
426B  210000              LXI      H,0 ; ZERO RUN TIME
426E  223FF8              SHLD     PRTIME
4271                      RESTOR   H
```

```
4272  3A00E0              LDA      A1ST ; GET TIME BASE LEDS
4275  E6F0                ANI      0F0H
4277  B6                  ORA      M ; SET CURRENT LED
4278  3200E0              STA      A1ST ; SAVE LEDS
427B  23                  INX      H ; POINT TO TEMPERATURE
427C  5E                  MOV      E,M ; GET THE LO BYTE
427D  23                  INX      H
427E  56                  MOV      D,M ; GET HI BYTE
427F  EB                  XCHG     ; PUT TEMP INTO HL
4280  2241F8              SHLD     PTEMP
4283  CD1532              CALL     BIN2PK
4286  0131F8              LXI      B,PACTBUF+2
4289  CD3031              CALL     PRVRT3
428C  EB                  XCHG
428D  23                  INX      H ; POINT TO TIME
428E  5E                  MOV      E,M ; GET LO BYTE
428F  23                  INX      H
4290  56                  MOV      D,M ; GET HI BYTE
4291  7B                  MOV      A,E
4292  B2                  ORA      D
4293  C29A42              JNZ      SPRB01.5
4296  2A3DF8              LHLD     PNEXT
4299  E9                  PCHL
429A              SPRB01.5
429A  EB                  XCHG     ; PUT TIME INTO 'HL'
429B  2B                  DCX      H
429C  223BF8              SHLD     PELAPSE ; SAVE TIME TO RUN
429F  3A00E0              LDA      A1ST ; GET TIME BASE
42A2  E604                ANI      LD.MIN ; MINUTES ?
42A4  C2C842              JNZ      SPRB02 ; YES ...
42A7  3A00E0              LDA      A1ST
42AA  E608                ANI      LD.HOUR ; HOURS ?
42AC  C2E142              JNZ      SPRB03 ; YES ...
42AF          ;                SECONDS
42AF                      TIMER    10,10,PRBTIM,CBLK14
42C7  C9                  RET
42C8          ;                MINUTES
42C8              SPRB02
42C8                      TIMER    600,600,PRBTIM,CBLK14
42E0  C9                  RET
42E1          ;                HOURS
42E1              SPRB03
42E1                      TIMER    36000,36000,PRBTIM,CBLK14
42F9  C9                  RET
42FA  ;***********************************************************************
42FA          ;           FAST LEVEL INTERVAL ROUTINE
42FA          ;               INITIAL TIME/TEMP
42FA              FPLVL1
42FA  2A04D0              LHLD     PMETHD0+OF.INT+3 ; SEE IF IMPLEMENTED
42FD  7D                  MOV      A,L
42FE  B4                  ORA      H
42FF  C20643              JNZ      FPLVL1.1 ; YES, GO EXECUTE IT
4302  2A60F8              LHLD     PSTACK+2 ; ELSE, GET NEXT STEP
4305  E9                  PCHL     ; GO EXECUTE
4306              FPLVL1.1
4306  2A60F8              LHLD     PSTACK+2 ; GET NEXT ROUTINE
4309  2296F8              SHLD     TNEXT
430C  2E32                MVI      L,ICODE ; TELL WHICH STEP
430E  2662                MVI      H,NCODE
4310  222FF8              SHLD     PACTBUF
4313  2101D0              LXI      H,PMETHD0+OF.INT ; POINT TO INITIAL TIME/TEMP
4316  3A02E0              LDA      C1ST
4319  F610                ORI      LD.INTH
431B  3202E0              STA      C1ST
431E  3A01E0              LDA      B1ST
4321  E6D7                ANI      "(LD.FTMP1+LD.FTMP2)
4323  3201E0              STA      B1ST
4326  C38B43              JMP      FLVL01
4329          ;           HOLD 1 TIME/TEMP ROUTINE
4329              FPLVL2
4329  2A0AD0              LHLD     PMETHD0+OF.HD1+3 ; SEE IF IMPLEMENTED
432C  7D                  MOV      A,L
432D  B4                  ORA      H
432E  C23543              JNZ      FPLVL2.1 ; YES, GO EXECUTE
4331  2A64F8              LHLD     PSTACK+6 ; ELSE, GET NEXT ROUTINE
4334  E9                  PCHL     ; GO EXECUTE IT
4335              FPLVL2.1
4335  2A64F8              LHLD     PSTACK+6 ; GET NEXT ROUTINE
4338  2296F8              SHLD     TNEXT
433B  2E22                MVI      L,HCODE ; TELL WHICH STEP
433D  2620                MVI      H,CODE1
433F  222FF8              SHLD     PACTBUF
4342  2107D0              LXI      H,PMETHD0+OF.HD1 ; POINT TO HOLD1 TIME/TEMP
4345  3A01E0              LDA      B1ST
4348  F620                ORI      LD.FTMP1
434A  E6F7                ANI      "LD.FTMP2;
434C  3201E0              STA      B1ST
434F  3A02E0              LDA      C1ST
4352  E6EF                ANI      "LD.INTH
4354  3202E0              STA      C1ST
4357  C38B43              JMP      FLVL01
435A          ;           FINAL TIME/TEMP ROUTINE
435A              FPLVL3
435A  2A10D0              LHLD     PMETHD0+OF.FNL+3 ; SEE IF IMPLEMENTED
```

```
435D  7D                    MOV      A,L
435E  B4                    ORA      H
435F  C26643                JNZ      FPLVL3.1 ; YES, GO EXECUTE
4362  2A68F8                LHLD     PSTACK+10 ; ELSE, GET NEXT ROUTINE
4365  E9                    PCHL     ; GO EXECUTE IT
4366            FPLVL3.1
4366  2A68F8                LHLD     PSTACK+10 ; GET NEXT ROUTINE
4369  2296F8                SHLD     TNEXT
436C  2E02                  MVI      L,FCODE ; TELL WHICH STEP
436E  2632                  MVI      H,ICODE
4370  222FF8                SHLD     PACTBUF
4373  210DD0                LXI      H,PMETHDO+OF.FNL ; POINT TO FINAL TIME/TEMP
4376  3A01E0                LDA      B1ST
4379  F608                  ORI      LD.FTMP2
437B  E6DF                  ANI      "LD.FTMP1
437D  3201E0                STA      B1ST
4380  3A02E0                LDA      C1ST
4383  E6EF                  ANI      "LD.INTH
4385  3202E0                STA      C1ST
4388  C38B43                JMP      FLVL01
438B            ;                    COMMON CODE
438B            FLVL01
438B  3A01E0                LDA      B1ST
438E  E6BF                  ANI      "LD.RMP2
4390  3201E0                STA      B1ST
4393  3A02E0                LDA      C1ST
4396  E6FE                  ANI      "LD.RMP1
4398  3202E0                STA      C1ST
439B  23                    INX      H ; POINT TO TEMP
439C  5E                    MOV      E,M ; PUT TEMP INTO 'DE'
439D  23                    INX      H
439E  56                    MOV      D,M
439F  23                    INX      H ; POINT TO TIME
43A0  EB                    XCHG     ; PUT TEMP INTO 'HL'
43A1  CD1532                CALL     BIN2PK
43A4  0131F8                LXI      B,PACTBUF+2
43A7  CD3031                CALL     PRVRT3
43AA  EB                    XCHG     ; PUT POINTER INTO 'HL'
43AB  7E                    MOV      A,M ; USE 'A' TO SEE IF '0'
43AC  5F                    MOV      E,A ; USE 'DE' FOR DELAY
43AD  23                    INX      H
43AE  B6                    ORA      M
43AF  C2B643                JNZ      FLVL02 ; IF DELAY IS NOT ZERO
43B2  2A96F8                LHLD     TNEXT ; ELSE, GO DO NEXT ROUTINE
43B5  E9                    PCHL
43B6            FLVL02
43B6  56                    MOV      D,M
43B7                        DELAY    D
43CB                        FILL     PACTBUF+5,CODE0,3
43D8  C9                    RET
43D9            ;****************************************************************
43D9            ;
43D9            ;                    EXECUTE A RAMP PROBE STEP (RAMP1, RAMP2)
43D9            ;            ENTERED FROM TIMER QUE
43D9            PINTVL
43D9  60EA3075  SPINTVL      DW       60000,30000,12000,6000,3000,1200,600,300
      E02E7017
      B80BB004
      58022C01
43E9  78003C00               DW       120,60,30,20,15,10,5,3,2
      1E001400
      0F000A00
      05000300
      0200
43FB  BA45DD22  FPINTVL      DW       17850,8925,3570,1785,892,357,178,89,36,9
      F20DF906
      7C036501
      B2005900
      24000900
440F            ;                    SLOW RAMP 1
440F            SPRMP1
440F                        MOVE     R1.CBLK,R.CBLK,SZ.RCBLK
441F  3A93F8                LDA      R.IMPL ; SEE IF IMPLEMENTED
4422  FEFF                  CPI      0FFH
4424  C22B44                JNZ      SPRMP1.1 ; YES, GO EXECUTE
4427  2A62F8                LHLD     PSTACK+4 ; GET NEXT ROUTINE
442A  E9                    PCHL     ; GO EXECUTE IT
442B            SPRMP1.1
442B  2A62F8                LHLD     PSTACK+4 ; GET NEXT ROUTINE
442E  223DF8                SHLD     PNEXT
4431  2E92                  MVI      L,RCODE ; TELL WHICH STEP
4433  2620                  MVI      H,CODE1
4435  222FF8                SHLD     PACTBUF
4438  3A02E0                LDA      C1ST
443B  F601                  ORI      LD.RMP1
443D  3202E0                STA      C1ST
4440  3A01E0                LDA      B1ST
4443  E6BF                  ANI      "LD.RMP2
4445  3201E0                STA      B1ST
4448  C38744                JMP      PRB101
444B            ;                    SLOW RAMP 2
444B            SPRMP2
444B                        MOVE     R2.CBLK,R.CBLK,SZ.RCBLK
445B  3A93F8                LDA      R.IMPL ; SEE IF IMPLEMENTED
```

```
445E  FEFF                    CPI       0FFH
4460  C26744                  JNZ       SPRMP2.1 ; YES, GO EXECUTE
4463  2A66F8                  LHLD      PSTACK+8 ; GET NEXT ROUTINE
4466  E9                      PCHL      ; GO EXECUTE IT
4467            SPRMP2.1
4467  2A66F8                  LHLD      PSTACK+8 ; GET NEXT ROUTINE
446A  223DF8                  SHLD      PNEXT
446D  2E92                    MVI       L,RCODE ; TELL WHICH STEP
446F  2630                    MVI       H,CODE2
4471  222FF8                  SHLD      PACTBUF
4474  3A01E0                  LDA       B1ST
4477  F640                    ORI       LD.RMP2
4479  3201E0                  STA       B1ST
447C  3A02E0                  LDA       C1ST
447F  E6FE                    ANI       "LD.RMP1
4481  3202E0                  STA       C1ST
4484  C38744                  JMP       PRB101
4487            ;                       COMMON CODE
4487            PRB101
4487  3A01E0                  LDA       B1ST
448A  E6D7                    ANI       "(LD.FTMP1+LD.FTMP2)
448C  3201E0                  STA       B1ST
448F  3A02E0                  LDA       C1ST
4492  E6EF                    ANI       "LD.INTH
4494  3202E0                  STA       C1ST
4497                          KILLPROB  ; KILL ANY RUNNING PROBE HARDWARE
44A2                          FILL      PACTBUF+5,CODE0,3
44AF  210000                  LXI       H,0 ; CLEAR RUN TIME
44B2  223FF8                  SHLD      PRTIME
44B5            ;             INCREMENT THE TEMPERATURE 1 DEGREE/INTERVAL
44B5  2A81F8                  LHLD      R.RATE ; GET TIMER INTERVAL
44B8  228EF0                  SHLD      CBLK14 ; LOAD THE CONTROL BLOCK MANUALLY
44BB  2290F0                  SHLD      CBLK14+2
44BE  3A6AF8                  LDA       R.DIR ; GET DIRECTION
44C1  FEFF                    CPI       0FFH ; SEE IF UP OR DOWN
44C3  CACC44                  JZ        PRB102 ; DOWN ...
44C6  21E044                  LXI       H,PRB110
44C9  C3CF44                  JMP       PRB103
44CC            PRB102
44CC  21D944                  LXI       H,PRB109
44CF            PRB103
44CF  2292F0                  SHLD      CBLK14+4
44D2  218EF0                  LXI       H,CBLK14
44D5  CD6230                  CALL      QUEUE
44D8  C9                      RET
44D9            ;                       DECREMENT THE TEMPERATURE
44D9            PRB109
44D9  2A41F8                  LHLD      PTEMP
44DC  2B                      DCX       H
44DD  C3E444                  JMP       PRB110.5
44E0            ;                       INCREMENT THE TEMPERATURE
44E0            PRB110
44E0  2A41F8                  LHLD      PTEMP ; GET MAINTENANCE TEMP
44E3  23                      INX       H ; BUMP UP
44E4            PRB110.5
44E4  2241F8                  SHLD      PTEMP ; SAVE NEW TEMP
44E7                          SETEMP    H
44F8  CD1532                  CALL      BIN2PK
44FB  0131F8                  LXI       B,PACTBUF+2
44FE  CD3031                  CALL      PRVRT3
4501  2A6BF8                  LHLD      R.DUR ; GET DURATION
4504  7D                      MOV       A,L ; SEE IF '0'
4505  B4                      ORA       H
4506  C21945                  JNZ       PRB111 ; NOT YET
4509                          DELETE    CBLK14 ; ELSE, KILL TIMER
450F                          DELETE    CBLK15
4515  2A3DF8                  LHLD      PNEXT ; GET NEXT ROUTINE
4518  E9                      PCHL      ; GO DO IT
4519            PRB111
4519  2B                      DCX       H ; DECREMENT IT
451A  226BF8                  SHLD      R.DUR
451D  C9                      RET
451E            ;**********************************
451E            ;                       FAST RAMP1
451E            FPRMP1
451E                          MOVE      R1.CBLK,R.CBLK,SZ.RCBLK
452E  3A93F8                  LDA       R.IMPL ; SEE IF IMPLEMENTED
4531  FEFF                    CPI       0FFH
4533  C23A45                  JNZ       FPRMP1.5 ; YES, GO EXECUTE
4536  2A62F8                  LHLD      PSTACK+4
4539  E9                      PCHL
453A            FPRMP1.5
453A  2E92                    MVI       L,RCODE ; TELL WHICH STEP
453C  2620                    MVI       H,CODE1
453E  222FF8                  SHLD      PACTBUF
4541  2A62F8                  LHLD      PSTACK+4 ; GET NEXT ROUTINE
4544  2298F8                  SHLD      RNEXT
4547  3A02E0                  LDA       C1ST
454A  F601                    ORI       LD.RMP1
454C  3202E0                  STA       C1ST
454F  3A01E0                  LDA       B1ST
4552  E6BF                    ANI       "LD.RMP2
4554  3201E0                  STA       B1ST
4557  C39645                  JMP       FPRB01
455A            ;                       FAST RAMP 2
```

```
455A                 FPRMP2
455A                           MOVE      R2.CBLK,R.CBLK,SZ.RCBLK
456A    3A93F8                 LDA       R.IMPL ; SEE IF IMPLEMENTED
456D    FEFF                   CPI       0FFH
456F    C27645                 JNZ       FPRMP2.5 ; YES, GO EXECUTE
4572    2A66F8                 LHLD      PSTACK+8
4575    E9                     PCHL
4576                 FPRMP2.5
4576    2E92                   MVI       L,RCODE ; TELL WHICH STEP
4578    2630                   MVI       H,CODE2
457A    222FF8                 SHLD      PACTBUF
457D    2A66F8                 LHLD      PSTACK+8 ; GET NEXT ROUTINE
4580    2298F8                 SHLD      RNEXT
4583    3A02E0                 LDA       C1ST
4586    E6FE                   ANI       "LD.RMP1
4588    3202E0                 STA       C1ST
458B    3A01E0                 LDA       B1ST
458E    F640                   ORI       LD.RMP2
4590    3201E0                 STA       B1ST
4593    C39645                 JMP       FPRB01
4596                 ;                   COMMON CODE
4596                 FPRB01
4596    3A01E0                 LDA       B1ST
4599    E6D7                   ANI       "(LD.FTMP1+LD.FTMP2)
459B    3201E0                 STA       B1ST
459E    3A02E0                 LDA       C1ST
45A1    E6EF                   ANI       "LD.INTH
45A3    3202E0                 STA       C1ST
45A6                           KILLPROB  ; KILL ANY RUNNING PROBE HARDWARE
45B1                           FILL      PACTBUF+5,CODE0,3
45BE    210000                 LXI       H,0 ; CLEAR RUN TIME
45C1    223FF8                 SHLD      PRTIME
45C4                           SETEMP    R.STRT
45D9                           SETRATE   R.RATE
45E7                           SETFNL    R.DEST
45FC    3A6DF8                 LDA       R.CNTRL1
45FF    329CF8                 STA       P.IMAGE
4602                           GORAMP
4607    C9                     RET
4608    ;**********************************************************************
4608    ;                      VERY FAST RAMP ROUTINE
4608                 VFPRMP1
4608                           MOVE      R1.CBLK,R.CBLK,SZ.RCBLK
4618    2A62F8                 LHLD      PSTACK+4
461B    3A93F8                 LDA       R.IMPL ; SEE IF IMPLEMENTED
461E    FEFF                   CPI       0FFH
4620    CA3646                 JZ        VFPRMP1.5 ; NO ...
4623    3A02E0                 LDA       C1ST
4626    F601                   ORI       LD.RMP1
4628    3202E0                 STA       C1ST
462B    3A01E0                 LDA       B1ST
462E    E6BF                   ANI       "LD.RMP2
4630    3201E0                 STA       B1ST
4633    C36646                 JMP       VFPRMP2.8
4636                 VFPRMP1.5
4636    E9                     PCHL
4637                 ;
4637                 VFPRMP2
4637                           MOVE      R2.CBLK,R.CBLK,SZ.RCBLK
4647    2A66F8                 LHLD      PSTACK+8
464A    3A93F8                 LDA       R.IMPL ; SEE IF IMPLEMENTED
464D    FEFF                   CPI       0FFH
464F    CA6546                 JZ        VFPRMP2.5 ; NO ...
4652    3A02E0                 LDA       C1ST
4655    E6FE                   ANI       "LD.RMP1
4657    3202E0                 STA       C1ST
465A    3A01E0                 LDA       B1ST
465D    F640                   ORI       LD.RMP2
465F    3201E0                 STA       B1ST
4662    C36646                 JMP       VFPRMP2.8
4665                 VFPRMP2.5
4665    E9                     PCHL
4666                 ;
4666                 VFPRMP2.8
4666    223DF8                 SHLD      PNEXT
4669                           KILLPROB  ; KILL ANY RUNNING PROBE HARDWARE
4674    21A346                 LXI       H,VFR01 ; NEXT RAMP SEGMENT
4677    229AF8                 SHLD      BNEXT
467A                           SETBST    R.DUR
4688    3E88                   MVI       A,B.TRGR+B.INTE
468A    329CF8                 STA       P.IMAGE
468D                           GOBST
4692    3A02E0                 LDA       C1ST
4695    E6EF                   ANI       "LD.INTH
4697    3202E0                 STA       C1ST
469A    3A01E0                 LDA       B1ST
469D    E6D7                   ANI       "(LD.FTMP1+LD.FTMP2)
469F    3201E0                 STA       B1ST
46A2    C9                     RET
46A3                 VFR01
46A3    21F346                 LXI       H,VFR02 ; NEXT RAMP SEGMENT
46A6    2298F8                 SHLD      RNEXT
46A9                 ;         START TO APPLY THE DIP CORRECTION
46A9                           SETEMP    R.STRT
46BE                           SETFNL    R.DEST1
```

```
46D3                            SETRATE   R.RATE
46E1  3A6DF8                    LDA       R.CNTRL1
46E4  329CF8                    STA       P.IMAGE
46E7                            GORAMP
46EC  2A3DF8                    LHLD      PNEXT ; GET NEXT ROUTINE
46EF  CD6130                    CALL      INDRCT ; GO START NEXT ROUTINE
46F2  C9                        RET
46F3                 VFR02
46F3  213D47                    LXI       H,VFR03 ; NEXT SEGMENT
46F6  2298F8                    SHLD      RNEXT
46F9                            SETEMP    R.DEST1
470E                            SETFNL    R.DEST2
4723                            SETRATE   R.RATE1
4731  3A6DF8                    LDA       R.CNTRL1
4734  329CF8                    STA       P.IMAGE
4737                            GORAMP
473C  C9                        RET
473D                 VFR03
473D  218747                    LXI       H,VFR04 ; NEXT SEGMENT
4740  2298F8                    SHLD      RNEXT
4743                            SETEMP    R.DEST2
4758                            SETFNL    R.DEST3
476D                            SETRATE   R.RATE2
477B  3A6DF8                    LDA       R.CNTRL1
477E  329CF8                    STA       P.IMAGE
4781                            GORAMP
4786  C9                        RET
4787                 VFR04
4787  21D147                    LXI       H,VFR05 ; NEXT SEGMENT
478A  2298F8                    SHLD      RNEXT
478D                            SETEMP    R.DEST3
47A2                            SETFNL    R.DEST4
47B7                            SETRATE   R.RATE3
47C5  3A6DF8                    LDA       R.CNTRL1
47C8  329CF8                    STA       P.IMAGE
47CB                            GORAMP
47D0  C9                        RET
47D1                 VFR05
47D1  211B48                    LXI       H,VFR06 ; NEXT SEGMENT
47D4  2298F8                    SHLD      RNEXT
47D7                            SETEMP    R.DEST4
47EC                            SETFNL    R.DEST5
4801                            SETRATE   R.RATE4
480F  3A6DF8                    LDA       R.CNTRL1
4812  329CF8                    STA       P.IMAGE
4815                            GORAMP
481A  C9                        RET
481B                 VFR06
481B  216548                    LXI       H,VFR07 ; NEXT SEGMENT
481E  2298F8                    SHLD      RNEXT
4821                            SETEMP    R.DEST5
4836                            SETFNL    R.DEST6
484B                            SETRATE   R.RATE5
4859  3A6DF8                    LDA       R.CNTRL1
485C  329CF8                    STA       P.IMAGE
485F                            GORAMP
4864  C9                        RET
4865                 VFR07
4865  21AF48                    LXI       H,VFR08 ; NEXT SEGMENT
4868  2298F8                    SHLD      RNEXT
486B                            SETEMP    R.DEST6
4880                            SETFNL    R.DEST7
4895                            SETRATE   R.RATE6
48A3  3A6DF8                    LDA       R.CNTRL1
48A6  329CF8                    STA       P.IMAGE
48A9                            GORAMP
48AE  C9                        RET
48AF                 VFR08
48AF  210133                    LXI       H,DUMMY ; SO THE INTERUPT ROUTINE DOESN'T BLOW
48B2  2298F8                    SHLD      RNEXT
48B5                            SETEMP    R.DEST7
48CA                            SETFNL    R.DEST
48DF                            SETRATE   R.RATE7
48ED  3A6DF8                    LDA       R.CNTRL1
48F0  329CF8                    STA       P.IMAGE
48F3                            GORAMP
48F8  C9                        RET
48F9            ;***********************************************************************
48F9                 PNCTIM
48F9  3A40F8                    LDA       PRTIME+1 ; GET LO BYTE
48FC  3C                        INR       A ; BUMP UP
48FD  27                        DAA
48FE  3240F8                    STA       PRTIME+1
4901  3A3FF8                    LDA       PRTIME
4904  CE00                      ACI       0 ; ADD CARRY
4906  27                        DAA
4907  323FF8                    STA       PRTIME
490A  2A3FF8                    LHLD      PRTIME ; GET PACKED DECIMAL NUMBER
490D  0134F8                    LXI       B,PACTBUF+5 ; POINT TO DISPLAY AREA
4910  CD3031                    CALL      PRVRT3 ; TO DISPLAYABLE
4913  C9                        RET
4914            ;***********************************************************************
4914            ;
4914            ;         DECREMENT THE ELAPSED TIME COUNTER AND LOAD ADDRESS OF NEXT
4914            ;    ROUTINE IF 0
```

```
4914                        ;         ENTERED FROM TIMER QUE
4914             PRBTIM     ENTRY
4914   2A3BF8               LHLD      PELAPSE ; GET TIME TO GO
4917   7D                   MOV       A,L ; SEE IF '0'
4918   B4                   ORA       H
4919   C22649               JNZ       PRB121 ; NOT YET
491C                        DELETE    CBLK14
4922   2A3DF8               LHLD      PNEXT ; GET NEXT STEP
4925   E9                   PCHL      ; GO DO IT
4926             PRB121
4926   2B                   DCX       H ; DECREMENT IT
4927   223BF8               SHLD      PELAPSE ; SAVE IT
492A   CDF948               CALL      PNCTIM
492D   C9                   RET
492E             ;************************************************************
492E             ;
492E             ;         ROUTINE TO CLEANLY EXIT FROM EXECUTING A METHOD
492E             ;         ENTERED FROM TIMER QUE
492E             PRBXIT     ENTRY
492E                        TIMER     100,0,PRBENBL,CBLK18
4946                        KILLPROB  ; KILL ANY ACTIVE PROBE HARDWARE
4951   CD9049               CALL      PRBHOME ; INITIALIZE TEMP
4954                        DELETE    CBLK14 ; KILL TIMERS
495A                        DELETE    CBLK15
4960   3A01E0               LDA       B1ST
4963   E697                 ANI       "(LD.FTMP1+LD.FTMP2+LD.RMP2)
4965   3201E0               STA       B1ST
4968   3A02E0               LDA       C1ST
496B   E6EE                 ANI       "(LD.RMP1+LD.INTH)
496D   3202E0               STA       C1ST
4970                        FILL      PACTBUF+5,CODE0,3
497D   3E82                 MVI       A,PCODE ; INDICATE WHICH BUFFER THIS IS
497F   322FF8               STA       PACTBUF
4982   3E00                 MVI       A,BLANK
4984   3230F8               STA       PACTBUF+1
4987   C9                   RET
4988             ;                    ENABLE PROBE USE
4988             PRBENBL
4988   AF                   XRA       A ; CLEAR RUNNING FLAGS
4989   3243F8               STA       PRUNFLG
498C   3244F8               STA       PHLDFLG
498F   C9                   RET
4990             ;************************************************************
4990             ;                    INITIALIZE THE PROBE TEMP
4990             ;
4990             PRBHOME    ENTRY
4990   210000               LXI       H,0 ; INITIALIZE PROBE TEMP
4993   2241F8               SHLD      PTEMP
4996                        SETEMP    H
49A7   CD1532               CALL      BIN2PK
49AA   0131F8               LXI       B,PACTBUF+2
49AD   CD3031               CALL      PRVRT3
49B0   C9                   RET
49B1             ;************************************************************
49B1             ;
49B1             ;         DO ALL RAMP CALCULATIONS PRIOR TO STARTING THE RUN
49B1             ;
49B1             ;                    'HL' = NEXT LEVEL
49B1             ;                    'DE' = LAST LEVEL
49B1             ;
49B1             ;                    DO SLOW RAMP1
49B1             SRAMP
49B1   23                   INX       H
49B2   13                   INX       D
49B3                        SAVE      H,D
49B5   07                   RLC       ; CONVERT TO OFFSET
49B6   010000               LXI       B,0
49B9   4F                   MOV       C,A
49BA   21D943               LXI       H,PINTVL ; POINT TO INTERVAL TABLE
49BD   09                   DAD       B ; POINT TO INTERVAL
49BE   7E                   MOV       A,M ; GET INTERVAL
49BF   3281F8               STA       R.RATE
49C2   23                   INX       H
49C3   7E                   MOV       A,M
49C4   3282F8               STA       R.RATE+1
49C7                        RESTOR    H,D
49C9   226FF8               SHLD      R.STRT
49CC                        DR2CM     H
49D3   19                   DAD       D ; 'HL' = HOLD1 + (-INIT)
49D4   D2DE49               JNC       SRAMP1.1 ; IF HOLD > INIT
49D7   AF                   XRA       A ; SET RAMP1 DIRECTION TO UP
49D8   326AF8               STA       R.DIR
49DB   C3EA49               JMP       SRAMP1.2
49DE             SRAMP1.1
49DE   3EFF                 MVI       A,OFFH ; SET RAMP1 DIRECTION TO DOWN
49E0   326AF8               STA       R.DIR
49E3                        DR2CM     H
49EA             SRAMP1.2
49EA   226BF8               SHLD      R.DUR ; DURATION IN DEGREES
49ED   AF                   XRA       A
49EE   3293F8               STA       R.IMPL
49F1   7D                   MOV       A,L
49F2   B4                   ORA       H
49F3   C0                   RNZ
49F4   3EFF                 MVI       A,OFFH
```

```
49F6  3293F8              STA     R.IMPL
49F9  C9                  RET
49FA              ;               DO FAST RAMP
49FA              FRAMP
49FA  23                  INX     H
49FB  13                  INX     D
49FC                      SAVE    H,D ; SAVE FOR LATER
49FE  07                  RLC     ; CONVERT TO OFFSET
49FF  010000              LXI     B,0
4A02  4F                  MOV     C,A
4A03  21D943              LXI     H,PINTVL ; POINT TO INTERVAL TABLE
4A06  09                  DAD     B ; POINT TO INTERVAL
4A07  7E                  MOV     A,M ; GET INTERVAL
4A08  3281F8              STA     R.RATE
4A0B  23                  INX     H
4A0C  7E                  MOV     A,M
4A0D  3282F8              STA     R.RATE+1
4A10                      RESTOR  H
4A11  226FF8              SHLD    R.STRT
4A14                      RESTOR  D
4A15  EB                  XCHG
4A16  227FF8              SHLD    R.DEST
4A19  EB                  XCHG
4A1A                      DR2CM   H
4A21  19                  DAD     D ; 'HL' = HOLD1 + (-INIT)
4A22  DA2B4A              JC      FRAMP1.4 ; IF COUNT UP
4A25              FRAMP1.3
4A25  3E34                MVI     A,P.INTE+P.TRGR+P.UPDN ; ELSE COUNT DOWN
4A27  326DF8              STA     R.CNTRL1
4A2A  C9                  RET
4A2B              FRAMP1.4
4A2B  AF                  XRA     A
4A2C  3293F8              STA     R.IMPL
4A2F  7D                  MOV     A,L ; SEE IF DELTA DEGREES IS '0'
4A30  B4                  ORA     H
4A31  C23C4A              JNZ     FRAMP1.5 ; '0' IS A SPECIAL CASE
4A34  3EFF                MVI     A,0FFH
4A36  3293F8              STA     R.IMPL
4A39  C3254A              JMP     FRAMP1.3
4A3C              FRAMP1.5
4A3C  3E14                MVI     A,P.INTE+P.TRGR
4A3E  326DF8              STA     R.CNTRL1
4A41  C9                  RET
4A42              ;               VERY FAST RAMP ROUTINE
4A42              VFRAMP
4A42  23                  INX     H
4A43  13                  INX     D
4A44                      SAVE    H,D
4A46  7A                  MOV     A,D ; SEE IF INITIAL TEMP>255 DEGREES
4A47  FE00                CPI     0
4A49  C2554A              JNZ     VFRAMP2 ; YES, ...
4A4C  3AE5C8              LDA     TSTSLP1 ; CHANGE IN FACTOR/100 DEGREES IF INIT TEMP<255 DEGREES
4A4F  4F                  MOV     C,A
4A50  0600                MVI     B,0
4A52  C35B4A              JMP     VFRAMP3
4A55              VFRAMP2
4A55  3AE7C8              LDA     TSTSLP2 ; CHANGE IN FACTOR/100 DEGREES IF INIT TEMP>255 DEGREES
4A58  4F                  MOV     C,A
4A59  0600                MVI     B,0
4A5B              VFRAMP3
4A5B  CDBC32              CALL    I4MULT
4A5E  016400              LXI     B,100
4A61  CDDF32              CALL    I4DIVD ; /100 DEGREES !!
4A64  2AEBC8              LHLD    TSTFCTR3 ; GET BOOST FACTOR
4A67  19                  DAD     D
4A68  22E9C8              SHLD    TSTFCTR2 ; SAVE IT
4A6B  2AE3C8              LHLD    TSTFCTR1
4A6E  19                  DAD     D ; 'HL' CONTAINS NEW FACTOR
4A6F  22D1C8              SHLD    TSTFCTR
4A72                      RESTOR  D,H
4A74              ;
4A74  3E34                MVI     A,P.TRGR+P.INTE+P.UPDN
4A76  326DF8              STA     R.CNTRL1
4A79  227FF8              SHLD    R.DEST ; FINAL DESTINATION TEMP
4A7C                      DR2CM   D
4A83  19                  DAD     D ; GET DELTA TEMP
4A84  AF                  XRA     A
4A85  3293F8              STA     R.IMPL
4A88  7D                  MOV     A,L
4A89  B4                  ORA     H
4A8A  C2924A              JNZ     VFRAMP1
4A8D  3EFF                MVI     A,0FFH
4A8F  3293F8              STA     R.IMPL
4A92              VFRAMP1
4A92                      SAVE    H ; SAVE DELTA TEMP FOR BOOST
4A93  EB                  XCHG    ; PUT DELTA INTO 'DE'
4A94  010001              LXI     B,0100H ; TO ALLOW FACTORING R.STRT
4A97  CDBC32              CALL    I4MULT
4A9A  3AD1C8              LDA     TSTFCTR ; GET FACTOR
4A9D  4F                  MOV     C,A
4A9E  3AD2C8              LDA     TSTFCTR+1
4AA1  47                  MOV     B,A
4AA2  CDDF32              CALL    I4DIVD ; END FACTORING
4AA5  2A7FF8              LHLD    R.DEST ; GET FINAL DEST TEMP
4AA8  19                  DAD     D ; GET R.STRT
4AA9  226FF8              SHLD    R.STRT
```

```
4AAC                    DRRC     D
4AB3  2A7FF8            LHLD     R.DEST ; GET FINAL DEST TEMP
4AB6  19                DAD      D ; GET INTERMEDIATE STEP DEST TEMP
4AB7  2271F8            SHLD     R.DEST1 ; SAVE IT
4ABA                    DRRC     D
4AC1  2A7FF8            LHLD     R.DEST ; GET FINAL DEST TEMP
4AC4  19                DAD      D ; GET INTERMEDIATE STEP DEST TEMP
4AC5  2273F8            SHLD     R.DEST2 ; SAVE IT
4AC8                    DRRC     D
4ACF  2A7FF8            LHLD     R.DEST ; GET FINAL DEST TEMP
4AD2  19                DAD      D ; GET INTERMEDIATE STEP DEST TEMP
4AD3  2275F8            SHLD     R.DEST3 ; SAVE IT
4AD6                    DRRC     D
4ADD  2A7FF8            LHLD     R.DEST ; GET FINAL DEST TEMP
4AE0  19                DAD      D ; GET INTERMEDIATE STEP DEST TEMP
4AE1  2277F8            SHLD     R.DEST4 ; SAVE IT
4AE4                    DRRC     D
4AEB  2A7FF8            LHLD     R.DEST ; GET FINAL DEST TEMP
4AEE  19                DAD      D ; GET INTERMEDIATE STEP DEST TEMP
4AEF  2279F8            SHLD     R.DEST5 ; SAVE IT
4AF2                    DRRC     D
4AF9  2A7FF8            LHLD     R.DEST ; GET FINAL DEST TEMP
4AFC  19                DAD      D ; GET INTERMEDIATE STEP DEST TEMP
4AFD  227BF8            SHLD     R.DEST6 ; SAVE IT
4B00                    DRRC     D
4B07  2A7FF8            LHLD     R.DEST ; GET FINAL DEST TEMP
4B0A  19                DAD      D ; GET INTERMEDIATE STEP DEST TEMP
4B0B  227DF8            SHLD     R.DEST7 ; SAVE IT
4B0E              ;              GET THE BOOST TIME
4B0E                    RESTOR   D
4B0F  01F906            LXI      B,1785 ; # OF CYCLES/MSEC
4B12  CDBC32            CALL     I4MULT ; 'HLDE' = #CYCLE DEGREES/MSEC
4B15  3AE9C8            LDA      TSTFCTR2 ; 'BC' = #DEGREES/MSEC OF BOOST
4B18  4F                MOV      C,A
4B19  3AEAC8            LDA      TSTFCTR2+1
4B1C  47                MOV      B,A
4B1D  CDDF32            CALL     I4DIVD ; 'DE' = # CYCLES
4B20  EB                XCHG
4B21  226BF8            SHLD     R.DUR ; BOOST DURATION IN CYCLES
4B24  C9                RET
4B25         ;***********************************************************
4B25                    END
4B25         ;***********************************************************
4B25         ;
4B25                    USE      EPROM5
5000         ;
5000         ;          EXECUTE A FIXED TEMPERATURE INTERFACE STEP (INIT, HOLD1, FINAL)
5000         ;          ENTERED FROM TIMER QUE
5000                EIINT
5000  C30F50            JMP      IFCINT
5003                EIXIT
5003  C34052            JMP      IFCXIT
5006                EITIM
5006  C32652            JMP      IFCTIM
5009                INITMP
5009  C36E52            JMP      IFCHOME
500C                CALCULATI
500C  C37552            JMP      IFCCALC
500F         ;
500F         ;          INITIAL TIME/TEMP ROUTINE
500F                IFCINT   ENTRY
500F  CD0C50            CALL     CALCULATI ; GET RAMP DURATIONS
5012  2E32              MVI      L,ICODE ; TELL WHICH STEP
5014  2662              MVI      H,NCODE
5016  2223F8            SHLD     IACTBUF
5019  213151            LXI      H,IFCRMP1 ; NEXT ROUTINE TO EXECUTE
501C  2216F8            SHLD     INEXT
501F  2101C8            LXI      H,IMETHD0+OF.INT ; POINT TO INITIAL TIME/TEMP
5022  C34B50            JMP      IFCO1
5025         ;          HOLD 1 TIME/TEMP ROUTINE
5025                IFCHD1
5025  2E22              MVI      L,HCODE ; TELL WHICH STEP
5027  2620              MVI      H,CODE1
5029  2223F8            SHLD     IACTBUF
502C  215151            LXI      H,IFCRMP2 ; NEXT ROUTINE TO EXECUTE
502F  2216F8            SHLD     INEXT
5032  2107C8            LXI      H,IMETHD0+OF.HD1 ; POINT TO HOLD1 TIME/TEMP
5035  C34B50            JMP      IFCO1
5038         ;          FINAL TIME/TEMP ROUTINE
5038                IFCFNL
5038  2E02              MVI      L,FCODE ; TELL WHICH STEP
503A  2632              MVI      H,ICODE
503C  2223F8            SHLD     IACTBUF
503F  214052            LXI      H,IFCXIT ; NEXT ROUTINE TO EXECUTE
5042  2216F8            SHLD     INEXT
5045  210DC8            LXI      H,IMETHD0+OF.FNL ; POINT TO FINAL TIME/TEMP
5048  C34B50            JMP      IFCO1
504B         ;
504B                IFCO1
504B                    SAVE     H
504C                    FILL     IACTBUF+5,CODE0,3
5059  210000            LXI      H,0 ; ZERO RUN TIME
505C  222BF8            SHLD     IRTIME
505F                    RESTOR   H
```

```
5060  3A00E0              LDA     A1ST ; GET LED STATUS
5063  E6F0                ANI     0F0H ; CLEAR TIME BASE LEDS
5065  B6                  ORA     M ; SET TIME BASE LED
5066  3200E0              STA     A1ST ; SET LED STATUS
5069  23                  INX     H ; POINT TO TEMPERATURE
506A  5E                  MOV     E,M ; GET THE LO BYTE
506B  23                  INX     H
506C  56                  MOV     D,M ; GET HI BYTE
506D  EB                  XCHG    ; PUT TEMP INTO 'HL'
506E  13                  INX     D ; POINT TO TIME
506F  2218F8              SHLD    ITEMP ; SAVE TEMP
5072  EB                  XCHG    ; 'HL' POINTS TO TIME
5073  5E                  MOV     E,M ; GET LO BYTE
5074  23                  INX     H
5075  56                  MOV     D,M ; GET HI BYTE
5076  EB                  XCHG    ; PUT TIME INTO 'HL'
5077  3A00E0              LDA     A1ST ; SEE IF MILLISECONDS
507A  E601                ANI     LD.MSEC
507C  CA8850              JZ      IFC01.2 ; NO ...
507F  CD1532              CALL    BIN2PK ; TO PACKED DECIMAL
5082  65                  MOV     H,L ; DIVIDE BY 100
5083  2E00                MVI     L,0
5085  CD8831              CALL    PK2BIN ; CONVERT TO BINARY
5088          IFC01.2
5088  7D                  MOV     A,L ; SEE IF '0'
5089  B4                  ORA     H
508A  CA0D51              JZ      IFC04 ; YES ...
508D  2B                  DCX     H
508E  2214F8              SHLD    IELAPSE ; SAVE TIME TO RUN
5091  3A00E0              LDA     A1ST ; GET TIME BASE
5094  E602                ANI     LD.SEC ; SECONDS ?
5096  C2C250              JNZ     IFC01.5 ; YES ...
5099  3A00E0              LDA     A1ST
509C  E604                ANI     LD.MIN ; MINUTES ?
509E  C2DB50              JNZ     IFC02 ; YES ...
50A1  3A00E0              LDA     A1ST
50A4  E608                ANI     LD.HOUR ; HOURS ?
50A6  C2F450              JNZ     IFC03 ; YES ...
50A9          ;                   ASSUME MILLISECONDS
50A9                      TIMER   1,1,IFCTIM,CBLK09
50C1  C9                  RET
50C2          ;           SECONDS
50C2          IFC01.5
50C2                      TIMER   10,10,IFCTIM,CBLK09
50DA  C9                  RET
50DB          ;           MINUTES
50DB          IFC02
50DB                      TIMER   600,600,IFCTIM,CBLK09
50F3  C9                  RET
50F4          ;           HOURS
50F4          IFC03
50F4                      TIMER   36000,36000,IFCTIM,CBLK09
510C  C9                  RET
510D          ;
510D          IFC04
510D  2A16F8              LHLD    INEXT
5110  E9                  PCHL
5111          ;*****************************************
5111          ;
5111          ;
5111          ;           EXECUTE A RAMPED INTERFACE STEP (RAMP1, RAMP2)
5111          ;           ENTERED FROM TIMER QUE
5111          ;
5111  00005802  INTVL    DW      0,600,300,150,100,75,60,48,40,30,24,20,15,12,10,10
      2C019600
      64004B00
      3C003000
      28001E00
      18001400
      0F000C00
      0A000A00
5131          ;
5131          IFCRMP1
5131  2E92                MVI     L,RCODE ; TELL WHICH STEP
5133  2620                MVI     H,CODE1
5135  2223F8              SHLD    IACTBUF
5138  212550              LXI     H,IFCHD1
513B  2216F8              SHLD    INEXT
513E                      MOVE    IR1.CBLK,IR.CBLK,SZ.RCBLK
514E  C37151              JMP     IFC101
5151          ;
5151          IFCRMP2
5151  2E92                MVI     L,RCODE ; TELL WHICH STEP
5153  2630                MVI     H,CODE2
5155  2223F8              SHLD    IACTBUF
5158  213850              LXI     H,IFCFNL
515B  2216F8              SHLD    INEXT
515E                      MOVE    IR2.CBLK,IR.CBLK,SZ.RCBLK
516E  C37151              JMP     IFC101
5171          ;
5171          IFC101
5171                      FILL    IACTBUF+5,CODE0,3
517E  210000              LXI     H,0 ; CLEAR RUN TIME
5181  222BF8              SHLD    IRTIME
5184  3A72E8              LDA     IR.RATE ; GET RATE
```

```
5187  FE00                CPI      0 ; SEE IF IMPLEMENTED STEP
5189  CAD951              JZ       IFC104 ; NO ...
518C  07                  RLC      ; CONVERT TO OFFSET
518D  010000              LXI      B,0
5190  4F                  MOV      C,A
5191  211151              LXI      H,INTVL ; POINT TO INTERVAL TABLE
5194  09                  DAD      B ; POINT TO INTERVAL
5195  4E                  MOV      C,M ; GET INTERVAL
5196  23                  INX      H
5197  46                  MOV      B,M
5198                      SAVE     B ; PUT INTO 'HL' AS WELL
5199                      RESTOR   H
519A                 ;             INCREMENT THE TEMPERATURE 1 DEGREE/INTERVAL
519A  2270F0              SHLD     CBLK09 ; LOAD THE CONTROL BLOCK MANUALLY
519D  2272F0              SHLD     CBLK09+2
51A0  2A6DE8              LHLD     IR.DUR ; GET DURATION
51A3  2214F8              SHLD     IELAPSE
51A6  3A6CE8              LDA      IR.DIR ; GET DIRECTION
51A9  FEFF                CPI      0FFH
51AB  CAB451              JZ       IFC102 ; DOWN ...
51AE  21E751              LXI      H,IFC110
51B1  C3B751              JMP      IFC103
51B4             IFC102
51B4  21DD51              LXI      H,IFC109
51B7             IFC103
51B7  2274F0              SHLD     CBLK09+4
51BA  2170F0              LXI      H,CBLK09
51BD  CD6230              CALL     QUEUE
51C0                      TIMER    10,10,INCTIM,CBLK13
51D8  C9                  RET
51D9                 ;             UNIMPLEMENTED STEP
51D9             IFC104
51D9  2A16F8              LHLD     INEXT ; GET NEXT STEP
51DC  E9                  PCHL     ; GO DO IT
51DD                 ;             DECREMENT THE TEMPERATURE
51DD             IFC109
51DD  2A18F8              LHLD     ITEMP
51E0  2B                  DCX      H
51E1  2219F8              SHLD     ITEMP
51E4  C3EE51              JMP      IFC110.5
51E7                 ;             INCREMENT THE TEMPERATURE
51E7             IFC110
51E7  2A18F8              LHLD     ITEMP ; GET MAINTENANCE TEMP
51EA  23                  INX      H ; BUMP UP
51EB  2218F8              SHLD     ITEMP ; SAVE NEW TEMP
51EE                 ;
51EE             IFC110.5
51EE  2A14F8              LHLD     IELAPSE ; GET DURATION
51F1  7D                  MOV      A,L ; SEE IF '0'
51F2  B4                  ORA      H
51F3  C20652              JNZ      IFC111 ; NOT YET
51F6                      DELETE   CBLK13 ; KILL TIMER
51FC                      DELETE   CBLK09
5202  2A16F8              LHLD     INEXT ; GET NEXT ROUTINE
5205  E9                  PCHL     ; GO DO IT
5206             IFC111
5206  2B                  DCX      H ; DECREMENT IT
5207  2214F8              SHLD     IELAPSE
520A  C9                  RET
520B             ;***********************************
520B             INCTIM
520B  3A2CF8              LDA      IRTIME+1 ; GET LO BYTE
520E  3C                  INR      A ; BUMP UP
520F  27                  DAA
5210  322CF8              STA      IRTIME+1
5213  3A2BF8              LDA      IRTIME
5216  CE00                ACI      0 ; ADD CARRY
5218  27                  DAA
5219  322BF8              STA      IRTIME
521C  2A2BF8              LHLD     IRTIME ; GET PACKED DECIMAL NUMBER
521F  0128F8              LXI      B,IACTBUF+5 ; POINT TO DISPLAY AREA
5222  CD3031              CALL     PRVRT3 ; TO DISPLAYABLE
5225  C9                  RET
5226             ;***********************************
5226             ;
5226             ;
5226             ;             DECREMENT THE ELAPSED TIME COUNTER AND LOAD ADDRESS OF NEXT
5226             ;     ROUTINE IF 0
5226             ;     ENTERED FROM TIMER QUE
5226             IFCTIM   ENTRY
5226  CD0B52              CALL     INCTIM ; INCREMENT DISPLAY TIME
5229  2A14F8              LHLD     IELAPSE ; GET TIME TO GO
522C  7D                  MOV      A,L ; SEE IF '0'
522D  B4                  ORA      H
522E  C23B52              JNZ      IFC121 ; NOT YET
5231                      DELETE   CBLK09
5237  2A16F8              LHLD     INEXT ; GET NEXT STEP
523A  E9                  PCHL     ; GO DO IT
523B             ;
523B             IFC121
523B  2B                  DCX      H ; DECREMENT IT
523C  2214F8              SHLD     IELAPSE ; SAVE IT
523F  C9                  RET
5240             ;*************************************
5240             ;
```

```
5240                  ;
5240                  ;              ROUTINE TO CLEANLY EXIT FROM EXECUTING A METHOD
5240                  ;         ENTERED FROM TIMER QUE
5240                  ;
5240          IFCXIT  ENTRY
5240  AF             XRA       A ; CLEAR RUNNING FLAGS
5241  3206F8         STA       IRUNFLG
5244  3207F8         STA       IHLDFLG
5247  CD6E52         CALL      IFCHOME ; SET BACK TO INITIAL TEMP
524A                 DELETE    CBLK09 ; KILL TIMERS
5250                 DELETE    CBLK13
5256                 FILL      IACTBUF+5,CODE0,3
5263  3E32           MVI       A,ICODE ; INDICATE WHICH BUFFER THIS IS
5265  3223F8         STA       IACTBUF
5268  3E00           MVI       A,BLANK
526A  3224F8         STA       IACTBUF+1
526D  C9             RET
526E          ;***************************************
526E          ;
526E          ;              INITIALIZE THE INTERFACE TEMP
526E          ;
526E          ;
526E          IFCHOME ENTRY
526E  2A02C8         LHLD      IMETHD0+OF.INT+1 ; GET INITIAL TEMP
5271  2218F8         SHLD      ITEMP ; SAVE IT
5274  C9             RET
5275          ;***************************************
5275          ;
5275          ;         DO ALL RAMP CALCULATIONS PRIOR TO STARTING THE RUN
5275          ;
5275          IFCCALC ENTRY
5275  2A08C8         LHLD      IMETHD0+OF.HD1+1 ; GET HOLD1 TEMP
5278  EB             XCHG      ; PUT HOLD1 TEMP INTO 'DE'
5279  2A02C8         LHLD      IMETHD0+OF.INT+1 ; GET INITIAL TEMP
527C  7D             MOV       A,L ; 2'S COMPLEMENT INIT TEMP
527D  EEFF           XRI       OFFH
527F  6F             MOV       L,A
5280  7C             MOV       A,H
5281  EEFF           XRI       OFFH
5283  67             MOV       H,A
5284  23             INX       H
5285  19             DAD       D ; 'HL' = HOLD1 + ?-INIT)
5286  D29052         JNC       RATO1 ; IF HOLD > INIT
5289  AF             XRA       A ; SET RAMP1 DIRECTION TO UP
528A  3258E8         STA       IR1.DIR
528D  C39E52         JMP       RATO2
5290          RATO1
5290  3EFF           MVI       A,OFFH ; SET RAMP1 DIRECTION TO DOWN
5292  3258E8         STA       IR1.DIR
5295  7D             MOV       A,L ; 2'S COMPLEMENT
5296  EEFF           XRI       OFFH
5298  6F             MOV       L,A
5299  7C             MOV       A,H
529A  EEFF           XRI       OFFH
529C  67             MOV       H,A
529D  23             INX       H
529E          RATO2
529E  7D             MOV       A,L ; SEE IF DURATION IS '0'
529F  B4             ORA       H
52A0  C2A752         JNZ       RATO2.5 ; NO ...
52A3  AF             XRA       A ; PUT ZERO FOR RATE
52A4  C3AA52         JMP       RATO2.7
52A7          RATO2.5
52A7  3A06C8         LDA       IMETHD0+OF.RP1 ; GET RATE
52AA          RATO2.7
52AA  325EE8         STA       IR1.RATE
52AD  2259E8         SHLD      IR1.DUR ; DURATION IN DEGREES
52B0          ;         DO RAMP2
52B0  2A0EC8         LHLD      IMETHD0+OF.FNL+1 ; GET FINAL TEMP
52B3  EB             XCHG      ; PUT FINAL TEMP INTO 'DE'
52B4  2A08C8         LHLD      IMETHD0+OF.HD1+1 ; GET HOLD1 TEMP
52B7  7D             MOV       A,L ; 2'S COMPLEMENT HOLD1 TEMP
52B8  EEFF           XRI       OFFH
52BA  6F             MOV       L,A
52BB  7C             MOV       A,H
52BC  EEFF           XRI       OFFH
52BE  67             MOV       H,A
52BF  23             INX       H
52C0  19             DAD       D ; 'HL' = FINAL + (- HOLD1)
52C1  D2CB52         JNC       RATO3 ; IF FINAL > HOLD1
52C4  AF             XRA       A ; SET RAMP2 DIRECTION TO UP
52C5  3262E8         STA       IR2.DIR
52C8  C3D952         JMP       RATO4
52CB          RATO3
52CB  3EFF           MVI       A,OFFH ; SET RAMP2 DIRECTION TO DOWN
52CD  3262E8         STA       IR2.DIR
52D0  7D             MOV       A,L ; 2'S COMPLEMENT
52D1  EEFF           XRI       OFFH
52D3  6F             MOV       L,A
52D4  7C             MOV       A,H
52D5  EEFF           XRI       OFFH
52D7  67             MOV       H,A
52D8  23             INX       H
52D9          RATO4
52D9  7D             MOV       A,L ; SEE IF DURATION IS '0'
```

```
52DA  B4                       ORA        H
52DB  C2E252                   JNZ        RATO4.5 ; NO ...
52DE  AF                       XRA        A ; ELSE SET RATE TO '0'
52DF  C3E552                   JMP        RATO4.7
52E2              RATO4.5
52E2  3A0CC8                   LDA        IMETHDO+OF.RP2 ; GET RATE
52E5              RATO4.7
52E5  3268E8                   STA        IR2.RATE
52E8  2263E8                   SHLD       IR2.DUR ; DURATION IN DEGREES
52EB  C9                       RET
52EC          ;*********************************************************************
52EC                           END
52EC          ;*********************************************************************
52EC                           USE        EPROM6
6000          ;                STEADY TEMPERATURE INPUT ROUTINE (INIT, HOLD1, FINAL)
6000              SRINT
6000  C31860                   JMP        INPINT
6003              SRMP1
6003  C3EA61                   JMP        INPRMP1
6006              SRHD1
6006  C32360                   JMP        INPHD1
6009              SRMP2
6009  C3F561                   JMP        INPRMP2
600C              SRFNL
600C  C32E60                   JMP        INPFNL
600F          ;
600F              INPRTN
600F  CD0C40                   CALL       CALCULATP
6012  CD0C50                   CALL       CALCULATI
6015  C39482                   JMP        MAINO1
6018          ;
6018              INPINT       ENTRY
6018  210000                   LXI        H,OF.INT ; SAVE OFFSET TO SET POINT
601B                           SAVE       H ; SAVE FOR LATER
601C  2E32                     MVI        L,ICODE
601E  2662                     MVI        H,NCODE
6020  C33960                   JMP        INPF01
6023              INPHD1       ENTRY
6023  210600                   LXI        H,OF.HD1
6026                           SAVE       H
6027  2E22                     MVI        L,HCODE
6029  2620                     MVI        H,CODE1
602B  C33960                   JMP        INPF01
602E              INPFNL       ENTRY
602E  210C00                   LXI        H,OF.FNL
6031                           SAVE       H
6032  2E02                     MVI        L,FCODE
6034  2632                     MVI        H,ICODE
6036  C33960                   JMP        INPF01
6039              INPF01
6039  2209F8                   SHLD       DTBUF ; SHOW WHAT IS BEING ASKED FOR
603C              INPF01.5
603C                           FILL       DTBUF+2,BLANK^DOT,6
6049  2109F8                   LXI        H,DTBUF
604C  2239F8                   SHLD       INACTIVE
604F  010BF8                   LXI        B,DTBUF+2 ; WHERE TO START PUTTING CHARACTERS
6052  CD4063                   CALL       TIMTMP ; GET BOTH THE TEMPERATURE AND TIME
6055  FECE                     CPI        KY.PROBE ; SEE IF THE PROBE/INTERFACE KEY
6057  CA3C60                   JZ         INPF01.5 ; YES ...
605A  FECB                     CPI        KY.DSPLY ; SEE IF THEY WANT TO SEE THE CURRENT VALUES
605C  CA6660                   JZ         INPF02 ; YES ...
605F  FEC8                     CPI        KY.ENTER ; SEE IF THERE WERE NEW VALUES KY.ENTERED
6061  CAAA60                   JZ         INPF03
6064                           RESTOR     D ; FIX STACK
6065  E9                       PCHL       ; ELSE IT WAS A COMMAND
6066          ;                DISPLAY CURRENT VALUES
6066              INPF02
6066  3A00E0                   LDA        A1ST ; GET LEDS
6069  E620                     ANI        LD.PRB ; SEE IF PROBE LED IS LIT
606B  C27C60                   JNZ        INPF02.2 ; YES ...
606E  3A00E0                   LDA        A1ST
6071  E610                     ANI        LD.IFC ; SEE IF INTERFACE
6073  CAEE60                   JZ         INPF04 ; NO ...
6076  1101C8                   LXI        D,IMETHDO ; POINT TO INTERFACE METHOD
6079  C37F60                   JMP        INPF02.4
607C              INPF02.2
607C  1101D0                   LXI        D,PMETHDO ; POINT TO PROBE METHOD
607F              INPF02.4
607F                           RESTOR     H ; GET POINTER TO SET POINT
6080  19                       DAD        D
6081  3A00E0                   LDA        A1ST ; GET CURRENT LED CONDITION
6084  E6F0                     ANI        0F0H ; TURN OFF SECS, MINS, HOURS LEDS
6086  B6                       ORA        M ; SET CURRENT MODE
6087  3200E0                   STA        A1ST ; TURN IT ON
608A  23                       INX        H ; POINT TO TEMPERATURE
608B  5E                       MOV        E,M
608C  23                       INX        H
608D  56                       MOV        D,M
608E  EB                       XCHG       ; PUT TEMPERATURE INTO 'HL'
608F  CD1532                   CALL       BIN2PK ; CONVERT TO PACKED DECIMAL
6092  010BF8                   LXI        B,DTBUF+2
6095  CD3031                   CALL       PRVRT3 ; CONVERT TO 3 DISPLAYABLE CHARS
6098  EB                       XCHG       ; PUT POINTER INTO 'HL'
6099  23                       INX        H ; POINT TO TIME
609A  5E                       MOV        E,M
```

```
609B  23                    INX     H
609C  56                    MOV     D,M
609D  EB                    XCHG            ; PUT TIME INTO 'HL'
609E  CD1532                CALL    BIN2PK  ; CONVERT TO PACKED DECIMAL
60A1  010EF8                LXI     B,DTBUF+5
60A4  CD3031                CALL    PRVRT3  ; CONVERT TO 3 DISPLAYABLE CHARS
60A7  C30F60                JMP     INPRTN
60AA                ;               REPLACE CURRENT VALUES
60AA
60AA        INPF03
60AA  3A00E0                LDA     A1ST    ; GET LEDS
60AD  E620                  ANI     LD.PRB  ; SEE IF PROBE LED IS LIT
60AF  C2C060                JNZ     INPF03.2 ; YES ...
60B2  3A00E0                LDA     A1ST
60B5  E610                  ANI     LD.IFC  ; SEE IF INTERFACE
60B7  CAEE60                JZ      INPF04  ; NO ...
60BA  1101C8                LXI     D,IMETHDO ; POINT TO INTERFACE METHOD
60BD  C3C360                JMP     INPF03.4
60C0        INPF03.2
60C0  1101D0                LXI     D,PMETHDO ; POINT TO PROBE METHOD
60C3        INPF03.4
60C3                        RESTOR  H       ; GET POINTER TO SET POINT
60C4  19                    DAD     D
60C5  3A00E0                LDA     A1ST    ; GET THE SECS, MINS, HOURS LED
60C8  E60F                  ANI     00FH
60CA  77                    MOV     M,A     ; SAVE THE UNITS
60CB  23                    INX     H       ; POINT TO TEMPERATURE
60CC                        SAVE    H       ; SAVE POINTER
60CD  010BF8                LXI     B,DTBUF+2 ; POINT TO DISPLAY TEMP
60D0  CD6431                CALL    CNVRT3  ; CONVERT TO PACKED DECIMAL
60D3  CD8831                CALL    PK2BIN  ; CONVERT TO BINARY
60D6                        RESTOR  D
60D7  EB                    XCHG            ; PUT POINTER INTO 'HL'
60D8  73                    MOV     M,E
60D9  23                    INX     H
60DA  72                    MOV     M,D
60DB  23                    INX     H
60DC                        SAVE    H       ; SAVE POINTER
60DD  010EF8                LXI     B,DTBUF+5
60E0  CD6431                CALL    CNVRT3  ; CONVERT TO PACKED DECIMAL
60E3  CD8831                CALL    PK2BIN  ; CONVERT TO BINARY
60E6                        RESTOR  D
60E7  EB                    XCHG            ; PUT POINTER INTO 'HL'
60E8  73                    MOV     M,E
60E9  23                    INX     H
60EA  72                    MOV     M,D
60EB  C30F60                JMP     INPRTN
60EE        INPF04
60EE  CD7A33                CALL    BEEP2
60F1  C33C60                JMP     INPF01.5
60F4  ;***********************************************************************
60F4  ;
60F4  ;
60F4  ;               RAMP PROMPTING AND STORING ROUTINE (RAMP1, RAMP2)
60F4  ;
60F4  ;
60F4  10211000  IRATE   DB      CODE0,CODE1^DOT,CODE0,BLANK,MCODE,BLANK
      5200
60FA  10311000          DB      CODE0,CODE2^DOT,CODE0,BLANK,MCODE,BLANK
      5200
6100  10511000          DB      CODE0,CODE4^DOT,CODE0,BLANK,MCODE,BLANK
      5200
6106  10711000          DB      CODE0,CODE6^DOT,CODE0,BLANK,MCODE,BLANK
      5200
610C  10911000          DB      CODE0,CODE8^DOT,CODE0,BLANK,MCODE,BLANK
      5200
6112  20111000          DB      CODE1,CODE0^DOT,CODE0,BLANK,MCODE,BLANK
      5200
6118  20316000          DB      CODE1,CODE2^DOT,CODE5,BLANK,MCODE,BLANK
      5200
611E  20611000          DB      CODE1,CODE5^DOT,CODE0,BLANK,MCODE,BLANK
      5200
6124  30111000          DB      CODE2,CODE0^DOT,CODE0,BLANK,MCODE,BLANK
      5200
612A  30611000          DB      CODE2,CODE5^DOT,CODE0,BLANK,MCODE,BLANK
      5200
6130  40111000          DB      CODE3,CODE0^DOT,CODE0,BLANK,MCODE,BLANK
      5200
6136  50111000          DB      CODE4,CODE0^DOT,CODE0,BLANK,MCODE,BLANK
      5200
613C  60111000          DB      CODE5,CODE0^DOT,CODE0,BLANK,MCODE,BLANK
      5200
6142  70111000          DB      CODE6,CODE0^DOT,CODE0,BLANK,MCODE,BLANK
      5200
000E        NIRATES   EQU     ($-IRATE)/6
6148        ;
6148        PRATE
6148        ;       VERY SLOW RAMP RATES(DEGREES PER MINUTE)
6148  11102000          DB      CODE0^DOT,CODE0,CODE1,BLANK,MCODE,BLANK
      5200
614E  11103000          DB      CODE0^DOT,CODE0,CODE2,BLANK,MCODE,BLANK
      5200
6154  11106000          DB      CODE0^DOT,CODE0,CODE5,BLANK,MCODE,BLANK
      5200
615A  11201000          DB      CODE0^DOT,CODE1,CODE0,BLANK,MCODE,BLANK
      5200
```

```
6160  11301000              DB       CODE0^DOT,CODE2,CODE0,BLANK,MCODE,BLANK
      5200
6166  11601000              DB       CODE0^DOT,CODE5,CODE0,BLANK,MCODE,BLANK
      5200
616C  10102000              DB       CODE0,CODE0,CODE1,BLANK,MCODE,BLANK
      5200
6172  10103000              DB       CODE0,CODE0,CODE2,BLANK,MCODE,BLANK
      5200
6178               ;        SLOW RAMP RATE (DEGREES/MINUTE)
6178  10106000              DB       CODE0,CODE0,CODE5,BLANK,MCODE,BLANK
      5200
617E  10201000              DB       CODE0,CODE1,CODE0,BLANK,MCODE,BLANK
      5200
6184  10301000              DB       CODE0,CODE2,CODE0,BLANK,MCODE,BLANK
      5200
618A  10401000              DB       CODE0,CODE3,CODE0,BLANK,MCODE,BLANK
      5200
6190  10501000              DB       CODE0,CODE4,CODE0,BLANK,MCODE,BLANK
      5200
6196  10701000              DB       CODE0,CODE6,CODE0,BLANK,MCODE,BLANK
      5200
619C  20301000              DB       CODE1,CODE2,CODE0,BLANK,MCODE,BLANK
      5200
61A2  30101000              DB       CODE2,CODE0,CODE0,BLANK,MCODE,BLANK
      5200
61A8  40101000              DB       CODE3,CODE0,CODE0,BLANK,MCODE,BLANK
      5200
0011               NSPRATES EQU      ($-PRATE)/6
61AE               ;        FAST RAMP RATE (DEGREES/MILLISECOND)
61AE  10112000              DB       CODE0,CODE0^DOT,CODE1,BLANK,MCODE,SCODE
      52A2
61B4  10113000              DB       CODE0,CODE0^DOT,CODE2,BLANK,MCODE,SCODE
      52A2
61BA  10116000              DB       CODE0,CODE0^DOT,CODE5,BLANK,MCODE,SCODE
      52A2
61C0  10211000              DB       CODE0,CODE1^DOT,CODE0,BLANK,MCODE,SCODE
      52A2
61C6  10311000              DB       CODE0,CODE2^DOT,CODE0,BLANK,MCODE,SCODE
      52A2
61CC  10611000              DB       CODE0,CODE5^DOT,CODE0,BLANK,MCODE,SCODE
      52A2
61D2  20111000              DB       CODE1,CODE0^DOT,CODE0,BLANK,MCODE,SCODE
      52A2
61D8  30111000              DB       CODE2,CODE0^DOT,CODE0,BLANK,MCODE,SCODE
      52A2
61DE  60111000              DB       CODE5,CODE0^DOT,CODE0,BLANK,MCODE,SCODE
      52A2
61E4  30101000              DB       CODE2,CODE0,CODE0,BLANK,MCODE,SCODE
      52A2
001B               NPRATES  EQU      ($-PRATE)/6
61EA               ;
61EA               INPRMP1  ENTRY
61EA  210500                LXI      H,OF.RP1 ; OFFSET TO RAMP RATE
61ED                        SAVE     H ; FOR LATER
61EE  2E92                  MVI      L,RCODE
61F0  2620                  MVI      H,CODE1
61F2  C30062                JMP      INPR01
61F5               ;
61F5               INPRMP2  ENTRY
61F5  210B00                LXI      H,OF.RP2 ; OFFSET TO RAMP RATE
61F8                        SAVE     H ; SAVE FOR LATER
61F9  2E92                  MVI      L,RCODE
61FB  2630                  MVI      H,CODE2
61FD  C30062                JMP      INPR01
6200               ;
6200               ;        DISPLAY RAMP PROMPT
6200               INPR01
6200  2209F8                SHLD     DTBUF ; SHOW WHICH RAMP THIS IS
6203               INPR01.5
6203  3EFF                  MVI      A,0FFH ; SET RETURN FLAG FOR PROBE/INTERFACE KEY
6205  329EF8                STA      PIRTN
6208                        FILL     DTBUF+5,BLANK,3 ; CLEAR IT
6215                        FILL     DTBUF+2,BLANK^DOT,3
6222  2109F8                LXI      H,DTBUF ; POINT TO DISPLAY BUFFER
6225  2239F8                SHLD     INACTIVE
6228  210000                LXI      H,0
622B  3E7F                  MVI      A,07FH ; LARGEST 1 BYTE POSITIVE NUMBER
622D  3213F8                STA      RATE ; INITIALIZE RATE
6230               ;
6230               INPR02
6230  CD0585                CALL     INPUT ; SEE WHAT TO DO
6233  FECE                  CPI      KY.PROBE ; SEE IF THE PROBE/INTERFACE KEY
6235  CA0362                JZ       INPR01.5
6238  FEE2                  CPI      KY.RMPR ; BUMP UP RAMP RATE ?
623A  CA5B62                JZ       INPR04 ; YES ...
623D  FECB                  CPI      KY.DSPLY ; DISPLAY CURRENT VALUE ?
623F  CAC562                JZ       INPR07 ; YES ...
6242  FEC8                  CPI      KY.ENTER ; KY.ENTER NEW VALUES ?
6244  CA1163                JZ       INPR08 ; YES ...
6247                        COMAND   NCOMDS,ROUTNS,COMMDS ; SEE IF A COMMAND
6252  D23E63                JNC      INPR09 ; IF A COMMAND
6255  CD7A33                CALL     BEEP2
6258  C33062                JMP      INPR02
625B               ;        BUMP UP RATE
625B               INPR04
```

```
625B  3A00E0              LDA     A1ST ; GET LEDS
625E  E620                ANI     LD.PRB ; SEE IF THE PROBE LED IS LIT
6260  C27962              JNZ     INPRO4.2 ; YES ...
6263  3A00E0              LDA     A1ST ; SEE IF THE INTERFACE
6266  E610                ANI     LD.IFC
6268  CC7A33              CZ      BEEP2 ; NO ...
626B  CA3062              JZ      INPRO2
626E  3A13F8              LDA     RATE
6271  FE0D                CPI     NIRATES-1 ; MAX INTERFACE RATE
6273  F28862              JP      INPRO5
6276  C38162              JMP     INPRO4.4
6279          INPRO4.2
6279  3A13F8              LDA     RATE
627C  FE1A                CPI     NPRATES-1 ; MAX PROBE RATE
627E  F28862              JP      INPRO5
6281          INPRO4.4
6281  3C                  INR     A ; ELSE INCREMENT RATE
6282  3213F8              STA     RATE ; SAVE NEW RATE
6285  C38D62              JMP     INPRO6
6288          INPRO5
6288  3E00                MVI     A,0 ; RESET RATE TO START
628A  3213F8              STA     RATE ; SAVE NEW RATE
628D          INPRO6
628D  210000              LXI     H,0
6290  6F                  MOV     L,A ; RATE
6291  29                  DAD     H ; TIMES 6 FOR OFFSET
6292                      SAVE    H
6293  29                  DAD     H
6294                      RESTOR  B
6295  09                  DAD     B
6296  3A00E0              LDA     A1ST ; GET LEDS
6299  E620                ANI     LD.PRB ; SEE IF THE PROBE LED IS LIT
629B  C2AF62              JNZ     INPRO6.2 ; YES ...
629E  3A00E0              LDA     A1ST
62A1  E610                ANI     LD.IFC ; SEE IF INTERFACE
62A3  CC7A33              CZ      BEEP2 ; NO ...
62A6  CA3062              JZ      INPRO2
62A9  01F460              LXI     B,IRATE ; POINT TO INTERFACE TABLE
62AC  C3B262              JMP     INPRO6.3
62AF          INPRO6.2
62AF  014861              LXI     B,PRATE ; POINT TO PROBE TABLE
62B2          INPRO6.3
62B2  09                  DAD     B ; ADD TO OFFSET
62B3                      SAVE    H
62B4                      RESTOR  B ; POINT TO RATE
62B5          ;
62B5          ;                   PUT RATE INTO DISPLAY
62B5  110BF8              LXI     D,DTBUF+2 ; POINT TO DISPLAY BUFFER
62B8  2E06                MVI     L,6 ; 6 CHARS
62BA          INPRO6.5
62BA  0A                  LDAX    B
62BB  03                  INX     B
62BC  12                  STAX    D
62BD  13                  INX     D
62BE  2D                  DCR     L
62BF  C2BA62              JNZ     INPRO6.5
62C2          ;
62C2  C33062              JMP     INPRO2
62C5          ;                   DISPLAY CURRENT SETTINGS
62C5          INPRO7
62C5  3A00E0              LDA     A1ST ; GET LEDS
62C8  E620                ANI     LD.PRB ; SEE IF PROBE LED IS LIT
62CA  C2DE62              JNZ     INPRO7.1 ; YES ...
62CD  3A00E0              LDA     A1ST
62D0  E610                ANI     LD.IFC ; SEE IF INTERFACE
62D2  CC7A33              CZ      BEEP2 ; NO ...
62D5  CA3062              JZ      INPRO2
62D8  0101C8              LXI     B,IMETHD0 ; ELSE, POINT TO INTERFACE METHOD
62DB  C3E162              JMP     INPRO7.1.5
62DE          INPRO7.1
62DE  0101D0              LXI     B,PMETHD0 ; POINT TO PROBE METHOD
62E1          INPRO7.1.5
62E1                      RESTOR  H
62E2  09                  DAD     B ; POINT TO DATA
62E3  7E                  MOV     A,M ; GET RATE
62E4  210000              LXI     H,0 ; CLEAR FOR POINTER USE
62E7  6F                  MOV     L,A ; RATE POINTER
62E8  29                  DAD     H ; TIMES 6 FOR OFFSET
62E9                      SAVE    H
62EA  29                  DAD     H
62EB                      RESTOR  B
62EC  09                  DAD     B
62ED  3A00E0              LDA     A1ST ; GET LEDS
62F0  E610                ANI     LD.IFC ; SEE IF THE INTERFACE LED IS LIT
62F2  CAFB62              JZ      INPRO7.2 ; NO, GO GET THE PROBE RATE
62F5  01F460              LXI     B,IRATE ; POINT TO INTERFACE TABLE
62F8  C3FE62              JMP     INPRO7.3
62FB          INPRO7.2
62FB  014861              LXI     B,PRATE ; POINT TO PROBE TABLE
62FE          INPRO7.3
62FE  09                  DAD     B ; ADD OFFSET
62FF                      SAVE    H ; PUT 'HL' INTO 'BC'
6300                      RESTOR  B
```

```
6301                    ;                   PUT RATE INTO DISPLAY
6301   110BF8                      LXI      D,DTBUF+2
6304   2E06                        MVI      L,6
6306            INPRO7.5
6306   0A                          LDAX     B
6307   03                          INX      B
6308   12                          STAX     D
6309   13                          INX      D
630A   2D                          DCR      L
630B   C20663                      JNZ      INPRO7.5
630E   C30F60                      JMP      INPRTN
6311                    ;                   KY.ENTER NEW VALUES INTO IMETHDO
6311            INPRO8
6311   3A13F8                      LDA      RATE ; SEE IF A RATE HAS BEEN ENTERED
6314   FE7F                        CPI      07FH
6316   CA3062                      JZ       INPRO2 ; NO ...
6319   3A00E0                      LDA      A1ST ; GET LEDS
631C   E620                        ANI      LD.PRB ; SEE IF PROBE LED IS LIT
631E   C23263                      JNZ      INPRO8.2 ; YES ...
6321   3A00E0                      LDA      A1ST
6324   E610                        ANI      LD.IFC ; SEE IF INTERFACE
6326   CC7A33                      CZ       BEEP2 ; NO ...
6329   CA3062                      JZ       INPRO2
632C   0101C8                      LXI      B,IMETHDO ; POINT TO INTERFACE METHOD STORAGE
632F   C33563                      JMP      INPRO8.3
6332            INPRO8.2
6332   0101D0                      LXI      B,PMETHDO ; POINT TO PROBE METHOD STORAGE
6335            INPRO8.3
6335                                RESTOR  H ; GET OFFSET
6336   09                          DAD      B ; POINT TO ENTRY
6337   3A13F8                      LDA      RATE ; GET RATE
633A   77                          MOV      M,A ; STORE IT
633B   C30F60                      JMP      INPRTN
633E                    ;                   COMMAND INPUT
633E            INPRO9
633E                                RESTOR  B ; FIX STACK
633F   E9                          PCHL
6340            ;***********************************************************************
6340            ;                   TIME AND TEMPERATURE PROMPTING ROUTINE. PROMPTS FOR
6340            ;       3 DIGITS OF TEMPERATURE AND 3 DIGITS OF TIME.
6340            ;                   'BC' => WHERE TO STORE THE TEMPERATURE AND TIME IN
6340            ;                   DISPLAYABLE FORMAT
6340            ;                   'A' =  THE VALUE OF ANY COMMAND KEY HIT
6340            ;
6340            TIMTMP
6340                                SAVE    B ; SAVE POINTER
6341   3EFF                        MVI      A,0FFH ; SET RETURN FLAG FOR PROBE/INTERFACE KEY
6343   329EF8                      STA      PIRTN
6346   3E03                        MVI      A,3 ; PROMPT FOR 3 TEMP CHARS
6348   3211F8                      STA      CNT
634B            TT01
634B   CD0585                      CALL     INPUT ; GET A CHARACTER
634E   FECE                        CPI      KY.PROBE ; SEE IF THE PROBE/INTERFACE KEY
6350   CACC63                      JZ       TT05 ; YES ...
6353   FECB                        CPI      KY.DSPLY ; SEE IF THEY WANT TO SEE CURRENT VALUES
6355   CACC63                      JZ       TT05 ; YES ...
6358                                COMAND  NCOMDS,ROUTNS,COMMDS ; SEE IF A COMMAND
6363   D2CC63                      JNC      TT05 ; YES ...
6366   CD8732                      CALL     KB2BIN ; ELSE CONVERT TO BINARY
6369   DACE63                      JC       TT06 ; IF ILLEGAL
636C   CDA032                      CALL     BIN2DS ; CONVERT TO DISPLAYABLE
636F                                RESTOR  B ; GET POINTER
6370   02                          STAX     B ; SAVE THE CHARACTER
6371   03                          INX      B
6372                                SAVE    B ; SAVE THE POINTER
6373   2111F8                      LXI      H,CNT ; SEE IF DONE WITH TEMP
6376   35                          DCR      M
6377   C24B63                      JNZ      TT01 ; MORE TO DO
637A            ;
637A   3E03                        MVI      A,3 ; PROMPT FOR 3 TIME CHARACTERS
637C   3211F8                      STA      CNT
637F            TT02
637F   CD0585                      CALL     INPUT ; GET A CHARACTER
6382   FECE                        CPI      KY.PROBE ; SEE IF THE PROBE/INTERFACE KEY
6384   CACC63                      JZ       TT05 ; YES ...
6387   FECB                        CPI      KY.DSPLY ; IF THEY WANT TO SEE THE CURRRENT VALUES
6389   CACC63                      JZ       TT05 ; YES ...
638C   FEC8                        CPI      KY.ENTER ; SEE IF THE KY.ENTER KEY
638E   CABA63                      JZ       TT04 ; YES ...
6391                                COMAND  NCOMDS,ROUTNS,COMMDS ; SEE IF A COMMAND
639C   D2CC63                      JNC      TT05 ; YES ...
639F   CD8732                      CALL     KB2BIN ; CONVERT TO BINARY
63A2   DAD463                      JC       TT07 ; IF ILLEGAL
63A5   CDA032                      CALL     BIN2DS ; CONVERT TO DISPLAYABLE
63A8   2111F8                      LXI      H,CNT ; SEE IF DONE
63AB   35                          DCR      M
63AC   F2B363                      JP       TT03 ; MORE TO DO
63AF   34                          INR      M
63B0   C3D463                      JMP      TT07
63B3            ;
63B3            TT03
63B3                                RESTOR  B ; GET THE POINTER
63B4   02                          STAX     B ; SAVE THE CHARACTER
63B5   03                          INX      B
63B6                                SAVE    B ; SAVE THE POINTER
```

```
63B7  C37F63              JMP     TT02
63BA         ;
63BA                TT04
63BA  3A11F8              LDA     CNT ; ONLY ALLOW KY.ENTER WHEN ALL CHARS INPUT
63BD  FE00                CPI     0
63BF  C2D463              JNZ     TT07 ; MORE TO DO
63C2  3A00E0              LDA     A1ST ; GET LEDS
63C5  E630                ANI     LD.IFC+LD.PRB ; MAKE SURE EITHER THE PROBE OR INTERFACE IS SELECTED
63C7  CAD463              JZ      TT07 ; NO ...
63CA  3EC8                MVI     A,KY.ENTER ; TO RETURN TO CALLER
63CC         ;
63CC                TT05
63CC                RESTOR  B
63CD  C9                  RET
63CE         ;
63CE                TT06
63CE  CD7A33              CALL    BEEP2
63D1  C34B63              JMP     TT01
63D4                TT07
63D4  CD7A33              CALL    BEEP2
63D7  C37F63              JMP     TT02
63DA         ;*************************************************************
63DA                      END
0000  ERRORS
```

SYMBOL TABLE

```
A1          0000 00   A1ST        E000 01   A2          0004 00   A2ST        E003 01
A3          0008 00   A3ST        E006 01   ABSLUT      F802 01   ACODE       00B0 00
ACTIVE      F837 01   AIR.FCTR    0080 00   AIRMSG      8E22 01   AORG        0003 00
ATOD8       34FF 01   B.INTE      0080 00   B.TRGR      0008 00   B1          0001 00
B1ST        E001 01   B2          0005 00   B2ST        E004 01   B3          0009 00
B3ST        E007 01   BATERR      83A8 01   BATTRY      0040 00   BCODE       00C0 00
BD01        32AC 01   BDTMSG      83C1 01   BEEP        33CC 01   BEEP.1      0003 00
BEEP.2      0005 00   BEEP.3      0009 00   BEEP1       3351 01   BEEP2       337A 01
BEEP3       33A3 01   BIN2DS      32A0 01   BIN2PK      3215 01   BLANK       0000 00
BMXIT       8553 01   BNEXT       F89A 01   BOOST       3337 01   BORG        000B 00
C1          0002 00   C1ST        E002 01   C2          0006 00   C2ST        E005 01
C3          000A 00   C3ST        E008 01   CAL.PORT    0032 00   CALCULATI   500C 01
CALCULATP   400C 01   CALMSG      8D2D 01   CALPROBE    F89F 01   CB01        83C0 01
CBLK01      F040 01   CBLK02      F046 01   CBLK03      F04C 01   CBLK04      F052 01
CBLK05      F058 01   CBLK06      F05E 01   CBLK07      F064 01   CBLK08      F06A 01
CBLK09      F070 01   CBLK10      F076 01   CBLK11      F07C 01   CBLK12      F082 01
CBLK13      F088 01   CBLK14      F08E 01   CBLK15      F094 01   CBLK16      F09A 01
CBLK17      F0A0 01   CBLK18      F0A6 01   CBLK19      F0AC 01   CBLK20      F0B2 01
CCODE       00D0 00   CDSMSG      8006 01   CH1IN       E009 01   CH1INH      E00A 01
CH1OUT      E019 01   CH1OUTH     E01A 01   CH1ST       345C 01   CH2IN       E00B 01
CH2INH      E00C 01   CH2OUT      E01B 01   CH2OUTH     E01C 01   CH2ST       3460 01
CH3IN       E00D 01   CH3INH      E00E 01   CH3OUT      E01D 01   CH3OUTH     E01E 01
CH3ST       3464 01   CH4IN       E00F 01   CH4INH      E010 01   CH4OUT      E01F 01
CH4OUTH     E020 01   CH4ST       3468 01   CH5IN       E011 01   CH5INH      E012 01
CH5OUT      E021 01   CH5OUTH     E022 01   CH5ST       346C 01   CH6IN       E013 01
CH6INH      E014 01   CH6OUT      E023 01   CH6OUTH     E024 01   CH6ST       3470 01
CH7IN       E015 01   CH7INH      E016 01   CH7OUT      E025 01   CH7OUTH     E026 01
CH7ST       3474 01   CH8IN       E017 01   CH8INH      E018 01   CH8OUT      E027 01
CH8OUTH     E028 01   CH8ST       3478 01   CHAR        F81A 01   CHKBAT      83B0 01
CHKTMP      83C9 01   CLC         E7E9 4D   CLEAR       E5A2 4D   CLK01       8456 01
CLK02       849C 01   CLKXIT      84A1 01   CLOCK       8415 01   CM01        3274 01
CNT         F811 01   CNVRT1      3158 01   CNVRT2      315E 01   CNVRT3      3164 01
CNVRT4      316A 01   CNVRT5      316F 01   CNVRT6      3179 01   CNVRT7      317E 01
CODE0       0010 00   CODE1       0020 00   CODE2       0030 00   CODE3       0040 00
CODE4       0050 00   CODE5       0060 00   CODE6       0070 00   CODE7       0080 00
CODE8       0090 00   CODE9       00A0 00   COMAND      E68A 4D   COMMD       3267 01
COMMDS      800E 01   CONDIT1     C800 01   CONDIT2     D000 01   CORG        0013 00
COUNT0      F846 01   COUNT1      F848 01   COUNT2      F84A 01   COUNT3      F84C 01
COUNT4      F84E 01   COUNT5      F850 01   COUNT6      F852 01   COUNT7      F854 01
COUNT8      F856 01   COUNT9      F858 01   COUNTA      F85A 01   COUNTB      F85C 01
CT01        83F5 01   CT02        83F6 01   DATE        C8C5 01   DATI        F812 01
DATIM       84A2 01   DAYS        C8BA 01   DB01        32BA 01   DCODE       00E0 00
DELAY       DA6B 4D   DELETE      E789 4D   DEQUE       3083 01   DG01        324C 01
DG02        3255 01   DIGIT       324B 01   DIS01       897C 01   DISBYT      8BEA 01
DISDAT      89C2 01   DISDT       8961 01   DISPLAY     30BA 01   DISPLY      00CB 00
DISTIM      89A3 01   DORG        001B 00   DOT         0001 00   DQ01        308B 01
DQ02        3096 01   DQ10        30A1 01   DR2CM       E3A8 4D   DRCM        E4A3 4D
DRLC        E538 4D   DRRC        E394 4D   DS2BIN      32AE 01   DSPTR1      F800 01
DSPTR2      F82D 01   DT01        8602 01   DT01.0      8634 01   DT01.1      865C 01
DT01.2      8689 01   DT01.3      86B6 01   DT01.4      86DB 01   DT01.5      8708 01
DT01.6      872D 01   DT01.7      8748 01   DT010       8769 01   DT011       8783 01
DT011.0     87B5 01   DT011.1     87E5 01   DT011.2     8812 01   DT011.3     884C 01
DT011.3.1   8874 01   DT011.3.2   88A4 01   DT011.4     88D3 01   DT011.5     88F8 01
DT011.6     891D 01   DT012       893B 01   DT100       8959 01   DT020       89E1 01
DTBUF       F809 01   DTECLK      85E0 01   DTMSG       85D8 01   DUMMY       3301 01
ECODE       00F0 00   EIINT       5000 01   EITIM       5006 01   EIXIT       5003 01
ENTER       00C8 00   EORG        0023 00   EPINT       4000 01   EPROM4      4B25 00
EPROM5      52EC 00   EPROM6      6000 00   EPROM7      7000 00   EPTIM       4006 01
EPXIT       4003 01   EQUAL       0010 00   ETBUF       F81B 01   EXIT        3483 01
FCODE       0002 00   FILL        E6D0 4D   FL006A      84A9 01   FL006B      84DA 01
FL009D      8B60 01   FL009E      8BE1 01   FL00A7      8C72 01   FL00A8      8C83 01
FL00A9      8CDF 01   FL00AA      8CF0 01   FL00BD      4051 01   FL00C7      4265 01
FL00CD      43D2 01   FL00D1      44A9 01   FL00D8      45B8 01   FL0107      4977 01
FL0129      5053 01   FL0131      5178 01   FL013A      525D 01   FL013E      6043 01
FL0148      620F 01   FL0149      621C 01   FLVL01      438B 01   FLVL02      43B6 01
FORG        0027 00   FPINTVL     43FB 01   FPLVL1      42FA 01   FPLVL1.1    4306 01
FPLVL2      4329 01   FPLVL2.1    4335 01   FPLVL3      435A 01   FPLVL3.1    4366 01
FPRB01      4596 01   FPRMP1      451E 01   FPRMP1.5    453A 01   FPRMP2      455A 01
FPRMP2.5    4576 01   FRAMP       49FA 01   FRAMP1.3    4A25 01   FRAMP1.4    4A2B 01
```

| Symbol | Addr | B | Symbol | Addr | B | Symbol | Addr | B | Symbol | Addr | B |
|---|---|---|---|---|---|---|---|---|---|---|---|
| FRAMP1.5 | 4A3C | 01 | GAS.PORT | 0031 | 00 | GASFACTOR | F8A1 | 01 | GCODE | 0012 | 00 |
| GCREADYIN | 0020 | 00 | GOBST | DA8A | 4D | GORAMP | DC37 | 4D | GORG | 002B | 00 |
| HB01 | 8C40 | 01 | HB02 | 8C42 | 01 | HB03 | 8C4F | 01 | HB04 | 8C55 | 01 |
| HBEAT | 840C | 01 | HCODE | 0022 | 00 | HEART | 0020 | 00 | HEL.FCTR | 0080 | 00 |
| HELMSG | 8E2A | 01 | HEX2BIN | 8C34 | 01 | HEX2DS | 8C59 | 01 | HEXCHAR | 8C0F | 01 |
| HORG | 002F | 00 | HOURS | C8B9 | 01 | I4D01 | 32EA | 01 | I4D02 | 32F2 | 01 |
| I4D03 | 32F9 | 01 | I4DIVD | 32DF | 01 | I4M01 | 32C3 | 01 | I4M02 | 32CB | 01 |
| I4M03 | 32D8 | 01 | I4MULT | 32BC | 01 | IACTBUF | F823 | 01 | ICODE | 0032 | 00 |
| IELAPSE | F814 | 01 | IFC01 | 504B | 01 | IFC01.2 | 5088 | 01 | IFC01.5 | 50C2 | 01 |
| IFC02 | 50DB | 01 | IFC03 | 50F4 | 01 | IFC04 | 510D | 01 | IFC101 | 5171 | 01 |
| IFC102 | 51B4 | 01 | IFC103 | 51B7 | 01 | IFC104 | 51D9 | 01 | IFC109 | 51DD | 01 |
| IFC110 | 51E7 | 01 | IFC110.5 | 51EE | 01 | IFC111 | 5206 | 01 | IFC121 | 523B | 01 |
| IFCCALC | 5275 | 01 | IFCFNL | 5038 | 01 | IFCHD1 | 5025 | 01 | IFCHOME | 526E | 01 |
| IFCINT | 500F | 01 | IFCRMP1 | 5131 | 01 | IFCRMP2 | 5151 | 01 | IFCTIM | 5226 | 01 |
| IFCTMP | 8B40 | 01 | IFCXIT | 5240 | 01 | IHLDFLG | F807 | 01 | IM01 | 33FC | 01 |
| IM02 | 3402 | 01 | IM03 | 3410 | 01 | IMETHD0 | C801 | 01 | IMETHD1 | C812 | 01 |
| IMETHD2 | C823 | 01 | IMETHD3 | C834 | 01 | IMETHD4 | C845 | 01 | IMETHD5 | C856 | 01 |
| IMETHD6 | C867 | 01 | IMETHD7 | C878 | 01 | IMETHD8 | C889 | 01 | IMETHD9 | C89A | 01 |
| IMULT | 33F5 | 01 | IN01 | 306B | 01 | INACTIVE | F839 | 01 | INCTIM | 520B | 01 |
| INDAY | 8041 | 01 | INDRCT | 3061 | 01 | INEXT | F816 | 01 | INIT00 | 804D | 01 |
| INITAL | 8000 | 01 | INITMP | 5009 | 01 | INP00 | 8507 | 01 | INP00.5 | 850D | 01 |
| INP01 | 8543 | 01 | INP02 | 854A | 01 | INP05 | 855F | 01 | INP10 | 8569 | 01 |
| INP11 | 8581 | 01 | INP12 | 858E | 01 | INP12.5 | 85A5 | 01 | INP40 | 85AC | 01 |
| INP50 | 85C1 | 01 | INPF01 | 6039 | 01 | INPF01.5 | 603C | 01 | INPF02 | 6066 | 01 |
| INPF02.2 | 607C | 01 | INPF02.4 | 607F | 01 | INPF03 | 60AA | 01 | INPF03.2 | 60C0 | 01 |
| INPF03.4 | 60C3 | 01 | INPF04 | 60EE | 01 | INPFNL | 602E | 01 | INPHD1 | 6023 | 01 |
| INPIC | E294 | 4D | INPINT | 6018 | 01 | INPRO1 | 6200 | 01 | INPRO1.5 | 6203 | 01 |
| INPRO2 | 6230 | 01 | INPRO4 | 625B | 01 | INPRO4.2 | 6279 | 01 | INPRO4.4 | 6281 | 01 |
| INPRO5 | 6288 | 01 | INPRO6 | 628D | 01 | INPRO6.2 | 62AF | 01 | INPRO6.3 | 62B2 | 01 |
| INPRO6.5 | 62BA | 01 | INPRO7 | 62C5 | 01 | INPRO7.1 | 62DE | 01 | INPRO7.1.5 | 62E1 | 01 |
| INPRO7.2 | 62FB | 01 | INPRO7.3 | 62FE | 01 | INPRO7.5 | 6306 | 01 | INPRO8 | 6311 | 01 |
| INPRO8.2 | 6332 | 01 | INPRO8.3 | 6335 | 01 | INPRO9 | 633E | 01 | INPRMP1 | 61EA | 01 |
| INPRMP2 | 61F5 | 01 | INPROB | E1A5 | 4D | INPRTN | 600F | 01 | INPTMP | 4009 | 01 |
| INPUT | 8505 | 01 | INTIME | D892 | 4D | INTVL | 5111 | 01 | IORG | 0033 | 00 |
| IR.CBLK | E86C | 01 | IR.CNTRL | E871 | 01 | IR.DEST | E86F | 01 | IR.DIR | E86C | 01 |
| IR.DUR | E86D | 01 | IR.RATE | E872 | 01 | IR.STRT | E874 | 01 | IR1.CBLK | E858 | 01 |
| IR1.CNTRL | E85D | 01 | IR1.DEST | E85B | 01 | IR1.DIR | E858 | 01 | IR1.DUR | E859 | 01 |
| IR1.RATE | E85E | 01 | IR1.STRT | E860 | 01 | IR2.CBLK | E862 | 01 | IR2.CNTRL | E867 | 01 |
| IR2.DEST | E865 | 01 | IR2.DIR | E862 | 01 | IR2.DUR | E863 | 01 | IR2.RATE | E868 | 01 |
| IR2.STRT | E86A | 01 | IRATE | 60F4 | 01 | IRTIME | F82B | 01 | IRUNFLG | F806 | 01 |
| ITEMP | F818 | 01 | J1 | 3571 | 01 | J12 | 3576 | 01 | J2 | 3569 | 01 |
| JMP | 8748 | 01 | JORG | 0037 | 00 | KB01 | 328E | 01 | KB02 | 329B | 01 |
| KB2BIN | 3287 | 01 | KB2HEX | 8C1F | 01 | KBCHAR | 8BFF | 01 | KBCNT | 000D | 01 |
| KBDAT | 000C | 00 | KH01 | 8C27 | 01 | KH02 | 8C30 | 01 | KILLBEEP | 33EA | 01 |
| KILLPROB | E1E5 | 4D | KORG | 003B | 00 | KY.BOTH | 00CF | 00 | KY.CAL | 00C7 | 00 |
| KY.DSPLY | 00CB | 00 | KY.DTCLK | 00C9 | 00 | KY.DUMP | 00F7 | 00 | KY.EIGHT | 00D1 | 00 |
| KY.ENTER | 00C8 | 00 | KY.FINAL | 00D5 | 00 | KY.FIVE | 00C1 | 00 | KY.FOUR | 00C2 | 00 |
| KY.GCF | 00DA | 00 | KY.HOLD | 00EF | 00 | KY.HOLD1 | 00D7 | 00 | KY.IFACE | 00CD | 00 |
| KY.INIT | 00E5 | 00 | KY.INPT | 00DB | 00 | KY.MTHR | 00F4 | 00 | KY.MTHS | 00EC | 00 |
| KY.NINE | 00D0 | 00 | KY.ONE | 00F2 | 00 | KY.OUTPT | 00E3 | 00 | KY.PGC | 00D3 | 00 |
| KY.PRBTP | 00CD | 00 | KY.PROBE | 00CE | 00 | KY.RAMP1 | 00DD | 00 | KY.RAMP2 | 00D6 | 00 |
| KY.RESET | 00E6 | 00 | KY.RESUM | 00EE | 00 | KY.RMPR | 00E2 | 00 | KY.SEVEN | 00D2 | 00 |
| KY.SHFT | 00DE | 00 | KY.SIX | 00C0 | 00 | KY.STACT | 00CA | 00 | KY.START | 00E4 | 00 |
| KY.STC | 00D4 | 00 | KY.STOP | 00DC | 00 | KY.TBASE | 00CC | 00 | KY.THREE | 00F0 | 00 |
| KY.TWO | 00F1 | 00 | KY.ZERO1 | 00E9 | 00 | KY.ZERO2 | 00EA | 00 | KY.ZERO3 | 00E8 | 00 |
| LCODE | 0042 | 00 | LD.AGCS | 0004 | 00 | LD.AGCS2 | 0008 | 00 | LD.AUS | 0001 | 00 |
| LD.DHS | 0040 | 00 | LD.FTMP1 | 0020 | 00 | LD.FTMP2 | 0008 | 00 | LD.GCRDY | 0010 | 00 |
| LD.GCST | 0002 | 00 | LD.HBT | 0040 | 00 | LD.HOUR | 0008 | 00 | LD.IFC | 0010 | 00 |
| LD.INTH | 0010 | 00 | LD.IVL | 0002 | 00 | LD.IVL2 | 0080 | 00 | LD.MIN | 0004 | 00 |
| LD.MSEC | 0001 | 00 | LD.PGC | 0020 | 00 | LD.PRB | 0020 | 00 | LD.PRT | 0080 | 00 |
| LD.RMP1 | 0001 | 00 | LD.RMP2 | 0040 | 00 | LD.SEC | 0002 | 00 | LD.STA | 0080 | 00 |
| LD.THP | 0004 | 00 | LEDUPD | 3257 | 01 | LOOP1 | 8070 | 01 | LORG | 003F | 00 |
| MAIN | 8003 | 01 | MAIN00 | 807F | 01 | MAIN00.5 | 80EA | 01 | MAIN00.7 | 80ED | 01 |
| MAIN01 | 8294 | 01 | MAIN02 | 8297 | 01 | MATOD | 34DF | 01 | MCODE | 0052 | 00 |
| MINS | C8B8 | 01 | MORG | C8BB | 01 | MORG | 0083 | 00 | MOVE | E725 | 4D |
| MRCMSG | 8AB2 | 01 | MSEC | 3303 | 01 | MSTMSG | 8A2B | 01 | MULTPLX | 347C | 01 |
| MUX0 | 0070 | 00 | MUX1 | 0060 | 00 | MUX2 | 0050 | 00 | MUX3 | 0040 | 00 |
| MUX4 | 0030 | 00 | MUX5 | 0020 | 00 | MUX6 | 0010 | 00 | MUX7 | 0000 | 00 |
| MUXMK | 008F | 00 | MV0052 | 811B | 01 | MV0053 | 812B | 01 | MV0054 | 8153 | 01 |
| MV0055 | 8163 | 01 | MV0072 | 85F5 | 01 | MV007B | 8777 | 01 | MV0093 | 8A3B | 01 |
| MV0097 | 8AC2 | 01 | MV00AB | 8D3D | 01 | MV00B6 | 8E50 | 01 | MV00B7 | 8E6A | 01 |
| MV00B8 | 8E84 | 01 | MV00BB | 4032 | 01 | MV00BC | 4042 | 01 | MV00BE | 4073 | 01 |
| MV00C1 | 40F4 | 01 | MV00C2 | 4118 | 01 | MV00C5 | 4199 | 01 | MV00CE | 4417 | 01 |
| MV00CF | 4453 | 01 | MV00D6 | 4526 | 01 | MV00DD | 4562 | 01 | MV00DD | 4610 | 01 |
| MV00DE | 463F | 01 | MV012F | 5146 | 01 | MV0130 | 5166 | 01 | NCODE | 0062 | 00 |
| NCOMDS | 0011 | 00 | NDAYS | C8AB | 01 | NFINTRPT | F8A2 | 01 | NIRATES | 000E | 00 |
| NORG | 0087 | 00 | NPRATES | 001B | 00 | NSPRATES | 0011 | 00 | NUMS | 327D | 01 |
| OCODE | 0072 | 00 | OF.FNL | 000C | 00 | OF.HD1 | 0006 | 00 | OF.INT | 0000 | 00 |
| OF.RP1 | 0005 | 00 | OF.RP2 | 000B | 00 | OORG | 008B | 00 | P.CLR | 0040 | 00 |
| P.FNL | 0002 | 00 | P.IMAGE | F89C | 01 | P.INTE | 0010 | 00 | P.LOAD | 0001 | 00 |
| P.TRGR | 0004 | 00 | P.UPDN | 0020 | 00 | PACTBUF | F82F | 01 | PB01 | 3198 | 01 |
| PB02 | 31A0 | 01 | PB03 | 31A8 | 01 | PB04 | 31B0 | 01 | PB05 | 31B8 | 01 |
| PB06 | 31C0 | 01 | PB07 | 31C8 | 01 | PB08 | 31D0 | 01 | PB09 | 31D9 | 01 |
| PB10 | 31E1 | 01 | PB11 | 31E9 | 01 | PB12 | 31F1 | 01 | PB13 | 31F9 | 01 |
| PB14 | 3201 | 01 | PB15 | 3209 | 01 | PB16 | 3211 | 01 | PBS01 | 4065 | 01 |
| PBS02 | 4068 | 01 | PBS10 | 406B | 01 | PBS10.1 | 40A6 | 01 | PBS10.5 | 40B9 | 01 |
| PBS14 | 40D1 | 01 | PBS12 | 40E9 | 01 | PBS14 | 40E1 | 01 | PBS20 | 40FC | 01 |
| PBS21 | 410A | 01 | PBS22 | 410D | 01 | PBS30 | 4110 | 01 | PBS30.1 | 414B | 01 |
| PBS30.5 | 415E | 01 | PBS31 | 4176 | 01 | PBS32 | 418E | 01 | PBS34 | 4186 | 01 |
| PBS40 | 41A1 | 01 | PBS41 | 41AF | 01 | PBS42 | 41B2 | 01 | PBS50 | 41B5 | 01 |
| PCODE | 0082 | 00 | PELAPSE | F83B | 01 | PHLDFLG | F844 | 01 | PIC.CNTR | 0038 | 00 |
| PINTVL | 43D9 | 01 | PIRTN | F89E | 01 | PK2BIN | 3188 | 01 | PMETHD0 | D001 | 01 |
| PMETHD1 | D012 | 01 | PMETHD2 | D023 | 01 | PMETHD3 | D034 | 01 | PMETHD4 | D045 | 01 |
| PMETHD5 | D056 | 01 | PMETHD6 | D067 | 01 | PMETHD7 | D078 | 01 | PMETHD8 | D089 | 01 |
| PMETHD9 | D09A | 01 | PNCTIM | 48F9 | 01 | PNEXT | F83D | 01 | PORG | 008F | 00 |

| | | | | | | | |
|---|---|---|---|---|---|---|---|
| PRATE | 6148 01 | PRB.CNTR | 002C 00 | PRB.PIA | 0028 00 | PRB101 | 4487 01 |
| PRB102 | 44CC 01 | PRB103 | 44CF 01 | PRB109 | 44D9 01 | PRB110 | 44E0 01 |
| PRB110.5 | 44E4 01 | PRB111 | 4519 01 | PRB121 | 4926 01 | PRBCALC | 402A 01 |
| PRBENBL | 4988 01 | PRBHOME | 4990 01 | PRBSTRT | 400F 01 | PRBTIM | 4914 01 |
| PRBXIT | 492E 01 | PREAD | 0010 00 | PRGM | 8EC1 00 | PRTIME | F83F 01 |
| PRUNFLG | F843 01 | PRVRT1 | 3128 01 | PRVRT2 | 312C 01 | PRVRT3 | 3130 01 |
| PRVRT4 | 3134 01 | PRVRT5 | 313C 01 | PRVRT6 | 3146 01 | PRVRT7 | 314D 01 |
| PSTACK | F85E 01 | PTEMP | F841 01 | QORG | 0093 00 | QSIZE | 0020 00 |
| QUELST | F000 01 | QUEUE | 3062 01 | R.CBLK | F86A 01 | R.CNTRL1 | F86D 01 |
| R.CNTRL2 | F86E 01 | R.DEST | F87F 01 | R.DEST1 | F871 01 | R.DEST2 | F873 01 |
| R.DEST3 | F875 01 | R.DEST4 | F877 01 | R.DEST5 | F879 01 | R.DEST6 | F87B 01 |
| R.DEST7 | F87D 01 | R.DIR | F86A 01 | R.DUR | F86B 01 | R.IMPL | F893 01 |
| R.NEXT | F891 01 | R.RATE | F881 01 | R.RATE1 | F883 01 | R.RATE2 | F885 01 |
| R.RATE3 | F887 01 | R.RATE4 | F889 01 | R.RATE5 | F88B 01 | R.RATE6 | F88D 01 |
| R.RATE7 | F88F 01 | R.SPACE | F894 01 | R.STRT | F86F 01 | R1.CBLK | E800 01 |
| R2.CBLK | E82C 01 | RAMM0 | C8ED 00 | RAMM1 | D0AB 00 | RAMM2 | E029 00 |
| RAMM3 | E876 00 | RAMM4 | F0B8 00 | RAMM5 | F8A3 00 | RAMP | 331D 01 |
| RAT01 | 5290 01 | RAT02 | 529E 01 | RAT02.5 | 52A7 01 | RAT02.7 | 52AA 01 |
| RAT03 | 52CB 01 | RAT04 | 52D9 01 | RAT04.5 | 52E2 01 | RAT04.7 | 52E5 01 |
| RATE | F813 01 | RCODE | 0092 00 | RDRAM | E5F2 4D | RESTALL | E73A 4D |
| RESTOR | E75E 4D | RFIFO | E63F 4D | RIM | E7F4 4D | RMPRAT | 00E2 00 |
| RNEXT | F898 01 | RORG | 0097 00 | ROUTNS | 801F 01 | RST75 | 30AA 01 |
| SA1 | 355D 01 | SA10 | 3529 01 | SA100 | 34F2 01 | SA2 | 3550 01 |
| SA20 | 351C 01 | SA4 | 3543 01 | SA40 | 350F 01 | SA8 | 3536 01 |
| SAMPL | 3593 01 | SAVE | E770 4D | SAVEALL | E74D 4D | SCODE | 00A2 00 |
| SCRATCH | C8CD 01 | SECS | C8B7 01 | SENDV | 34CF 01 | SETBST | DC18 4D |
| SETEMP | E0BB 4D | SETFNL | DF37 4D | SETRATE | DDB5 4D | SIM | E7FF 4D |
| SMR01 | 8AD0 01 | SMR02 | 8AE7 01 | SMR03 | 8AF6 01 | SMR04 | 8B03 01 |
| SMR05 | 8B21 01 | SMR06 | 8B2F 01 | SMS01 | 8A49 01 | SMS02 | 8A60 01 |
| SMS03 | 8A6F 01 | SMS04 | 8A7C 01 | SMS05 | 8A99 01 | SMS06 | 8AA7 01 |
| SORG | 009B 00 | SPINTVL | 43D9 01 | SPLVL1 | 41BC 01 | SPLVL1.1 | 41C8 01 |
| SPLVL2 | 41EB 01 | SPLVL2.1 | 41F7 01 | SPLVL3 | 421C 01 | SPLVL3.1 | 4228 01 |
| SPRB01 | 424D 01 | SPRB01.5 | 429A 01 | SPRB02 | 42C8 01 | SPRB03 | 42E1 01 |
| SPRMP1 | 440F 01 | SPRMP1.1 | 442B 01 | SPRMP2 | 444B 01 | SPRMP2.1 | 4467 01 |
| SRAMP | 49B1 01 | SRAMP1.1 | 49DE 01 | SRAMP1.2 | 49EA 01 | SRC01 | 8D4B 01 |
| SRC02 | 8D6D 01 | SRC03 | 8D73 01 | SRC04 | 8D95 01 | SRC05 | 8D9B 01 |
| SRC06 | 8DBD 01 | SRC07 | 8DC3 01 | SRC08 | 8DE5 01 | SRC09 | 8E09 01 |
| SRC90 | 8E21 01 | SRCAL | 8D35 01 | SRD01 | 8B95 01 | SRD02 | 8BD2 01 |
| SRD03 | 8BD6 01 | SRD10 | 8BDA 01 | SRDUMP | 8B53 01 | SRFNL | 600C 01 |
| SRG01 | 8E5D 01 | SRG02 | 8E77 01 | SRG03 | 8E91 01 | SRG20 | 8E99 01 |
| SRG30 | 8EB2 01 | SRGCF | 8E3A 01 | SRH01 | 8329 01 | SRHD1 | 6006 01 |
| SRHOLD | 8300 01 | SRIN01 | 8CE5 01 | SRINP | 8CD2 01 | SRINT | 6000 01 |
| SRMP1 | 6003 01 | SRMP2 | 6009 01 | SRMRCL | 8ABA 01 | SRMSTR | 8A33 01 |
| SR001 | 8C78 01 | SROUT | 8C65 01 | SRP01 | 82F2 01 | SRR02 | 837D 01 |
| SRRESM | 8355 01 | SRSTOP | 82E7 01 | SRSTRT | 82A6 01 | SRT01 | 82C5 01 |
| STACK | E400 00 | STIKIT | 307A 01 | STORE | 3435 01 | SYSTEM | 359D 00 |
| SZ.IRCBK | 000A 00 | SZ.MTH | 0011 00 | SZ.RCBLK | 002C 00 | T.IMAGE | F89D 01 |
| T.INTE | 0004 00 | T.MAX | 00FA 00 | T.MIN | 0006 00 | T.MSEC | 0001 00 |
| T.TRGR | 0002 00 | TABLE1 | B800 00 | TABLE2 | B000 00 | TB01 | 8A07 01 |
| TB02 | 8A13 01 | TB03 | 8A1F 01 | TCODE | 00B2 00 | TGLTBS | 89E2 01 |
| TIM.CNTR | 0030 00 | TIM.PIA | 0034 00 | TIME | C8BD 01 | TIMER | E7DF 4D |
| TIMQUE | 3000 01 | TIMTMP | 6340 01 | TMMSG | 85D0 01 | TNEXT | F896 01 |
| TORG | 009F 00 | TQ01 | 3011 01 | TQ02 | 3050 01 | TQ03 | 304F 01 |
| TQ04 | 303C 01 | TSTFCTR | C8D1 01 | TSTFCTR1 | C8E3 01 | TSTFCTR2 | C8E9 01 |
| TSTFCTR3 | C8EB 01 | TSTRATES | C8D3 01 | TSTSLP1 | C8E5 01 | TSTSLP2 | C8E7 01 |
| TT01 | 634B 01 | TT02 | 637F 01 | TT03 | 63B3 01 | TT04 | 63BA 01 |
| TT05 | 63CC 01 | TT06 | 63CE 01 | TT07 | 63D4 01 | UCODE | 00C2 00 |
| UNUSED | 30B8 01 | UNUSED1 | F808 01 | UNUSED2 | F845 01 | UTILIZE | 30E5 01 |
| VAC.FCTR | 0080 00 | VACMSG | 8E32 01 | VCODE | 00D2 00 | VFPRMP1 | 4608 01 |
| VFPRMP1.5 | 4636 01 | VFPRMP2 | 4637 01 | VFPRMP2.5 | 4665 01 | VFPRMP2.8 | 4666 01 |
| VFR01 | 46A3 01 | VFR02 | 46F3 01 | VFR03 | 473D 01 | VFR04 | 4787 01 |
| VFR05 | 47D1 01 | VFR06 | 481B 01 | VFR07 | 4865 01 | VFR08 | 48AF 01 |
| VFRAMP | 4A42 01 | VFRAMP1 | 4A92 01 | VFRAMP2 | 4A55 01 | VFRAMP3 | 4A5B 01 |
| VIN | 3416 01 | VINLP | 341F 01 | VOUT | 3488 01 | WAIT | 3580 01 |
| WAITLP2 | 3584 01 | WCODE | 00E2 00 | WDRAM | E5CA 4D | WORDS | E65D 4D |
| X1 | 0003 00 | X2 | 0007 00 | X3 | 000B 00 | YCODE | 00F2 00 |
| YEARS | C8BC 01 | | | | | | |

What is claimed is:

1. A system for rapid energizaton of a delicate resistance element having extremely low thermal inertia, comprising:

(a) a first power supply coupled to said element which constantly produces a steep electrical voltage pulse of a first predetermined value (b) a second power supply independent of said first supply which continuously produces an electrical voltage of at least one second predetermined value, said second predetermined value being of substantially lesser magnitude than said first predetermined value, both of said independent supplies operating to produce their respective voltages simultaneously throughout an operation of said system, (c) means for triggering said first power supply to apply said steep pulse to said resistance element only during an initial first predetermined time interval as a function of a desired ultimate maximum temperature of said element, and (d) means coupled to said (c) means and to said element for preventing said steep pulse from being applied to said second power supply, said last-named means also operating to enable said voltage produced by said second power supply to be applied to said resistance element throughout a predetermined second time interval immediately following said first time interval and in response to the cessation of the application of said steep pulse to said element.

2. The system according to claim 1 wherein means are provided coupled to said first power supply for determining the duration of said first time interval as a function of the maximum temperature to be produced in said element during said second time interval.

3. The system according to claim 1 wherein means are provided to prevent coupling said steep electrical power pulse from said first power supply to said second power supply.

4. A system according to claim 1 with additional means for controlling the value of the voltage applied to said element by said second power supply as a function of a selected temperature of said element.

5. The system according to claim 4 wherein said additional means controls said electrical voltage coupled to said element according to a predetermined program.

6. The system according to claim 5 wherein said additional means controls the magnitude of the voltage applied to said element by said second power supply to produce a desired steady state temperature therein.

7. The system according to claim 4 wherein said additional means includes means for sensing the true average temperature of said element.

8. A system according to claim 4 wherein said (c) and said additional means are data processing means.

* * * * *